United States Patent [19]

Hutchinson et al.

[11] Patent Number: 5,883,093

[45] Date of Patent: Mar. 16, 1999

[54] PHENYLOXAZOLIDINONE ANTIMICROBIALS

[75] Inventors: Douglas K. Hutchinson, Kalamazoo, Mich.; Steven J. Brickner, Niantic, Conn.; Michael R. Barbachyn, Kalamazoo, Mich.; Mikio Taniguchi, Tsukuba; Kiyotaka Munesada, Shimozuma, both of Japan; Hiroyoshi Yamada, Tsukuba, Japan

[73] Assignee: Pharmacia & Upjohn Company, Kalamazoo, Mich.

[21] Appl. No.: 913,190

[22] PCT Filed: Sep. 12, 1995

[86] PCT No.: PCT/US95/10992

§ 371 Date: Apr. 23, 1997

§ 102(e) Date: Apr. 23, 1997

[87] PCT Pub. No.: WO96/13502

PCT Pub. Date: May 9, 1996

[51] Int. Cl.⁶ .................. A61K 31/42; A61K 31/395; C07D 205/04; C07D 263/14

[52] U.S. Cl. .......................... 514/210; 514/376; 540/200; 540/362; 540/364; 548/232; 548/950; 548/952; 548/953

[58] Field of Search ................... 540/200, 362, 540/364; 548/1, 3, 232, 950, 952, 953; 514/210, 375

[56] References Cited

U.S. PATENT DOCUMENTS

| | | | |
|---|---|---|---|
| 3,687,965 | 8/1972 | Fauran et al. | 260/307 |
| 4,250,318 | 2/1981 | Dostert et al. | 548/229 |
| 4,340,606 | 7/1982 | Fugitt et al. | 424/272 |
| 4,461,773 | 7/1984 | Gregory | 424/272 |
| 4,476,136 | 10/1984 | Dostert et al. | 424/272 |
| 4,801,600 | 1/1989 | Wang et al. | 514/376 |
| 4,921,869 | 5/1990 | Wang et al. | 514/376 |
| 4,948,801 | 8/1990 | Carlson et al. | 514/307 |

FOREIGN PATENT DOCUMENTS

| | | |
|---|---|---|
| 0 127 902 A3 | 12/1984 | European Pat. Off. . |
| 312000 A1 | 4/1989 | European Pat. Off. . |
| 316594 A1 | 5/1989 | European Pat. Off. . |
| 352781 A2 | 1/1990 | European Pat. Off. . |
| 0 359 418 A1 | 3/1990 | European Pat. Off. . |
| WO 90/02744 | 8/1990 | WIPO . |
| WO 93 09103 A | 5/1993 | WIPO . |
| WO 93/23384 | 11/1993 | WIPO . |

OTHER PUBLICATIONS

Gregory W. A., et al., *J. Med. Chem.*, 32, 1673–81 (1989).

Gregory W. A., et al., *J. Med. Chem.*, 33, 2569–78 (1990).

Wang C., et al., *Tetrahedron*, 45, 1323–26 (1989).

Brittelli, et al., *J. Med. Chem.*, 35, 1156 (1992).

*Primary Examiner*—Joseph K. McKane
*Attorney, Agent, or Firm*—Donald L. Corneglio; Lucy X. Yang

[57] ABSTRACT

The present invention relates to antimicrobial phenyloxazolidinone compounds having a pyrrolidinyl or azetidinyl moiety.

12 Claims, No Drawings

PHENYLOXAZOLIDINONE ANTIMICROBIALS

This application is the national phase of international application PCT/US/95/10992.

BACKGROUND OF THE INVENTION

The subject invention discloses new and usefull phenyloxazolidinone compounds having either a pyrrolidinyl or azetidinyl moiety. The compounds are useful antimicrobial agents, effective against a number of human and veterinary pathogens, including gram-positive aerobic bacteria such as multiply-resistant *staphylococci, streptococci* and *enterococci* as well as anaerobic organisms such as *Bacteroides spp.* and *Clostridia spp.* species, and acid-fast organisms such as *Mycobacterium tuberculosis, Mycobacterium avium* and *Mycobacterium spp.*

INFORMATION DISCLOSURE

The present compounds are related by their phenyloxazolidinone ring structure to the compounds disclosed in the publications below except that the subject compounds have a multi-substituted pyrrolidinyl or azetidinyl moiety. The instant compounds are unique and have useful antibacterial activity.

PCT/US93/03570 application discloses oxazolidinones containing a substituted diazine moiety and their uses as antimicrobials.

PCT/US92/08267 application discloses substituted aryl and heteroaryl-phenyl-oxazolidinones useful as antibacterial agents.

PCT/US89/03548 application discloses 5'indolinyl-5β-amidomethyloxazolidinones, 3-(fused-ring substituted) phenyl-5β-amidomethyloxazolidinones, and 3-(nitrogen substituted)phenyl-5β-amidomethyloxazolidinones which are usefull as antibacterial agents.

Other references disclosing various oxazolidinones include U.S. Pat. Nos. 4,801,600, 4,921,869, Gregory W. A., et al., *J. Med. Chem.*, 32, 1673–81 (1989); Gregory W. A., et al., *J. Med. Chem.*, 33, 2569–78 (1990); Wang C., et al., *Tetrahedron*, 45, 1323–26 (1989); and Brittelli, et al., *J. Med. Chem.*, 35, 1156 (1992).

European Patent Publication 352,781 discloses phenyl and pyridyl substituted phenyl oxazolidinones.

European Patent Publication 316,594 discloses 3-substituted styryl oxazolidinones.

European Patent Publication 312,000 discloses phenylmethyl and pyridinylmethyl substituted phenyl oxazolidinones.

SUMMARY OF THE INVENTION

In one aspect the subject invention is a compound of structural Formula I:

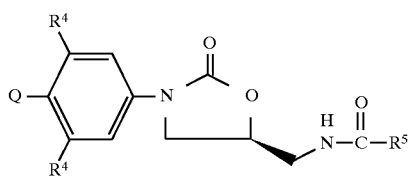

or pharmaceutically acceptable salts thereof wherein:

Q is selected from the structures i, ii, iii, iv and v:

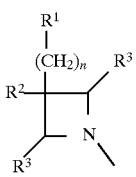   (i)

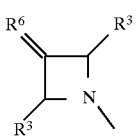   (ii)

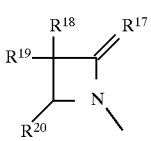   (iii)

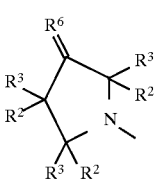   (iv)

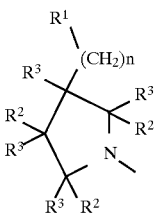   (v)

$R^1$ is
(a) H or F,
(b) $OR^7$,
(c) $SR^7$,
(d) $NR^8R^9$,
(e) CN,
(f) $C_1$–$C_4$ alkoxycarbonyl,
(g) carboxamide,
(h) $C_1$–$C_4$ acyl optionally substituted with one or more of the following: fluorine, hydroxy, $C_1$–$C_4$ alkoxy, $C_1$–$C_4$ acyloxy;
(i) NHO($C_1$–$C_6$ alkyl) or $NHOCH_2Ph$
(j) $NSO_2R$ where R is $C_{1-6}$ alkyl optionally substituted with one or more F, Cl, $C_{1-6}$ alkoxy or phenyl; each $R^2$ is independently selected from
(a) H or F,
(b) OH,
(c) OR where R is $C_1$–$C_6$ alkyl,
(d) $C_1$–$C_4$ alkyl,
(e) Ph;
each h $R^3$ is independently selected from
(a) H,
(b) $C_1$–$C_3$ alkyl which can be optionally substituted with F, Cl, hydroxy, $C_1$–$C_3$ alkoxycarbonyl, $C_1$–$C_3$ acyloxy, $C_1$–$C_3$ alkyoxy or $N(C_1$–$C_4$ alkyl$)_2$,
(c) phenyl,
(d) pyridyl;

$R^4$ is independently H, $OCH_3$, F or Cl;
$R^5$ is
 (a) hydrogen,
 (b) $C_1$–$C_8$ alkyl optionally substituted with one or more of the following: F, Cl, hydroxy, $C_1$–$C_8$ alkoxy, $C_1$–$C_8$ acyloxy,
 (c) $C_3$–$C_6$ cycloalkyl,
 (d) amino,
 (e) $C_1$–$C_8$ alkylamino,
 (f) $C_1$–$C_8$ dialkylamino,
 (g) $C_1$–$C_8$ alkoxy;
$R^6$ is
 (a) O,
 (b) S,
 (c) $NR^{10}$,
 (d) $CR^{11}R^{12}$,
 (e) $(OR)_2$, where R=$C_1$–$C_6$ alkyl,
 (f) $O(CH_2)_mO$,
 (g) $(SR)_2$, where R=$C_1$–$C_6$ alkyl,
 (h) $S(CH_2)_mS$
 (i) to fill the valence OH and H, H and H, H and F or F and F;
$R^7$ is
 (a) H,
 (b) $C_1$–$C_8$ alkyl optionally substituted with one or more of the following: F, Cl, —CN, hydroxy, $C_1$–$C_8$ alkoxy, $C_1$–$C_8$ acyloxy, $C_1$–$C_8$ alkoxycarbonyl, phenyl,
 (c) $C_1$–$C_8$ acyl optionally substituted with one or more of the following: hydroxy, $C_1$–$C_8$ alkoxy, $C_1$–$C_8$ acyloxy,
 (d) $C_1$–$C_8$ alkoxycarbonyl,
 (e) carboxamide, optionally substituted with a $C_1$–$C_4$ alkyl or phenyl on the carboxamide nitrogen,
 (f) phenyl, optionally substituted with one or more of the following: halogen, CN, $C_1$–$C_3$ alkoxy, $C_1$–$C_3$ alkoxycarbonyl, $C_1$–$C_4$ alkyl optionally substituted with one or more of F or $C_1$–$C_3$ alkoxy;
$R^8$ and $R^9$ are independently selected from:
 (a) H
 (b) $C_1$–$C_8$ alkyl optionally substituted with one or more of the following: F, Cl, —CN, hydroxy, $C_1$–$C_8$ alkoxy, $C_1$–$C_8$ acyloxy, $C_1$–$C_8$ alkoxycarbonyl, phenyl,
 (c) $C_1$–$C_8$ acyl optionally substituted with one or more of the following: hydroxy, $C_1$–$C_8$ alkoxy, $C_1$–$C_8$ acyloxy, amino, $C_1$–$C_4$ acylamino, amino-$C_1$–$C_4$ acylamino,
 (d) benzoyl optionally substituted with one or more of the following: F, Cl, hydroxy, $C_1$–$C_8$ alkoxy, $C_1$–$C_8$ acyloxy, amino, $C_1$–$C_4$ acylamino, $C_1$–$C_4$ alkoxycarbonylamino,
 (e) $C_1$–$C_8$ alkoxycarbonyl, benzyloxycarbonyl, tertbutoxycarbonyl,
 (f) carboxamide, optionally substituted with a $C_1$–$C_4$ alkyl or phenyl on the carboxamide nitrogen
 (g) trifluoracetyl
 (h) $CO(C_1$–$C_6$ alkyl);
$R^{10}$ is
 (a) H,
 (b) $OR^7$,
 (c) $NHR^7$,
 (d) $C_1$–$C_8$ alkyl optionally substituted with phenyl;
$R^{11}$ and $R^{12}$ are independently selected from:
 (a) H,F,
 (b) $C_1$–$C_4$ alkyl optionally substituted with halogen, hydroxy, $C_1$–$C_4$ alkoxy, $C_1$–$C_4$ alkoxycarbonyl, phenyl,
 (c) $C_1$–$C_8$ acyl,
 (d) $C_1$–$C_4$ alkoxycarbonyl,
 (e) CN;

$R^{17}$ is
 (a) O
 (b) S;

$R^{18}$ and $R^{19}$ are independently selected from:
 (a) H,
 (b) $C_1$–$C_4$ alkyl optionally substituted with halogen, hydroxy, $C_1$–$C_4$ alkoxy,
 (c) OH,
 (d) $C_1$–$C_4$ alkoxy optionally substituted with hydroxy or $C_1$–$C_4$ alkoxy,
 (e) $NR^8R^9$
 (f) —$OC(O)C_1$–$C_4$ alkyl;

$R^{20}$ is
 (a) H,
 (b) $CH_3$;

n is 0 or 1 and m is 2 or 3.

In one aspect the subject invention is a compound of structural Formula i:

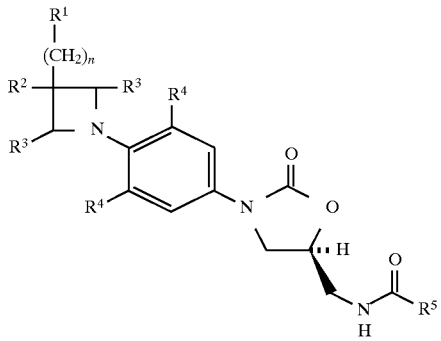

In another aspect the subject invention is composed of structural Formula ii:

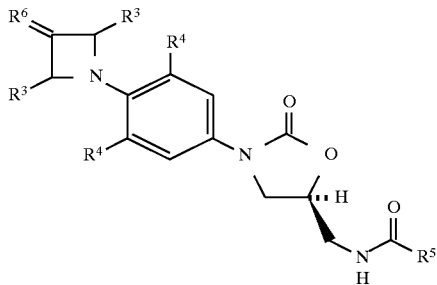

In another aspect the subject invention is composed of structural Formula iii:

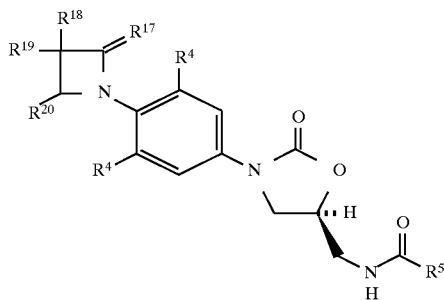

In yet another aspect, the subject invention is a compound of structural Formula iv:

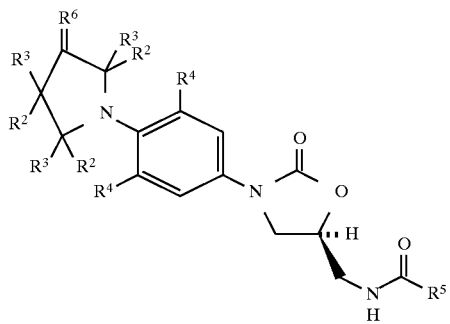

In yet another aspect, the subject invention is a compound of structural Formula v:

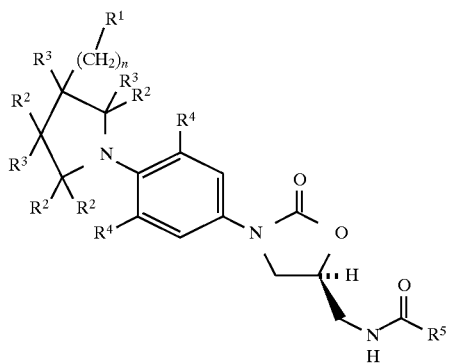

In another aspect, the subject invention is directed toward a method for treating microbial infections in humans or other warm-blooded animals by administering to a patient in need thereof an effective amount of a compound of Formula I (i–v) as described above. The compound can be administered in a pharmaceutical composition either orally, parenterally or topically. Preferably the compound is administered in an amount of from about 0.1 to about 100 mg/kg of body weight/day, more preferably, from about 3.0 to about 50 mg/kg of body weight/day.

DETAILED DESCRIPTION OF THE INVENTION

The present invention discloses novel substituted azetidinyl- and pyrrolidinyl-phenyloxazolidinones of structural Formula I (and as structurally represented in Formulas i–v) as described above. The compounds are useful antimicrobial agents, effective against a number of human and veterinary pathogens, particularly aerobic gram-positive bacteria, including multiply-resistant *staphylococci, enterococci* and *streptococci*, as well as anaerobic organisms such as bacteroides and *clostridia* species, and acid-fast bacteria such as as *Mycobacterium tuberculosis* and other mycobacterial species.

The $R^4$ substituents are preferably both fluorine and, more preferably, fluorine and hydrogen.

The $R^5$ substituent is preferably hydrogen, methyl, dichloromethyl, hydroxymethyl or methoxy. More preferably $R^5$ is hydrogen, methoxy or methyl. It is most preferred that $R^5$ is methyl.

The $R^6$ substituent is preferably O, $OCH_2CH_2O$, NOH and $NOCH_3$.

"Alkyl" means carbon atom chains having the designated number of carbon atoms which can be either straight chained or branched.

"Alkoxy" means the designated number of carbon atoms attached to an oxygen forming such groups as methoxy (—$OCH_3$), ethyloxy, butyloxy, etc. and isomeric forms thereof.

"Acyloxy" means the designated number of carbon atoms to form an organic acid where the OH group has been deleted, such as acetyl, $CH_3$ CO—; benzoyl, $C_6$ $H_5$CO—.

"Cycloalkyl" means the designated number of carbon atoms forming cyclopropyl, cyclobutyl, cyclopentyl, cyclohexyl, etc. and isomeric forms thereof.

"Ph" means phenyl. "Carbonyl" is a —C(=O)— moiety. "Amino" means an $NH_2$, "alkylamino" is where one of the hydrogen positions is replaced by an alkyl and "dialkylamino" is where both hydrogens are replaced by an alkyl group.

"Pharmaceutically acceptable salts" are acid addition salts which can be prepared by any of the art recognized means. Typical, acid addition salts include hydrochloride, hydrobromide, hydroiodide, sulfate, phosphate, acetate, propionate, lactate, malate, succinate, tartrate, cyclohexanesulfamates, methanesulfonates, ethanesulfonates, benxenesulfonates, toluenesulfonates, fumarates and other pharmaceutically acceptable couter ions for amines.

Azetindinyl-Phenyloxazolidinones:

The preferred absolute configuration at C-5 of the oxazolidinone ring of compounds claimed in this invention is as represented in the structures of Formula i and ii. This absolute configuration is called (S) under the Cahn-Ingold-Prelog nomenclature system. It is this (S)-enantiomer which is pharmacologically active as an antibacterial. The racemic mixture is useful in the same way and for the same purpose as the pure (S)-enantiomer; the difference is that twice as much racemic material must be used to produce the same antibacterial effect. It will be apparent to one skilled in the art that when a chiral center (R not H) is present in the azetidine fragment of compounds of structural Formula i, ii and iii, then diastereomers are possible. These diastereomers, in racemic and enantiomerically enriched forms, are also within the scope of the compounds of Formula i, ii and iii of the invention.

The preferred method of preparation of oxazolidinones of Formula i, ii and iii in enantiomerically pure form is depicted in Charts I–VI. Charts I–VI contain generic structural representations for the preparation of the various compounds of the invention centered around the core cyclic structure wherein Q is i, ii or iii.

As shown in Chart I, 3-hydroxyazetidines of structure 1 can be deprotonated with a suitable base, for example sodium hydride, in a suitable solvent, for example tetrahydrofuran (THF), and then alkylated with alkyl halides, for example methyl iodide, to give the azetidine ethers 2 ($R^{13}$= alkyl). If desired, aryl azetidine ethers 2 ($R^{13}$=optionally substituted phenyl) can be prepared from azetidinol 1 by employing known procedures (Taylor, C. R., Jr.; Cale, A. D., Jr.; Stauffer, H. F., Jr.

U.S. Pat. No. 4,956,359, 1990). The benzhydryl group of 1 and 2 is removed by hydrogenolysis in the presence of a mineral acid, for example hydrochloric acid, and in the presence of a suitable catalyst, for example palladium hydroxide on carbon, in a suitable solvent, such as methanol, to give the azetidines 3 ($R^{13}$=H, alkyl, phenyl). Compounds of structure 3 are then reacted with a functionalized nitrobenzene 4 (X=halogen or trifluoromethanesulfonate) in the presence of a suitable base/solvent combination, for example dibasic potassium phosphate in dimethyl sulfoxide or N,N-diisopropylethylamine in acetonitrile or THF, and at a suitable temperature, typically ambient temperature to 70° C., to afford the adduct 5. If it is desired that $R^1$ of a compound of structural Formula i or an advanced intermediate be hydroxy, then a suitable protecting group, such as the tert-butyldimethylsilyl moiety, is appended by reacting 5 ($R^{13}$=H) with tert-butyldimethylsilyl chloride in the presence of imidazole in a suitable solvent such as N,N-dimethylformamide (DMF) at ambient temperature to give 5 ($R^{13}$=tert-butyldimethylsilyl). It will be apparent to those skilled in the art that this protecting group is merely representative and that alternative protecting groups, such as those described in Greene, T. W.; Wuts, P. G. M. "Protective Groups in Organic Synthesis", 2nd ed.; John Wiley & Sons: New York, 1991, can be employed. The nitro group of 5 is then reduced by catalytic hydrogenation in the presence of a suitable catalyst, such as 10% palladium/carbon or W-2 Raney nickel, and in an appropriate solvent, for example TBF/$H_2O$. When this latter solvent system is utilized, the reaction mixture is first filtered to remove the catalyst and the filtrate containing the intermediate aniline is then treated with, for example, sodium bicarbonate and benzyl or methyl chloroformate to give the corresponding benzyl ($R^{14}$=$CH_2Ph$) or methyl ($R^{14}$=$CH_3$) urethane derivatives 6. The urethanes 6 are then deprotonated with a suitable base such as n-butyllithium (n-BuLi), lithium diisopropylamide (LDA) or lithium bis(trimethylsilyl)amide, in a suitable solvent such as tetrahydrofuran (THF) and at a suitable temperature such as −78° to 40° C. to give a lithiated intermediate which is then treated with commercially available (-)-(R)-glycidyl butyrate. Warming to ambient temperature then directly affords the 5-(hydroxymethyl) oxazolidinones 7 in enantiomerically enriched form.

As shown in Chart II, compound 7 is then converted to the corresponding mesylate 8 ($R^{15}$=methyl) or aryl sulfonate 8 ($R^{15}$=$ArSO_2$, for example p-toluenesulfonyl) by the action of, for example, methanesulfonyl chioride/pyridine or methanesulfonyl chloride/triethylamine/dichloromethane or p-toluenesufonyl chloride/pyridine. The resultant sulfonate derivative 8 is then reacted with an azide source such as sodium or potassium azide in an aprotic solvent such as N,N-dimethylformamide (DMF) or 1-methyl-2-pyrrolidinone optionally in the presence of a catalyst such as 18-crown-6 at a temperature of 50°–90 ° C. to afford the azide 9. The azide is then reduced by hydrogenation with palladium on carbon or a platinum catalyst in an appropriate solvent such as ethyl acetate or methanol to give the corresponding amine 10. Alternatively, the azide 9 can be reduced by treatment with a trivalent phosphorus compound such as triphenylphosphine in a suitable solvent such as tetrahydrofuran followed by the addition of water. The intermediate amine 10 may also be prepared by treatment of the phthalimide derivative 11 (obtained by reacting sulfonate 8 with potassium phthalimide in a suitable solvent, for example, acetonitrile at reflux temperature) with methylamine in ethanol/$H_2O$ at reflux temperature. Alternatively, the amine 10 may be prepared directly from the mesylate 8 by ammonolysis with aqueous ammonium hydroxide in a solvent system consisting of $H_2O$/ispropano/THF in a sealed reaction vessel immersed in a 70°–95 ° C. oil bath. The armine 10 is then acylated by reactions known to those skilled in the art to give oxazolidinones of structure 12. For example, the amine can be reacted with an acid chloride or anhydride in a basic solvent such as pyridine at a temperature ranging from −30° to 30° C. to provide the acylated compound 12 ($R^5$=optionally substituted alkyl). It will be apparent to one skilled in the art that other carbonyl groups within the scope of this invention can be readily appended to the amine 10 by standard acylation techniques, for example those highlighted in March, J. "Advanced Organic Chemistry", 3rd ed.; John Wiley & Sons: New York, 1985; p 370–375, to give additional examples of 12. If it is desired that $R^{13}$ be H, then the appended tert-butyldimethylsilyl protecting group of selected examples of 12 is removed employing appropriate conditions, such as those noted in Greene, T. W.; Wuts, P. G. M. "Protective Groups in Organic Synthesis", 2nd ed.; John Wiley & Sons: New York, 1991, especially aqueous hydrofluoric acid in acetonitrile at ambient temperature, to give the corresponding alcohol. The compounds of structure 12 ($R^{13}$=H, alkyl, optionally substituted phenyl) represent examples of azetidine-substituted oxazolidinone antibacterial agents of Formula I, which are the subject of this invention.

The azetidine-containing oxazolidinones 12, themselves examples of antibacterial agents of structural Formula i, can be further elaborated to additional compounds of Formula i and also examples of structural Formula ii as shown in Chart III. For example, 12 ($R^{13}$=H) can be oxidized to the corresponding azetidinone 13 by reacting it with catalytic tetra-n-propylammonium perruthenate in the presence of N-methylmorpholine N-oxide and molecular sieves in acetonitrile/dichloromethane. Compound 13 is an example of an antibacterial agent of structural Formula ii. The ketone moiety of 13 is amenable to further modification. Reaction of 13 with Lawesson's reagent or alternative reagents, as described in March, J. "Advanced Organic Chemistry", 4th ed.; John Wiley & Sons: New York, 1992; p 893–894, provides the corresponding thioketone 14 ($R^6$=S). Oximes 14 (for example, $R^6$=NOH and NOC$H_3$) are readily prepared by reacting 13 with, for example, hydroxylamine hydrochloride or methoxylamine hydrochloride in the presence of a suitable base, such as pyridine, and in an appropriate solvent, for instance methanol, at ambient temperature. Various hydrazone derivatives ($R^6$=NNH$R^7$) can be prepared by reacting 13 with hydrazines, as described in Greene, T. W.; Wuts, P. G. M. "Protective Groups in Organic Synthesis", 2nd ed.; John Wiley & Sons: New York, 1991, p 212–213 and March, J. "Advanced Organic Chemistry", 4th ed.; John Wiley & Sons: New York, 1992; p 904–905. Imines 14 ($R^6$=N-alkyl or N-aryl) are synthesized by treating 13 with primary amines, as described in March, J. "Advanced Organic Chemistry", 4th ed.; John Wiley & Sons: New York, 1992; p 896–897. Olefinic derivatives (14: $R^6$=CR$^{11}$R$^{12}$) are prepared by reacting 13 with various olefinating reagents, such as phosphorus ylides and the like, which are known to one skilled in the art. Representative examples are described in March, J. "Advanced Organic Chemistry", 4th ed.; John Wiley & Sons: New York, 1992;

p 956–963. For the case where $R^6$ is $CF_2$ this would involve treatment of ketone 13 with ($NaO_2CCF_2Cl$) sodium difluorochloroacetate and triphenylphosphate, as described in Tetrahedron Letters 1964, p 1461. The resulting olefinic bond can be reduced by catalytic hydrogenation or other methods known to one skilled in the art to furnish examples of structural Formula i. Other compounds of structure 14, for example cyclic and acyclic ketals and dithio ketals, can be prepared by reacting compound 13 with diols, dithiols, alcohols or thiols under conditions, for example, described in Greene, T. W.; Wuts, P. G. M. "Protective Groups in Organic Synthesis", 2nd ed.; John Wiley & Sons: New York, 1991, p 177–207. Compound 12 ($R^{13}$=H) can also be converted to various derivatives 15 ($R^{16}$=optionally substituted acyl, alkoxycarbonyl, carboxamide, etc.) by treatment of 12 with various carbonyl derivatives, such as anhydrides, alkyl chloroformates, isocyanates and the like, in the presence of appropriate bases, and in suitable solvents known to one skilled in the art. Compounds 14 and 15 represent examples of oxazolidinone antibacterial agents of structural Formula i and ii.

Charts IV–VI outline procedures to prepare examples of structural Formula i wherein $R^1$ is a group other than $OR^7$. As shown in Chart IV, the mesylate 16, obtained by reacting azetidinol starting material 1 with methanesulfonyl chloride in the presence of triethylamine and dichloromethane, is reacted with a variety of nucleophiles. For example, treatment of 16 with ammonia, primary amines or secondary amines affords 3-aminoazetidines of structure 17. Similarly, treatment of 16 with thiolates or cyanide provides the adducts 18 and 19. respectively. Compound 19 can be reduced with lithium aluminum hydride and the like to the corresponding 3-(aminomethyl)azetidine 20. Compound 19 can also be converted to the carboxylate derivative 21. Those skilled in the art can further transform the carboxylate moiety of 21 to the corresponding carboxamide or various acyl groups which, after further elaboration, comprise additional examples of antibacterial agents of structural Formula i. Compounds 17 and 20 can be further N-alkylated by procedures known to one skilled in the art, including treatment of 17 and 20 with alkyl halides or tosylates in the presence of a suitable base. Alternatively, selected alkyl groups can be appended on the nitrogen of 17 and 20 by a reductive alkylation procedure as described in March, J. "Advanced Organic Chemistry", 4th ed.; John Wiley & Sons: New York, 1992; p 898–900. In the cases of amino intermediates 17 and 20, when a free NH is present, it is necessary to protect these moieties to enable some subsequent reactions to proceed uneventfully. The amino group can be converted to the corresponding t-butyl carbamate (BOC), benzyl carbamate (Cbz), trifluoroacetamide, or phthalimide derivatives and the like, as required, employing procedures described in Greene, T. W.; Wuts, P. G. M. "Protective Groups in Organic Synthesis", 2nd ed.; John Wiley & Sons: New York, 1991, p 309–403. The benzhydryl protecting group of 17–21 is then removed by hydrogenolysis in the presence of a suitable catalyst, for example palladium hydroxide on carbon, and in the presence of a mineral acid, for example hydrochloric acid, to give the intermediate azetidines 22 ($R^1$ not $OR^7$).

Chart V outlines the elaboration of intermediate azetidines 22 to examples of structural Formula i ($R^1$ not $OR^7$). The chemistry is essentially identical to that described in Chart I. Compound 22 is initially converted to the nitrobenzene derivative 23. Reduction and conversion to carbamates of structure 24 is accomplished as described previously. As described in Chart I, intermediate 24 is elaborated to the optically active 5-(hydroxymethyl)oxazolidinone 25. Application of procedures outlined in Chart II then allows for conversion of 25 to compounds of structure 26. Removal of any appended protecting groups, for example BOC groups on compounds where $R^1$ is amino, is achieved by methods known to one skilled in the art, for instance those described in Greene, T. W.; Wuts, P. G. M. "Protective Groups in Organic Synthesis", 2nd ed.; John Wiley & Sons: New York, 1991. The resultant free amino group can then be N-alkylated or N-acylated, if desired. to give additional compounds of structure 26. which are examples of oxazolidinone antibacterial agents of structural Formula i.

Chart VI depicts a variation of the chemistry outlined in Chart IV wherein the hydroxyazetidinylphenyloxazolidinone intermediate 12 ($R^{13}$=OH) is converted to the corresponding mesylate 27 by the action of methanesulfonyl chloride in the presence of a suitable base, such as triethylamine, and in an appropriate solvent, for example dichloromethane. The same nucleophilic displacements described in Chart IV for the mesylate 16 can be carried out on the more functionalized mesylate 27 to give compounds 28–30. Employing procedures similar to those described in Chart IV, 30 can be converted to the compounds 31 and 32. Compounds 28–32 are examples of oxazolidinone antibacterial agents of structural Formula i, which are the subject of this invention. It will be apparent to one skilled in the art that compounds 28–32 are merely representative examples and are themselves amenable to further chemical modification to give additional examples of structural Formula i.

Chart VII outlines procedures to prepare compounds of structural Formula iii. 2-Azetidinones of structure 33 are treated with an appropriate base, for example sodium hydride, in a suitable solvent, for instance THF, to give a deprotonated intermediate which is then reacted with a functionalized nitrobenzene derivative 4 (X=halogen) to furnish the adduct 34. It will be apparent to one skilled in the art that appropriate protecting groups, for example those described in Greene, T. W.; Wuts, P. G. M. "Protective Groups in Organic Synthesis", 2nd ed.; John Wiley & Sons: New York, 1991, are required for selected $R^{18}$ and $R^{19}$ substituents of compound 33. Intermediate 34 can be converted via steps outlined in Charts I and II to compounds of structure 35, themselves examples of structural Formula iii, which are the subject of this invention. Alternatively, the azetidinyl-substituted intermediate 36, prepared via procedures outlined in Charts I and II, is oxidized to the corresponding azetidinone 35 ($R^{17}$=O) with, for example, catalytic ruthenium tetroxide in the presence of a suitable oxidant, such as sodium metaperiodate, and in a suitable solvent system, for example ethyl acetate/water. To prepare examples of compound 35 where $R^{17}$ is S, selected azetidinone intermediates are reacted with Lawesson's reagent or the like.

Examples of azetindinyl-phenyloxazolidinones that can be prepared as part of this invention are as follows:

1. (S)-N-[[3-[3-fluoro-4-(3-methoxy-1-azetidinyl)phenyl]-2-oxo-5-oxazolidinyl]methyl]acetamide
2. (S)-N-[[3-[3-fluoro-4-(3-hydroxy-1-azetidinyl)phenyl]-2-oxo-5-oxazolidinyl]methyl]acetamide
3. (S)-N-[[3-[3-fluoro-4-[3-[N-(2-fluoroethyl)-N-methylamino]-1-azetidinyl]phenyl]-2-oxo-5-oxazolidinyl]methyl]acetamide
4. (S)-N-[[3-[3-fluoro-4-(3-oxo-1-azetidinyl)phenyl]-2-oxo-5-oxazolidinyl]methyl]acetamide
5. (S)-N-[[3-[3-fluoro-4-[3-(methoxyimino)-1-azetidinyl]phenyl]-2-oxo-5-oxazolidinyl]methyl]acetamide 6. (S)-N-[[3-(3-fluoro-4-[3-methoxy-3-methyl-1-azetidinyl)phenyl]-2-oxo-5-oxazolidinyl]methyl]acetamnide
7. (S)-N-[[3-[3-fluoro-4-(3-hydroxy-3-methyl-1-azetidinyl)phenyl]-2-oxo-5-oxazolidinyl]methyl]acetamide
8. (S)-N-[[3-[3-fluoro-4-(2-oxo-1-azetidinyl)phenyl]-2-oxo-5-oxazolidinyl]methyl]acetamide
9. (S)-N-[[3-[3-fluoro-4-(3-hydroxy-2-oxo-1-azetidinyl)phenyl]-2-oxo-5-oxazolidinyl]methyl]acetamide
10. (S)-N-[[3-[3-fluoro-4-(3-methoxy-2-oxo-1-azetidinyl)phenyl]-2-oxo-5-oxazolidinyl]methyl]acetamide
11. N-[[3-[3-fluoro-4-(3-methyl-2-oxo-1-azetidinyl)phenyl]-2-oxo-(5S)-oxazolidinyl]methyl]acetamide
12. (S)-N-[[3-[3-fluoro-4-(3,3-dimethyl-2-oxo-1-azetidinyl)phenyl]-2-oxo-5-oxazolidinyl]methyl]acetamide
13. (S)-N-[[3-[3-fluoro-4-[3-(hydroxyimino)-1-azetidinyl]phenyl]-2-oxo-5-oxazolidinyl]methyl]acetamide
14. N-[[3-[3-fluoro-4-[(2R)-methyl-3-oxo-1-azetidinyl]phenyl]-2-oxo-(5S)-oxazolidinyl]methyl]acetamide
15. N-[[3-[3-fluoro-4-[(2S)-methyl-3-oxo-1-azetidinyl]phenyl]-2-oxo-(5S)-oxazolidinyl]methyl]acetamide
16. N-[[3-[3-fluoro-4-[3-(methoxyimino)-(2R)-methyl-1-azetidinyl]phenyl]-2-oxo-(5S)-oxazolidinyl]methyl]acetamide
17. N-[[3-[3-fluoro-4-[3-(methoxyimino)-(2S)-methyl-1-azetidinyl]phenyl]-2-oxo-(5S)-oxazolidinyl]methyl]acetamide
18. (S)-N-[[3-[3-fluoro-4-[3-(difluoromethylene)-1-azetidinyl]phenyl]-2-oxo-5-oxazolidinyl]methyl]acetamide
19. (S)-N-[[3-[3-fluoro-4-[3-(methoxymethylene)-1-azetidinyl]phenyl]-2oxo-5-oxazolidinyl]methyl]acetamide
20. (S)-N-[[3-[3-fluoro-4-[3-(hydroxyacetyl)-1-azetidinyl]phenyl]-2-oxo-5-oxazolidinyl]methyl]acetamide
21. (S)-N-[[3-[3-fluoro-4-[3-(methoxyamino)-1-azetidinyl]phenyl]-2-oxo-5-oxazolidinyl]methyl]acetamide
22. N-[[3-[3-fluoro-4-[2,4-dimethyl-3-oxo-1-azetidinyl]phenyl]-2-oxo-(5S)-oxazolidinyl]methyl]acetamide
23. N-[[3-[3-fluoro-4-[2,4-dimethyl-3-(methoxyimino)-1-azetidinyl]phenyl]-2-oxo-(5S)-oxazolidinyl]methyl]acetamide
24. N-[[3-[3-fluoro-4-[2,4-dimethyl-3-methoxy-1-azetidinyl]phenyl]-2-oxo-5S)-oxazolidinyl]methyl]acetamide
25. (S)-N-[[3-[3-fluoro-4-[(3S)-methoxy-(2R)-methyl-1-azetidinyl]phenyl]-2-oxo-5-oxazolidinyl]methyl]acetamide
26. (S)-N-[[3-[3-fluoro-4-[(3R)-methoxy-(2S)-methyl-1-azetidinyl]phenyl]-2-oxo-5-oxazolidinyl]methyl3acetamide
27. (S)-N-[[3-[3-fluoro-4-[(3S)-hydroxy-(2R)-methyl-1-azetidinyl]phenyl]-2-oxo-5-oxazolidinyl]methyl]acetamide
28. (S)-N-[[3-[3-fluoro-4-((3R)-hydroxy-(2S)-methyl-1-azetidinyl]phenyl]-2-oxo-5-oxazolidinyl]methyl]acetamide
29. (S)-N-[[3-[3-fluoro-4-(3-fluoro-1-azetidinyl)phenyl]-2-oxo-5-oxazolidinyl]-methyl]acetamide
30. (S)-N-[[3-[3-fluoro-4-[3-fluoro-(2R)-methyl-1-azetidinyl]phenyl]-2-oxo-5-oxazolidinyl]methyl]acetamide
31. (S)-N-[[3-[3-fluoro-4-[3-fluoro-(2S)-methyl-1-azetidinyl]phenyl]-2-oxo-5-oxazohidinyl]methyl]acetamide
32. (S)-N-[[3-[3-fluoro-4-[3-[(hydroxyacetyl)amino]-1-azetidinyl]phenyl]-2-oxo-5-oxazolidinyl]methyl]acetamide
33. (S)-N-[[3-[3-fluoro-4-[3-[(methanesulfonyl)amino]-1-azetidinyl]phenyl]-2-oxo-5-oxazolidinyl]methyl]acetamide
34. (S)-N-[[3-[3-fluoro-4-[3-[(formyl)amino]-1-azetidinyl]phenyl]-2-oxo-5-oxazolidinyl]methyl]acetamide
35. (S)-N-[[3-[3-fluoro-4-[3-[(acetyl)amino]-azetidinyl]phenyl]-2-oxo-5-oxazolidinyl]methyl]acetamide
36. (S)-N-[[3-[3-fluoro-4-[3-[(methycarbinyl)amino]-1-azetidinyl]phenyl]-2-oxo-5 oxazolidinyl]methyl]acetamide
37. (S)-N-[[3-[3-fluoro-4-[3-[(benzyloxycarbonyl)amino]-1-azetidinyl]phenyl]-2-oxo-oxazolidinyl]methyl]acetamide Pyrrolidinyl-Phenyloxazolidinones The present invention discloses novel substituted pyrrolidinyl phenyloxazolidinones according to the structural Formulas iv and v, above. The compounds are useful antimicrobial agents, effective against a number of human and veterinary pathogens particularly aerobic Gram-positive bacteria, including multiply-antbiotic resistant *staphylococci* and *streptococci*, as well as anaerobic organisms such as *bacteroides* and *clostridia* species, and acid-fast organisms such as *Mycobacterium tuberculosis* and other mycobacterium species.

The most preferred compounds in this series would be prepared as the optically pure enantiomers having the (S)-configuration according to the Cahn-Ingold-Prelog notation at C5 of the oxazolidinone ring. Optically pure material could be prepared by one of a number of asymmetric syntheses or by resolution from a racemic modification by selective crystallization of a salt from, for example, the racemic modification of intermediate amine 11 (as described in Chart XII) with an appropriate optically active acid such as dibenzoyl tartarate or 10 amphorsulfonic acid, followed by treatment with base to afford the optically active amine. Although the (S)- enantiomer of this series of compounds is preferred since it is pharmacologically active as an antibacterial, the racemic modification is also useful in the same manner as the pure (S)- enantiomer; the difference being that twice as much racemic material is required to elicit the same antibacterial effect. In addition, it will be apparent to one skilled in the art that when a chiral center is present on the pyrrolidine moiety of compounds of structural Formula iv and v that diastereoisomers are possible. These diastereomers, either in the racemic or configurationally enriched forms, are also within the scope of the compounds of Formulas iv and v of this invention.

The preferred method of preparation for the pyrrolidinyl phenyloxazolidinones of Formula iv and v in enantiomerically pure form is depicted in Charts XI–XIX. Charts XI–XIX contain generic structural representations for the preparation of the various compounds of the invention centered around the core cyclic structure wherein Q is iv or v.

As shown in Chart XI, derivatives of structure 1, either commercially available or prepared by modification of literature methods, (U.S. Pat. No. 4,753,953) can be protected with a diol, such as ethylene glycol, under conditions of acid catalysis with azeotropic removal of water to form the acetal 2. The N-benzyl group of 2 is then removed by hydrogenolysis in the presence of a noble metal catalyst, such as palladium on carbon or palladium hydroxide on carbon, in a suitable solvent, to give the pyrrolidine derivative 3. Pyrrolidine derivative 3 can be treated with a nitrobenzene derivative 4 (Y=halogen or trifluoromethanesulfonate) in a suitable base and solvent combination, for example dibasic potassium phosphate in DMSO, and a suitable temperature, typically ambient to 90° C., to afford adduct 5. The nitro group of 5 is then reduced by catalytic hydrogenation in the presence of catalysts such as palladium on carbon or W-2 Raney nickel in a suitable solvent, such as ethyl acetate or tetrahydrofuran (THF) to give the aniline derivative 6. When THF is used as the solvent for this reduction, it is not necessary to remove the catalyst by filtration or isolate aniline derivative 6 but merely to purge the reaction vessel with an inert gas such as nitrogen add saturated aqueous sodium bicarbonate solution and treat the resulting cooled mixture with either benzyl or methyl chloroformate to give the corresponding benzyl ($R^{14}$=$CH_2$Ph) or methyl carbamate ($R^{14}$=$CH_3$) derivatives 7. Either of the carbamate derivatives 7 can be deprotonated with a lithium base such as n-butyllithium, lithium diisopropyl amide (LDA), or lithium bis(trimethylsilyl)amide (LHMDS), in a suitable solvent, such as THF, N, N-dimethylformamide (DMF), or mixtures thereof, at a suitable temperature, such as −78° C. to 40° C. to give a lithiated intermediate which is directly treated with commercially available (R)-(-)-glycidyl butyrate. Warming this reaction mixture to ambient temperature then affords the (hydroxymethyl)oxazolidinones 8 in highly enantiomerically enriched form.

As shown in Chart XII, compound 8 can be converted to the corresponding mesylate ($R^{15}$=$CH_3$) or tosylate ($R^{15}$=p-$CH_3C_6H_4$) by treatment with methanesulfonyl chloride in the presence of triethylamine or pyridine or p-toluenesulfonyl chloride in the presence of pyridine. The resulting sulfonate derivative 9 can then be treated with an alkalai metal azide such as sodium or potassium azide in an aprotic dipolar solvent such as DMF or N-methylpyrrolidinone (NMP) with an optional catalyst such as 18-crown-6 at a temperature in the range of 50°–90° C. to afford azide 10. The azide 10 can be reduced to the corresponding amine 11 by hydrogenation in the presence of a palladium, platinum or nickel catalyst, in an appropriate solvent such as ethyl acetate, THF, or methanol. Alternatively, azide 10 can be reduced by treatment with triphenylphoshine or other trivalent phosphorus compounds in a solvent such as THF, followed by addition of water. Amine 11 can also be prepared by treatment of sulfonate 9 with potassium phthalmidate in DMF at 40°–90° C. or in refluxing acetonitrile to afford the phthalimide 12 which is then deprotected by treatment, for example, with aqueous methylamine in refluxing ethanol affording 11. A more direct route to amine 11 is the treatment of sulfonate 9 with aqueous ammonia solution in an isopropyl alcohol-THF solvent system in a sealed tube heated at 75°–105° C. in an oil bath. Amine 11 is then acylated by reactions well-known to those skilled in the art to give (acylaminomethyl) oxazolidinones of structure 13. For example, amine 11 can be treated with an acid chloride or anhydride in the presence of a base such as pyridine or triethylamine at temperatures ranging from −40–40° C. to provide the acyl derivative 13 ($R^5$=optionally substituted alkyl). It can be seen that under similar reaction conditions that other acyl derivatives, such as carbamates, can be readily prepared. Finally, treatment of 13 with aqueous acid, such as p-toluenesulfonic acid in aqueous acetone, will hydrolyze the acetal functionality to afford the corresponding carbonyl derivative 14 which represents an example of pyrrolidinone-substituted antibacterial agents of Formula iv. It can be seen by those skilled in the art that other embodiments of a compound of Formula iv can be prepared from 14. Reaction of 14 with Lawesson's reagent or other alternative reagents such as hydrogen sulfide would afford the thioketone derivative 15 ($R^6$=S). Oximes ($R^6$=NHOH or NHO$CH_3$) can be prepared from 14 by treatment with either hydroxylamine hydrochloride or methoxyamine hydrochloride in the presence of a base such as pyridine or sodium acetate in a solvent such as methanol. Hydrazone derivatives ($R^6$=NNH$R^{12}$) can be prepared by treatment of 14 with hydrazine derivatives. Similarly, imines ($R^6$=N$R^{12}$) can be prepared by treatment of 14 with a primary amine. Olefinic derivatives ($R^6$=C$R^{11}R^{12}$) can be prepared by treatment of 14 with various olefination reagents such as phosphorus ylides (Wittig reagents), phosphonate esters (Horner-Emmons Reagents) or other reagents known to those skilled in the art. It can easily be seen that reduction of the olefinic bond by catalytic hydrogenation or other methods will provide examples of structural Formula v.

Charts XII–XV outline the preparation of examples of structural Formula v wherein $R^1$=O$R^7$, $R^3$=H and n=0. As shown in Chart XIII, intermediate 1, described in Chart XI is reduced to the alcohol 16 by treatment with any of a number of standard hydride reducing agents such as sodium borohydride, lithium aluminum hydride or the like. The benzyl protecting group of 16 can then be subsequently removed by hydrogenolysis using a catalyst such as palladium hydroxide on carbon, or 10% palladium on carbon to give amino alcohol 17. It must be noted here that some examples of 17 may be commercially available, but the possibility of the de novo synthesis of 17 must be considered, in order to include more complex examples of high antibacterial interest. Amino alcohol 17 can then be allowed to react with a nitrobenzene derivative such as 4 (Y=halogen or trifluoromethanesulfonate), in the presence of an appropriate base such as dibasic potassium phosphate in a suitable solvent, such as dimethylsulfoxide at temperatures in the range of 40°–90° C. to afford 18. It will be apparent to those skilled in the art that subsequent transformations of 18 will require that the hydroxyl group be protected. This can be accomplished, for example, by preparation of the tert-butyldimethyl silyl ether 19(R=Si($CH_3$)$_2$t-Bu) by treatment of 18 with tert-butyldimethylchlorosilane in the presence of a base such as imidazole or diisopropylethyl amine, optionally in the presence of 4-dimethylaminopyridine as a catalyst, in a suitable solvent such as DMF, THF, or dichloromethane. The nitro group of 19 can be reduced by hydrogenation in the presence of a catalyst such as 10% palladium on carbon or W-2 Raney nickel in a solvent such as THF or ethyl acetate to give aniline derivative 20. Aniline derivative 20 is not routinely isolated but is directly treated with saturated sodium bicarbonate and an alkyl chloroformate derivative such as benzyl chloroformate or methyl chloroformate to give the corresponding benzyl ($R^{14}$=$CH_2$Ph) or methyl ($R^{14}$=$CH_3$) carbamate derivative 21. Carbamate derivative 21 can then be deprotonated by a base such as n-butyllithium or lithium diisopropylamide (LDA) or lithium bis(trimethylsilyl)amide (LHMDS) in a solvent such as THE or DMF or mixtures thereof, at a temperature in the range −78° C. to 40° C. to give a lithiated derivative which is treated with the commercially available (R)-(-)-glycidyl butyrate. The resulting mixture is then warmed to ambient temperature to directly afford the (hydroxymethyl)oxazolidinones 22.

It can be seen by those skilled in the art that intermediate oxazolidinone 22 can be used in a number of ways to prepare various embodiments of compounds of structural Formula iv. As Shown in Chart XIV, oxazolidinone 22 can be converted to (acylaminomethy)oxazolidinone 23 by a sequence of reactions identical with that used to convert compound 8 to compound 13 in Chart XII. The protecting group of 23 (R=Si(CH$_3$)$_2$t-Bu) can be removed by standard methods known to those skilled in the art, such as treatment with tetrabutylammonium fluoride in THF to afford alcohol 24, which is an example of a compound of structural Formula v. Compound 24 can be converted to a number of derivatives 23 (R=R$^7$=optionally substituted acyl, alkoxyearbonyl, carboxamide, etc.) by treatment with various carbonyl derivatives, such as anhydrides, acyl chlorides, alkyl and aryl chloroformates, isocyanates, and the like, using appropriate bases and catalysts in suitable solvents known to one skilled in the art. Thus, compounds 23 and 24 represent examples of oxazolidinone antibacterial agents of structural Formula v.

Another use of intermediate oxazolidinone 22 is illustrated in Chart XV. As shown 22 (R=Si(CH$_3$)$_2$t-Bu) can be protected, for example, by treatment with tert-butydiphenylchlorosilane and an appropriate base such as diisopropylethylamine and a catalyst such as 4-dimethylaminopyridine in a suitable solvent, such as dichloromethane, THF, or the like to give bis-protected derivative 25 (R=Si(CH$_3$)$_2$t-Bu, R$^1$=SiPh$_2$t-Bu). Bis-protected derivative 25 is selectively deprotected to remove the tert-butyldimethylsilyl ether protecting group by treatment with acetic acid using a co-solvent of water and THF in a variety of proportions at temperatures in the range 50°–100° C. to afford alcohol 26. Alcohol 26 can be alkylated on the unprotected hydroxyl group by treatment with a suitable base, such as sodium hydride, in a dipolar aprotic solvent such as THF, DMF or the like, in the presence of an alkyl halide such as methyl iodide or its substituted derivatives to give silyl ether 25 (R=R$^7$=straight or branched chain alkyl, R$^1$=SiPh$_2$t-Bu). The silicon protecting group of 25 can then be removed by treatment with tetrabutylammonium fluoride in a solvent such as TBF to afford alcohol 27 (R=straight or branched chain alkyl). Alcohol 27 can then be converted to (acylaminomethyl)oxazolidinone derivative 28 (R$^7$=straight or branched chain alkyl) by a sequence of reactions identical with that used to convert 8 to 13 in Chart XII. (Acylaminomethyl) oxazoldinone derivative 27 is an example of an oxazoldinone antibacterial agent of structural Formula v.

Charts XVI–XIX outline the preparation of examples of structural Formula v where R$^1$ is the substituted amino moiety. Chart XVI outlines the case where R$^1$=NHR and n=0. As shown, aminopyrrolidine 29, either available commercially or prepared by methods well known in the art optionally protected as either the trifluoroacetamide (R=COCF$_3$) or the tert-butoxycarbonyl derivative (R=CO$_2$t-Bu) is hydrogenolyzed in the presence of a suitable catalyst such as palladium hydroxide on carbon in an appropriate solvent such as methanol to remove the benzyl protecting group affording pyrrolidine 30. Pyrrolidine 30 can be reacted with a nitroaromatic compound such as 4 in the presence of a suitable base, such as dibasic potassium phosphate, in an appropriate solvent, such as dimethyl sulfoxide (DMSO) or DMF to afford displacement product 31. The nitro group of 31 is reduced by hydrogenation in the presence of 10% palladium on carbon or W-2 Raney nickel in a suitable solvent such as TBF or ethyl acetate to afford aniline derivative 32. The aniline derivative 32 is not routinely isolated, but generally is treated directly with saturated sodium bicarbonate solution and an alkyl chloroformate derivative such as benzyl chloroformate or methyl chloroformate to afford the corresponding benzyl (R$^{14}$=CH$_2$Ph) or methyl (R$^{14}$=CH$_3$) carbamate derivative 33. In the case where 33 is protected by an acyl derivative, it is necessary to remove the protecting group by appropriate means well-known to those skilled in the art to afford primary amine derivative 34. Amine 34 is then treated with a dialkyl urea derivative, such as N, N-dimethyl urea or N, N-dibenzyl urea in the presence of formaldehyde under conditions pioneered by Knapp, et al.[2] to afford either the dimethyl (R=CH$_3$) or dibenzyl (R=CH$_2$Ph) triazone derivative 35. Triazone 35 can then be deprotonated with a base such as n-butyllithium, lithium diisopropylamide (LDA) or lithium bis(trimethylsilyl)amide in a solvent such as DMF or mixtures of DMF and THF at temperatures in the range of −78° to −40° C. to give a lithiated derivative which is directly treated with commercially available (R)-(-)-glycidyl butyrate. The resulting mixture is then warmed to ambient temperature to afford (hydroxymethyl)oxazolidinone 36.

Chart XVII describes the conversion of triazone derivative 36 to compounds of Formula v. As shown, triazone derivative 36 can be converted to (acylaminomethyl) oxazolidinone 37 by means identical to those used to convert compound 8 to 13 in Chart XII. The triazone group of 37 can be removed by hydrolysis with aqueous hydrochloric acid or treatment with saturated ammonium chloride solution to afford amine 38. Compound 38 can be converted to a number of carbonyl derviatives 39 (R=optionally substituted alkyl, alkoxy, alkylamino, etc.) by treatment with various carbonyl derivatives, such as acyl chlorides, anhydrides, alkyl and aryl chloroformates, isocyanates and the like, using appropriate bases and catalysts in suitable solvents known to one skilled in the art. In addition, compound 38 can be converted into a number of alkyl derivatives 40 (R=optionally substituted straight or branched chain alkyl) by treatment with an appropriate aldehyde or ketone in the presence of hydrogen gas and a catalyst such as 10% palladium on carbon or a reagent such as sodium cyanoborohydride in a protic solvent such as methanol. Alternatively, 38 could be treated with an optionally substituted alkyl halide in the presence of a base such as sodium carbonate in a suitable solvent such as TBF or acetonitrile, optionally in the presence of water. Thus prepared, compounds 39 and 40 constitute examples of compounds of Formula v where n=0.

Chart XVIII describes the preparation of examples of compounds of structural Formula v where R$^3$=H, R$^1$=NR$^8$R$^9$ and n=1. As shown, pyrrolidine derivative 41, available by known methods,[1a,3] optionally protected as either the trifluoroacetamide (R=COCF$_3$) or the tert-butoxycarbonyl derivative (R=CO$_2$t-Bu) is debenzylated by hydrogenolysis in the presence of a catalyst such as palladium hydroxide on carbon, or 10% palladium on carbon in a suitable solvent such as methanol to afford 42. Pyrrolidine 42 can be allowed to react with a nitrobenzene derivative such as 4 in the presence of a base, such as dibasic potassium phosphate. in a solvent such as dimethyl sulfoxide (DMSO) to afford the aromatic displacement product 43. Aryl pyrrolidine 43 can be reduced by hydrogenation in the presence of a catalyst, such as 10% palladium on carbon or W-2 Raney nickel in a solvent such as THF or ethyl acetate to afford aniline derivative 44. Aniline derivative 44 is not routinely isolated, but is generally treated directly with saturated sodium bicarbonate solution and an alkyl chloroformate such as benzyl or methyl chloroformate to afford the corresponding benzyl ($R^{14}=CH_2Ph$) or methyl ($R^{14}=CH_3$) carbamate derivative 45. In the case where 45 is protected as an acyl derivative, it is necessary to remove the protecting group by appropriate means well-known to those skilled in the art to afford primary amine derivative 46. Amine 46 is then treated with a dialkyl urea derivative, such as N, N'-dimethyl urea or N, N'-dibenzyl urea in the presence of formaldehyde under conditions pioneered by Knapp, et al.[2] to afford either the dimethyl ($R=CH_3$) or the dibenzyl ($R=CH_2Ph$) triazone derivative 47. Triazone 47 can be deprotonated with a base such as n-butyllithium, lithium diisopropylamide (LDA), or Lithium bis(trimethylsilyl)amide in a solvent such as DMF or mixtures of DMF and THE at temperatures in the range of −78° to −40° C. to give a lithiated derivative which is directly treated with commercially available (R)-(-)-glycidyl butyrate. The resulting mixture is then warmed to ambient temperature to afford the (hydroxymethyl)oxazolidinone 48.

Chart XIX describes the conversion of triazone derivative 48 to compounds of structural Formula v. As shown, triazone derivative 48 can be converted to (acylaminomethyl) oxazolidinone 49 by means identical with those used to convert compound 8 to 13 in Chart XII. The triazone group of 49 can be removed by hydrolysis with aqueous hydrochloric acid solution or treatment with hot saturated ammonium chloride solution to afford amine 50. Amine 50 can then be converted into a number of carbonyl derivatives 51 (R=optionally substituted alkyl, alkoxy, alkylamino, etc.) by treatment with various carbonyl derivatives, such as acyl chlorides, anhydrides, alkyl and aryl chloroformates, isocyanates, and the like, using appropriate bases and catalysts, in suitable solvents known to one skilled in the art. In addition, amine 50 can be converted into a number of alkyl derivatives 52 (R=optionally substituted straight or branched chain alkyl) by treatment of 50 with an appropriate aldehyde or ketone in the presence of hydrogen gas and a catalyst such as 10% palladium on carbon or a reagent such as sodium cyanoborohydride in a protic solvent such as methanol. Alternatively, 50 could be treated with an optionally substituted alkyl halide in the presence of a base such as sodium carbonate in a suitable solvent such as THF or acetonitrile, optionally in the presence of water to afford 52. Thus prepared, compounds 51 and 52 constitute examples of oxazolidinone antibacterial agents of structural Formula v, where n=1.

It will be apparent to those skilled in the art that the described synthetic procedures are merely representative in nature and that alternative synthetic processes are known, for example some of those described in the cited references.

Examples of pyrrolidinyl-phenyloxazolidinones that can be prepared as part of this invention are as follows:

1. (S)-N-[[3-[3-Fluoro-4-(3-oxopyrrolidinyl)phenyl]-2-oxo-5-oxazolidinyl]methyl]acetamide
2. (S)-N-[[3-[3-Fluoro-4-(3-oxo-4-methylpyrrolidinyl) phenyl]-2-oxo-5-oxazolidinyl]methyl]acetamide
3. (S)-N-[[3-[3-Fluoro-4-(2,4-dimethyl-3-oxopyrrolidinyl)phenyl]-2-oxo-5-oxazolidinyl]methyl] acetamide
4. (S)-N-[[3-[3-Fluoro-4-(2,2-dimethyl-3-oxopyrrolidinyl)phenyl]-2-oxo-5-oxazolidinyl]methyl] acetamide
5. (S)-N-[[3-[3-Fluoro-4-(4,4-dimethyl-3-oxopyrrolidinyl)phenyl]-2-oxo-5-oxazolidinyl]methyl] acetamide
6. (S)-N-[[3-[3-Fluoro-4-(2,4-dimethyl-3-oxopyrrolidinyl)phenyl]-2-oxo-5-oxazolidinyl]methyl] acetamide
7. (S)-N-[[3-[3-Fluoro-4-(3-isonitrosopyrrolidinyl) phenyl]-2oxo-5-oxazolidinyl]methyl]acetamide
8. (S)-N-[[3-[3-Fluoro-4-(O-methyl-3-isonitrosopyrrolidinyl)phenyl]-2-oxo-5-oxazolidinyl] methyl]acetamide
9. (S)-N-[[3-[3-Fluoro-4-(3-hydroxypyrrolidinyl)phenyl] -2-oxo-5-oxazolidinyl]methyl]acetamide
10. (S)-N-[[3-[3-Fluoro-4-(cis-3-hydroxy-4-methylpyrrolidinyl)phenyl]-2-oxo-5-oxazolidinyl] methyl]acetamide
11. (S)-N-[[3-[3-Fluoro-4-(trans-3-hydroxy-4-methylpyrrolidinyl)phenyl]-2-oxo-5-oxazolidinyl] methyl]acetamide
12. (S)-N-[[3-[3-Fluoro-4-(3-methoxypyrrolidinyl) phenyl]-2-oxo-5-oxazolidinyl]methyl]acetamide
13. (S)-N-[[3-[3-Fluoro-4-(cis-3,4-dihydroxypyrrolidinyl)phenyl]-2-oxo-5-oxazolidinyl] methyl]acetamide
14. (S)-N-[[3-[3-Fluoro-4-(trans-3,4-dihydroxypyrrolidinyl)phenyl]-2-oxo-5-oxazolidinyl] methyl]acetamide
15. (S)-N-[[3-[3-Fluoro-4-(3hydroxyacetylamino) pyrrolidinyl)phenyl]-2-oxo-5-oxazolidinyl]methyl] acetamide
16. (S)-N-[[3-[3-Fluoro-4-[3-(phenylmethoxyacetylamino)pyrrolidinyl]phenyl]-2-oxo-5-oxazolidinyl]methyl]acetamide
17. (S)-N-[[3-[3-Fluoro-4-(3-(methoxyacetylamino) pyrrolidinyl)phenyl]-2-oxo-5-oxazolidinyl]methyl] acetamide
18. (S)-N-[[3-[3-Fluoro-4-(3-(methoxycarbonylamino) pyrrolidinyl)phenyl]-2oxo-5-oxazolidinyl]methyl] acetamide
19. (S)-N-[[3-[3-Fluoro-4-(3-(ethoxycarbonylamino) pyrrolidinyl)phenyl]-2-oxo-5-oxazolidinyl]methyl] acetamide
20. (S)-N-[[3-[3-Fluoro-4-(cis-3-(phenylmethoxyacetylamino)-4-methylpyrrolidinyl) phenyl]-2-oxo-5-oxazolidinyl]methyl]acetamide
21. (S)-N-[[3-[3-Fluoro-4-(cis-3hydoxyacetylamino)-4-methylpyrrolidinyl)phenyl]-2-oxo-5-oxazolidinyl] methyl]acetamide
22. (S)-N-[[3-[3-Fluor-4-(cis-3-methoxyacetylamino)-4-methylpyrrolidinyl)-phenyl]-2-oxo-5-oxazolidinyl] methyl]acetamide
23. (S)-N-[[3-[3-Fluoro-4-(cis-3-(methoxycarbonylamino)-4-methylpyrrolidinyl)-phenyl]-2-oxo-5-oxazolidinyl]methyl]acetamide
24. (S)-N-[[3-[3-Fluoro-4-(cis-3-(ethoxycarbonylamino) 4-methylpyrrolidinyl)-phenyl]-2-oxo-5-oxazolidinyl] methyl]acetamide
25. (S)-N-[[3-[3-Fluoro-4-trans-3-(phenylmethoxyacetylamino)4-methylpyrrolidinyl) phenyl]-2oxo-5oxazolidinyl]methyl]acetamide
26. (S)-N-[[3-[3-Fluoro-4-(trans-3-(hydoxyacetylamino) 4-methylpyrrolidinyl)-phenyl]-2-oxo-5-oxazolidinyl] methyl]acetamide
27. (S)-N-[[3-[3-Fluoro-4trans-3-(methoxyacetylamino) 4-methylpyrrolidinyl)-phenyl]-2-oxo-5-oxazolidinyl] methyl]acetamide 28. (S)-N-[[3-[3-Fluoro-4-(trans-3-(methoxycarbonylamino)-4-methylpyrrolidinyl)phenyl]-2-oxo-5-oxazolidinyl]methyl]acetamide
29. (S)-N-[[3-[3-Fluoro-4-(trans-3-(ethoxycarbonylamino)-4-methylpyrrolidinyl)phenyl]-2-oxo-5-oxazolidinyl]methyl]acetamide
30. (S)-N-[[3-(3-Fluoro-4-(3-(phenylmethoxyacetylamino)methylpyrrolidinyl)-phenyl]-2-oxo-5-oxazolidinyl]methyl]acetamide
31. (S)-N-[[3-[3-Fluoro-4-(3-hydroxyacetylamino)methylpyrrolidinyl)phenyl]-2-oxo-5-oxazolidinyl]methyl]acetamide
32. (S)-N-[[3-[3-Fluoro-4-(3-(methoxyacetyamino)methylpyrrolidinyl)phenyl]-2-oxo-5-oxazolidinyl]methyl]acetamide
33. (S)-N-[[3-[3-Fluoro-4-(3-(methoxycarbonylyamino)methylpyrrolidinyl)phenyl]-2-oxo-5-oxazolidinyl]methyl]acetamide
34. (S)-N-[[3-[3-Fluoro-4-(3-(ethoxycarbonylamino)methylpyrrolidinyl)phenyl]-2-oxo-5-oxazolidinyl]methyl]acetamide
35. (S)-N-[[3-[3-Fluoro-4-(cis-3-(phenylmethoxyacetylamino)methyl-4-methylpyrrolidinyl)phenyl]-2-oxo-5-oxazolidinyl]methyl]acetamide
36. (S)-N-[[3-[3-Fluoro-4-(cis-3-(hydroxyacetylamino)methyl-4-methylpyrrolidinyl)phenyl]-2-oxo-5-oxazolidinyl]methyl]acetamide
37. (S)-N-[[3-[3-Fluoro-4-(cis-3-(methoxyacetylamino)methyl-4-methylpyrrolidinyl)phenyl]-2-oxo-5-oxazolidinyl]methyl]acetamide
38. (S)-N-[[3-[3-Fluoro-4-(cis-3-methoxycarbonylamino)methyl-4-methylpyrrolidinyl)phenyl]-2oxo-5-oxazolidinyl]methyl]acetamide
39. (S)-N-[[3-[3-Fluoro-4-(cis-3-(ethoxycarbonylamino)methyl-4-methylpyrrolidinyl)phenyl]-2-oxo-5-oxazolidinyl]methyl]acetamide
40. (S)-N-[[3-[3-Fluoro-4-(trans-3-(phenylmethoxyacetylamino)methyl-4 methylpyrrolidinyl)phenyl]-2-oxo-5-oxazolidinyl]methyl]acetamide
41. (S)-N-[[3-[3-Fluoro-4-(trans-3-(hydroxyacetylamino)methyl-4-methylpyrrolidinyl)phenyl]-2-oxo-5-oxazolidinyl]methyl]acetamide
42. (S)-N-[[3-[3-Fluoro-4-(trans-3-(methoxyacetylamino)methyl-4-methylpyrrolidinyl)phenyl]-2-oxo-5-oxazolidinyl]methyl]acetamide
43. (S)-N-[[3-[3-Fluoro-4-(trans-3-(methioxycarbonylamino)methyl-4-methylpyrrolidinyl)phenyl]-2-oxo-5-oxazolidinyl]methyl]acetamde
44. (S)-N-[[3-[3-Fluoro-4-(trans-3-(ethoxycarbonylamino)methyl-4-methylpyrrolidinyl)phenyl]-2-oxo-5-oxazolidinyl]methyl]acetamide
45. (S)-N-[[3-[3-Fluoro-4-[trans-3-(phenylmethoxy)acetylamino-4-hydroxpyrrolidinyl]phenyl]-2-oxo-5-oxazolidinyl]methyl]acetamide
46. (S)-N-[[3-(3-Fluoro-4-(trans-3-(methoxyacetyamino)-4-hydroxypyrrolidinyl)phenyl]-2-oxo-5-oxazolidinyl]methyl]acetamide
47. (S)-N-[[3-[3-Fluoro-4-(trans-3-(methoxycarbonylamino)-4-hydroxypyrrolidinyl)phenyl]-2-oxo-5-oxazolidinyl]methyl]acetamide
48. (S)-N-[[3-[3-Fluoro-4-(trans-3-(ethoxycarbonylamino)-4-hydroxypyrrolidinyl)phenyl]-2-oxo-5-oxazolidinyl]methyl]acetamide Antibacterial Activity The oxazolidinone antibacterial agents of this invention have useful activity against a variety of organisms. The in vitro activity of compounds of this invention can be assessed by standard testing procedures such as the determination of minimum inhibitory concentration (MIC) by agar dilution as described in "Methods for Dilution Antimicrobial Susceptibility Tests for Bacteria That Grow Aerobically" (MFT) published January 1983 by the National Committee for Clinical Laboratory Standards, 771 East Lancaster Avenue, Villanova, Pa. 19084, USA. The activity of selected compounds of this invention against *Staphylococcus aureus* and *Streptococcus pneumoniae* are shown in Table 1.

TABLE 1

| | Minimum Inhibitory Concentration ($\mu$g/mL) | |
|---|---|---|
| Example No. | S. aureus UC ® 9213 | S. pneumoniae UC ® 9912 |
| 1 | 4 | 2 |
| 2 | 4 | 2 |
| 3 | 16 | 8 |
| 4 | 1 | 0.5 |
| 5 | 4 | 1 |
| 6 | 8 | 4 |
| 7 | 8 | 2 |
| 8 | 32 | 8 |
| 9 | 8 | 2 |
| 10 | 2 | 1 |
| 11 | 4 | 2 |
| 12 | 8 | 2 |
| 13 | 16 | 2 |
| 14 | 4 | 1 |
| 15 | 16 | 2 |
| 16 | 8 | 1 |
| vancomycin | 1 | 0.5 |

Azetindinyl-Phenyloxazolidinones

EXAMPLE 1

(S)-N-[[3-[3-fluoro-4-(3-methoxy-1-azetidinyl)phenyl-2-oxo-5-oxazolidinyl]methyl]acetamide Step1: 1-(diphenylmethyl)-3-methoxyazetidine A slurry of sodium hydride (0.440 g of a 60% dispersion in oil, 11.0 mmol) in dry tetrahydrofuran (125 mL) under nitrogen was cooled with an ice bath to 0° C. and treated with solid 1-(diphenylmethyl)-3-azetidinol (2.393 g, 10.0 mmol) over 5 min. After stirring 30 min at 0° C., iodomethane (1.490 g, 0.654 mL, 10.5 mmol) was added. When the addition was completed, the cooling bath was removed and the reaction mixture allowed to warm to ambient temperature overnight. The reaction mixture was poured into pH 7 phosphate buffer and extracted with ethyl acetate. The combined organic extracts were washed with brine, dried over sodium sulfate, filtered and concentrated under reduced pressure. The crude product was chromatographed over silica gel (300 mL) packed with dichloromethane, eluting with a gradient of 1–10% ethyl acetate/dichloromethane. Concentration of appropriate fractions afforded 2.081 g (82%) of the title compound as a pale yellow syrup with MS(EI) 253 (M+).

Step 2: 3-fluoro-4-(3-methoxy-1-azetidinyl)nitrobenzene

A solution of 1-diphenylmethyl)-3-methoxyazetidine (2.000 g, 7.91 mmol) in 25% tetrahydrofuran/ethanol (100 mL) was treated with 5N HCl (5.0 mL) and palladium hydroxide on carbon (Pearlman's catalyst, 0.500 g). The mixture was shaken on a Parr apparatus under 45 psi of $H_2$. After 16 h some starting material still remained by TLC analysis (silica gel, 6% acetonitrile/chloroform). An additional 0.500 g of Pearlman's catalyst was added and the hydrogenolysis continued a further 16 h, at which time the reaction appeared to be complete. The reaction mixture was filtered through Celite® and the filtrate concentrated under reduced pressure to an amber oil. This material was dissolved in dimethyl sulfoxide (30 mL) and treated with dipotassium hydrogen phosphate (6.88 g, 39.6 mmol) and 3,4-difluoronitrobenzene (1.05 mL, 9.49 mmol). The reaction mixture was stirred at ambient temperature for 16 h, at which time TLC analysis (silica gel, 6% acetonitrile/chloroform) revealed the reaction to be complete. The reaction mixture was diluted with water (150 mL) and extracted with chloroform (3×40 mL). The combined organic extracts were washed with water (3×25 mL) and brine, dried over sodium sulfate, filtered and concentrated in vacuo to give a crude product. Purification was accomplished by chromatography over silica gel (100 g), eluting with a gradient of 0–1% acetonitrile/chloroform. Concentration of appropriate fractions then afforded 1.50 g (84%) of the title compound as a bright yellow solid with mp 57.5°–58° C. and MS(EI) 226 (M+).

Step 3: N-(carbobenzyloxy)-3-fluoro-4-(3-methoxy-1-azetidinyl)aniline

A solution of 3-fluoro-4-(3-methoxy-1-azetidinyl) nitrobenzene (1.50 g, 6.64 mmol) in 1:1 methanol/tetrahydrofuran (35 mL) was treated with 10% palladium on carbon and then ammonium formate (1.26 g, 19.9 mmol) at room temperature. After 20 min the color of the reaction mixture changed from yellow to colorless. The reaction mixture was filtered through Celite® and the filtrate concentrated under reduced pressure. The recovered oil was immediately dissolved in 3:1 acetone/water (25 mL) and treated with potassium carbonate (2.75 g, 19,9 mmol) and benzyl chloroformate (1.31 mL, 8.30 mmol). After 30 min TLC analysis (6% acetonitrile/chloroform) revealed the reaction to be complete. The reaction mixture was extracted with chloroform (3×20 mL). The combined organic extracts were washed with brine, dried over sodium sulfate, filtered and concentrated in vacuo to a purple oil. This material was chromatographed over silica gel (100 g), eluting with a gradient of 1–3% acetonitrile/chloroform, to give, after concentration of appropriate fractions, 1.24 g (56%) of the title compound as an off-white solid with mp 95°–96.5° C. and MS(EI) 330 (M+).

Step 4: (R)-[3-[3-fluoro-4-(3-methoxy-1-azetidinyl)phenyl]-2-oxo-5-oxazolidinyl]methanol A solution of N-(carbobenzyloxy)-3-fluoro-4-(3-methoxy-1-azetidinyl)aniline (0.865 g, 2.62 mmol) in dry tetrahydrofuran (10 mL) was cooled to −78° C. under a nitrogen atmosphere and treated with n-butyllithium (1.65 mL of a 1.6M solution in hexanes, 2.65 mmol). After stirring at −78°0 C. for 15 min, the reaction mixture was treated with (R)-glycidyl butyrate (0.374 mL, 2.65 mmol). The cooling bath was then removed and the reaction mixture allowed to warm to ambient temperature. After 1 h the reaction was judged complete by TLC analysis. The reaction mixture was quenched by the addition of saturated aqueous ammonium chloride (0.5 mL) and concentrated under reduced pressure to a yellow solid. Chromatography over silica gel (10 g), eluting with a gradient of 1–2% methanol/chloroform afforded, after concentration of appropriate fractions, 0.530 g (68%) of the title compound as an off-white solid with mp 131°–132° C. and MS(EI) 296 (M+).

Step 5: (R)-[[3-[3-fluoro-4-(3-metho-1-azetidinylphenyl]-2-oxo-5-oxazolidinyl]methyl]methanesulfonate A solution of (R)-[3-[3-fluoro-4-(3-methoxy-1-azetidinyl)phenyl]-2-oxo-5-oxazolidinyl]methanol (0.492 g, 1.66 mmol) in dry dichloromethane (25 mL) under a nitrogen atmosphere was cooled with an ice bath to 0° C. and treated with triethylamine (0.254 mL, 1.83 mmol) and then methanesulfonyl chloride (0.141 mL, 1.83 mmol). After 1 h at 0° C., TLC analysis (10% methanol/chloroform) revealed the reaction to be complete. The reaction mixture was washed with water and brine, dried over sodium sulfate, filtered and concentrated in vacuo to a white solid. Chromatography over silica gel (100 g), eluting with a gradient of 1–3% methanol/chloroform afforded, after concentration of appropriate fractions, 0.601 g (97%) of the title compound as a white solid with mp 122.5°–123.5° C. and MS(EI) 374 (M+).

Step 6: (R)-[[3-[3-fluoro-4-(3-methoxy-1-azetidinyl)phenyl]-2-oxo-5-oxazolidinyl]methyl]azide (R)-[[3-[3-fluoro-4-(3-methoxy-1-azetidinyl)phenyl]-2-oxo-5-oxazolidinyl]methyl]methanesulfonate (0.508 g, 1.36 mmol) was combined with sodium azide (0.106 g, 1.63 mmol) in N,N-dimethylformamide (4 mL). The reaction mixture was heated to 65° C. under a nitrogen atmosphere. After 2 hours, a small amount of the starting mesylate still remained by TLC analysis (5% methanol/chloroform). An additional 0.044 g of sodium azide was added and the reaction heated for a further 1.5 h, at which time TLC revealed the reaction to be complete. The reaction mixture was filtered and concentrated in vacuo. The residue was chromatographed over silica gel (25 g), eluting with a gradient of 1–3% methanol/chloroform. Appropriate fractions were combined and concentrated in vacuo to furnish 0.426 g (98%) of the title compound as an off-white solid. An analytical sample was prepared by recrystallization of this material from 3:1 ethyl acetate/hexane to give a white solid with mp 111°–112.5° C. and MS(EI) 321 (M+).

Step 7: (S)-N-[[3-[3-fluoro-4-(3-methoxy-1-azetidinyl)phenyl]-2-oxo-5-oxazolidinyl]methyl]acetamide A solution of (R)-[[3-[3-fluoro-4-(3-methoxy-1-azetidinyl)phenyl]-2oxo-5-oxazolidinyl]methyl]azide (0.393 g, 1.22 mmol) in 5:1 methanol/dichloromethane (20 mL) was treated with 10% palladium on carbon (0.030 g) under a nitrogen stream. The atmosphere was then replaced with hydrogen (balloon). After stirring 3 hours under hydrogen, the reduction was judged to be complete by TLC analysis (5% methanol/chloroform). The reaction mixture was filtered through Celite® and concentrated under reduced pressure. The crude 5-(aminomethyl)oxazolidinone was dissolved in dichloromethane (15 mL) and treated with pyridine (0.118 mL, 1.46 mmol) and acetic anhydride (0.138 mL, 1.46 mmol) under a nitrogen atmosphere at ambient temperature. After 2 h, the reaction was judged to be complete by TLC. The reaction mixture was washed with water and brine, dried over sodium sulfate, filtered and concentrated under reduced pressure. Chromatography over silica gel (50 g), eluting with a gradient of 1–3% methanol/chloroform, afforded, after concentration of appropriate fractions, 0.281 g (68%) of the title antibacterial agent as a white solid. An analytical sample, prepared by recrystallization from 2:1 ethyl acetate/hexane, was a white solid with mp 160°–161.5° C. and MS(EI) 337 (M+).

EXAMPLE 2

(S)-N-[[3-[3-fluoro-4-3-hydroxy-1-azetidinyl)phenyl]-2-oxo-5-oxazolidinyl]methyl]acetamide Step 1: 3-fluoro-4-(3-hydroxy-1-azetidinyl)nitrobenzene 1-(Diphenylmethyl)-3-azetidinol hydrochloride (2.000 g, 7.29 mmol) was dissolved in methanol (75 mL) and treated with 6N HCl (1.20 mL, 7.29 mmol). Palladium hydroxide on carbon (0.200 g) was then added under a nitrogen stream. The reaction mixture was then shaken on a Parr apparatus under 40 psi of $H_2$. After 16 h, TLC analysis (5% methanol/chloroform) revealed the starting material was consumed. The reaction mixture was filtered through Celite® and concentrated under reduced pressure to an amber oil. This material was dissolved in dimethylsulfoxide (29 mL) and the atmosphere replaced with nitrogen. Dipotassium hydrogen phosphate (5.07 g, 29.2 mmol) was added followed by 3,4-difluoronitrobenzene (0.966 mL, 8.75 mmol). The mixture was stirred at ambient temperature under nitrogen. After 3 h, TLC analysis (5% methanol/chloroform) revealed the reaction to be complete. The reaction mixture was diluted with water (250 mL) and extracted with chloroform (4×50 mL). The combined organic extracts were washed with water (2×50 mL) and brine, dried over sodium sulfate, filtered and concentrated in vacuo to give a yellow solid. Chromatography over silica gel (100 g), eluting with a gradient of 3–7% acetonitrile/chloroform afforded, after concentration of appropriate fractions, 1.00 g (65%) of the title compound as an orange solid with mp 130.5°–132° C. and MS(EI) 212 (M$^+$).

Step 2: 4-[3-[(tert-butyldimethylsilyl)oxy]-1-azetidinyl]-3-fluoronitrobenzene

A solution of 3-fluoro-4-(3-hydroxy-1-azetidinyl) nitrobenzene (5.51 g, 26.0 mmol) in N,N-dimethylformamide (104 mL) under nitrogen was cooled to 0° C. with an ice bath and treated with imidazole (1.86 g, 27.3 mmol) and then tert-butyldimethylsilyl chloride (4.12 g, 27.3 mmol). The reaction mixture was stirred at 0° C. for 30 min and then at room temperature overnight. TLC analysis (5% methanol/chloroform) at this time revealed a small amount of starting material still remained. An additional amount of tert-butyldimethylsilyl chloride (0.392 g) was added. After stirring overnight, TLC analysis indicated the reaction was complete. The reaction mixture was diluted with water (500 mL) and extracted with dichloromethane (4×70 mL). The combined organic extracts were washed with water and brine, dried over sodium sulfate, filtered and concentrated under reduced pressure to a yellow solid. Chromatography over silica gel (200 g), eluting with 5% and 10% ethyl acetate/hexane, afforded, after concentration of appropriate fractions, 6.30 g (74%) of the title compound as a yellow solid with mp 98.5°–99.5° C. and MS(EI) 326 (M$^+$).

Step 3: N-(carbobenzyloxy)-4-[3-[(tert-butyldimethylsilyl) oxy]-1-azetidinyl]-3-fluoroaniline 4-[3-[(tert-Butyldimethylsilyl)oxy]-1-azetidinyl]-3-fluoronitrobenzene (1.00 g, 3.07 mmol) was combined with 10% palladium on carbon (0.100 g) in 3:1 tetrahydrofuran/water (25 mL) under a nitrogen atmosphere. The atmosphere was replaced with hydrogen (balloon) by repeated evacuation and filling. After 2 h the initial yellow color of the reaction solution disappeared and TLC analysis (15% ethyl acetate/hexane) revealed the reduction to be complete. The reaction mixture was filtered through Celite® and the filtrate immediately placed under a nitrogen atmosphere and treated with sodium bicarbonate (1.41 g, 16.8 mmol) and benzyl chloroformate (0.528 mL, 3.69 mmol). After 30 min at ambient temperature, TLC analysis (15% ethyl acetate/hexane) indicated the reaction was complete. The reaction mixture was concentrated under reduced pressure to an off-white solid. Cromatography over silica gel (125 g), eluting with a gradient of 5–30% ethyl acetate/hexane, afforded, after concentration of appropriate fractions, 0.565 g (43%) of the title compound as a white solid with mp 91°–93° C. and MS(EI) 430 (M$^+$).

Step 4: (R)-[3-[4-[3-[(tert-butyldimethylsilyl)oxy]1-azetidinyl]-3-fluorophenyl]-2oxo-5-oxazolidinyl]methanol A solution of N-(carbobenzyloxy)-4-[3-[(tert-butyldimethylsilyl)oxy]-1-azetidinyl]-3-fluoroaniline (6.30 g, 14.7 mmol) in dry tetrahydrofuran (100 mL) under a nitrogen atmosphere was cooled to −78° C. and treated with n-butyllithium (9.16 mL of a 1.6M solution in hexanes, 14.7 mmol). When the addition was complete, the reaction mixture was stirred at −78° C. for 15 min and then treated with (R)-glycidyl butyrate (2.21 mL, 14.7 mmol). After completion of the addition, the cooling bath was removed and the reaction mixture allowed to stir at ambient temperature for 1.5 h. After this time, saturated aqueous ammonium chloride (20 mL) was added. After 3 min, saturated aqueous sodium bicarbonate (10 mL) was added to the reaction mixture and the organic solvent removed by rotary evaporation under reduced pressure. Dichloromethane (100 mL) was added and the mixture washed with water and brine. The organic layer was dried over sodium sulfate, filtered and concentrated in vacuo. Chromatography over silica gel (200 g), eluting with a gradient of 1–3% methanol/chloroform, afforded, after concentration of appropriate fractions, 4.39 g (75%) of the title compound as an off-white solid with mp 183°–186° C. and MS(EI) 396 (M$^+$).

Step 5: (R)-[[3-[4-[3-[(tert-butyldimethylsilyl)oxy]-1-azetidinyl]-3-fluorophenyl]-2-oxo-5-oxazolidinyl]methyl] methanesulfonate Crude (R)-[3-[4-[3-[(tert-butyldimethylsilyl)oxy]-1-azetidinyl]-3-fluorophenyl]-2-oxo-5-oxazolidinyl]methanol (5.38 g, 13.6 mmol) was dissolved in dry dichloromethane (70 mL), cooled to 0° C. with an ice bath, and treated with triethylamine (2.08 mL, 14.9 mmol) and then methanesulfonyl chloride (1.15 mL, 14.9 mmol). After 30 min at 0° C., the reaction was complete by TLC analysis (5% methanollchloroformn). The reaction mixture was washed with saturated aqueous sodium bicarbonate, water and brine, dried over sodium sulfate, filtered and concentrated under reduced pressure to an off-white solid. An analytical sample, prepared by triturating the crude product with isopropanol and diethyl ether, followed by filtration and drying in vacuo, afforded an off-white solid with mp 142°–145° C. and MS(EI) 474 (M$^+$).

Step 6: (R)-[[3-[4-[3-[(tert-butyldimethylsilyl)oxy]-1-azetidinyl]-3-fluorophenyl]-2-oxo-5-oxazolidinyl]methyl] azide Crude (R)-[[3-[4-[3-[(tert-butyldimethylsilyl)oxy]-1-azetidinyl]-3-fluorophenyl]-2-oxo-5-oxazolidinyl]methyl] methanesulfonate (9.42 mmol) was dissolved in dry N,N-dimethylformamide (50 mL) and treated with sodium azide (4.42 g, 68.0 mmol) at ambient temperature. The reaction mixture was warmed to 65° C. under nitrogen for 4 h. TLC analysis (5% methanol/chloroform) at this time revealed the reaction to be complete. The reaction mire was diluted with ethyl acetate (100 mL) and washed with water (3×25 mL) and brine, dried over sodium sulfate, filtered and concentrated in vacuo to an amber solid. Chromatography over silica gel (125 g), eluting with a gradient of 10–20% ethyl acetate/hexane, afforded, after concentration of appropriate fractions, 2.21 g (56% for 3 steps) of the title azide as a white solid with mp 121°–122.5° C. and MS(EI) 421 (M$^+$).

Step 7: (S)-N-[[3-[4-[3-[(tert-butyldimethylsilyl)oxy]-1-azetidinyl]-3-fluorophenyl]-2-oxo-5-oxazolidinyl]methyl] acetamide A solution of (R)-[[3-[4-[3-[(tert-butyldimethylsilyl)oxy] -1-azetidinyl]-3-fluorophenyl]-2-oxo-5-oxazolidinyl] methyl]azide (2.04 g, 4.85 mmol) in 1:1 ethyl acetate/methanol (200 mL) was treated with 10% palladium on carbon (0.300 g) under a nitrogen stream. The atmosphere was then replaced with H$_2$ (balloon) by repeated evacuation and filling. After 3 h, TLC analysis (5% methanol/chloroform) revealed the reduction to be complete. The reaction mixture was filtered through Celite® and the filtrate concentrated under reduced pressure to a white solid. The crude 5-(aminomethyl)oxazolidinone was dissolved in dichloromethane (100 mL), cooled to 0° C. under a nitrogen atmosphere, and treated with pyridine (0.431 mL, 5.33 mmol) and acetic anhydride (0.503 mL, 5.33 mmol). After 30 min at 0° C., the acetylation was complete by TLC (5% methanol/chloroform). The reaction mixture was washed with water and brine, dried over sodium sulfate, filtered and concentrated in vacuo to give the crude product as a tan solid. Chromatography over silica gel (125 g), eluting with a gradient of 1–3% methanol/chloroform, afforded, after concentration of appropriate fractions, 1.77 g (84%) of the title compound as a white solid with mp 183.5°–184° C. and MS(EI) 437 (M+).

Step 8: (S)-N-[[3-[3-fluoro-4-(3-hydroxy-1-azetidinyl) phenyl]-2-oxo-5-oxazolidinyl]methyl]acetamide An acetonitrile (55 mL) solution of (S)-N-[[3-[4-[3-[(tert-butyldimethylsilyl)oxy]-1-azetidinyl]-3-fluorophenyl]-2-oxo-5-oxazolidinyl]methyl]acetamide (1.23 g, 2.81 mmol) in a polypropylene bottle was treated with 38% aqueous hydrofluoric acid (15 mL) at ambient temperature. TLC analysis revealed the deprotection to be complete after 3 h. The reaction mixture was diluted with water (15 mL) and neutralized with solid sodium bicarbonate. Additional water was added (50 mL) and the mixture extracted with chloroform. The combined organic extracts were washed with water and brine, dried over sodium sulfate, filtered and concentrated in vacuo to give the title oxazolidinone antibacterial agent as an off-white solid with mp 174°–177° C. and MS(EI) 323 (M+).

EXAMPLE 3

(S)-N-[[3-[3-fluoro-4-[3-[N(2-fluoroethyl)N-methylamino]-1-azetidinyl]phenyl]-2-oxo-5-oxazolidinyl]methyl]acetamide Step 1: 1-Diphenlmethyl)-3-[N-2-fluoroethyl)-N-methylamino]azetidine 1-(Diphenylmethyl)-3-methylamino)azetidine (5.00 g, 19.8 mmol) was combined with potassium carbonate (16.4 g, 119 mmol) and 2-fluoroethyl tosylate (6.50 g, 29.8 mmol) in 6% water/acetonitrile (200 mL). The mixture was heated to reflux temperature under a nitrogen atmosphere. After 3 h at reflux, TLC analysis (5% methanol/chloroform) revealed a small amount of starting material remained. An additional 1.8 g of 2-fluoroethyl tosylate was added and the reaction mixture refluxed a further 2 h. The reaction mixture was cooled to ambient temperature and concentrated under reduced pressure. Chromatography over silica gel (200 g), eluting with a gradient of 1–5% acetonitrile/chloroform, afforded, after concentration of appropriate fractions, 4.07 g (69%) of the title compound as an amber syrup with IR 1598, 1452, 1362, 1029 cm$^{-1}$.

Step 2: 3-fluoro-4-[3-[N-(2-fluoroethyl)-N-methylaminol-1-azetidinyl]nitrobenzene A Parr bottle was charged with 1-(Diphenylmethyl)-3-[N-(2-fluoroethyl)-N-methylamino]azetidine (3.88 g, 13.0 mmol) and 25% tetrahydrofuran/ethanol (130 mL). Palladium hydroxide on carbon (1.9 g) was then added under a nitrogen stream. The mixture was then shaken on a Parr apparatus under 45 psi of $H_2$. After 20 hours, TLC analysis (5% methanol/chloroform) reavealed the hydrogenolysis to be complete. The reaction mixture was filtered through Celite® and concentrated under reduced pressure to a colorless oil. This material was dissolved in dimethyl sulfoxide (50 mL) and treated with dipotassium hydrogen phosphate (13.6 g, 78.0 mmol) followed by 3,4-difluoronitrobenzene (1.72 mL, 15.6 mmol). The reaction mixture was then stirred at ambient temperature and reaction progress monitored by TLC analysis (5% methanol/chloroform). After 4 hours, the reaction mixture was added to $H_2O$ (500 mL) and extracted with dichloromethane (4×75 mL). The combined organic extracts were washed with water and brine, dried over sodium sulfate, filtered and concentrated in vacuo to a yellow syrup. Chromatography over silica gel (200 g), eluting with a gradient 0–2.5% acetonitrile/dichloromethane, afforded, after concentration of appropriate fractions, 2.87 g (81%) of the title compound as a yellow solid with mp 46.5°–48° C. and MS(FAB) 272 (M+H)+.

Step 3: N-(carbobenzyloxy)-3-fluoro-4-[3-[N-2-fluoroethyl) -N-methylamino]1-1-azetidinyl]aniline A solution of 3-fluoro-4-[3-[N-2-fluoroethyl)-N-methylamino]-1-azetidinyl]nitrobenzene (2.66 g, 9.82 mmol) in 2:1 tetrahydrofuran/water (50 mL) and acetic acid (2.0 mL) was treated with 10% palladium/carbon under a nitrogen stream. The atmosphere was replaced with $H_2$ (balloon) by repeated evacuation and filling and the reaction mixture stirred under $H_2$ overnight. TLC analysis (6% acetonitrile/chloroform) at this time revealed the reduction to be complete. The reaction mixture was filtered through Celite®. Exposure to air was minimized since a purple color rapidly developed under these conditions. The filtrate was cooled with an ice bath to ca. 0° C. and treated with potassium carbonate (6.8 g, 49 mmol) and benzylchloroformate (1.63 mL, 10.3 mmol). The reaction mixture was stirred at ca. 0° C. for 1 h and then warmed to room temperature over 30 min. TLC analysis (6% acetonitrile/ chloroform) at this time revealed the reaction to be complete. The reaction mixture was diluted with water (200 mL) and extracted with chloroform (3×75 mL). The combined organic extracts were washed with water and brine, dried over sodium sulfate, filtered and concentrated in vacuo to a dark amber syrup. Chromatography over silica gel (200 g), eluting with a gradient of 1–3% methanol/chloroform, afforded, after concentration of appropriate fractions, 3.71 g (100%) of the title compound as an amber syrup. An analytical sample was prepared by an additional chromatographic purification to give a light amber solid with mp 57°–59° C. and MS(EI) 375 (M+).

Step 4: (R)-N-[3-[3-fluoro-4-[3-[N-(2-fluoroethyl)-N-methylaminol-1-azetidinyl]phenyl]-2-oxo-5-oxazolidinyl] methanol A solution of N-(carbobenzyloxy)-3-fluoro-4-[3-[N-(2-fluoroethyl)-N-methylamino]-1-azetidinyl]aniline (3.38 g, 9.01 mmol) in dry tetrahydrofuran (40 mL) under nitrogen was cooled to −78° C. and treated with n-butyllithium (5.69 mL of a 1.6M solution in hexane, 9.10 mmol). The reaction mixture was warmed to −40° C. and then recooled to −78° C. and treated with (R)-glycidyl butyrate (1.29 mL, 9.10 mmol). When the addition was completed, the reaction mixture was allowed to warm to ambient temperature. After 1 h, the reaction appeared to be complete by TLC analysis (5% methanol/chloroform). The reaction mixture was quenched with saturated aqueous ammonium chloride (1 mL), diluted with water (100 mL), and extracted with chloroform (3×50 mL). The combined organic extracts were washed with water and brine, dried over sodium sulfate, filtered and concentrated under reduced pressure to an amber syrup. Chromatography over silica gel (200 g), eluting with a gradient of 1–4% methanol/chloroform, afforded, after concentration of appropriate fractions, 1.69 g (55%) of the title compound as an off-white solid with mp 124°–125° C. and MS(EI) 341 (M+).

Step 5: (R)-[[3-[4-[3-[N-(2-fluoroethyl)-N-methylamino]-1-azetidinyl]-3-fluorophenyl]-2-oxo-5-oxazolidinyl]methyl] methanesulfonate A solution of (R)-N-[3-[3-fluoro-4-[3-[N-(2-fluoroethyl) -N-methylamino]-1-azetidinyl]phenyl]-2-oxo-5-oxazolidinyl]methanol (1.40 g, 4.11 mmol) in dry dichloromethane (16 mL) was treated with triethylamine (0.628 mL, 4.52 mmol) and then cooled to 0° C. under a nitrogen atmosphere. Methanesulfonyl chloride (0.348 30 mL, 4.52 mmol) was then added and the mixtue stirred at 0° C. TLC analysis (5% methanol/chloroform) after 2 h revealed a small amount of starting material still remained. An additional portion of methanesulfonyl chloride (0.100 mL, 1.30 mmol) was added and the reaction continued a further 1 h at 0° C. The reaction mixture was washed with saturated aqueous sodium bicarbonate, dried over sodium sulfate, filtered and concentrated in vacuo to give 1.88 g (100%) of the title compound as a light orange solid. $^1$H NMR analysis indicated this material was of high quality. An analytical sample was prepared by chromatographing 200 mg of the crude product over silica gel (10 g), eluting with a gradient of 1–4% methanol/chloroform, to afford, after concentration of appropriate fractions, 99 mg of the title compound as an off-white solid with mp 96.5°–98° C. and MS(EI) 419 (M$^+$).

Step 6: (R)-[[3-[4-[3-[N-(2-fluoroethyl)-N-methylamino]-1-azetidinyl]-3-fluorophenyl]-2-oxo-5-oxazolidinyl]methyl] azide A solution of (R)-[[3-[4-[3-[N-(2-fluoroethyl)-N-methylamino]-1-azetidinyl]-3-fluorophenyl]-2-oxo-5-oxazolidinyl]methyl]methanesulfonate (1.65 g, 3.94 mmol) in dry N,N-dimethylformamide (15 mL) was treated with solid sodium azide (0.768 g, 11.8 mmol). The reaction mixture was then heated to 65° C. under a nitrogen atmosphere. After 3 h, TLC analysis (5% methanol/chloroform) revealed a small amount of starting mesylate still remained. An additional portion of sodium azide (0.256 g, 3.94 mmol) was added and the reaction mixture heated at 65° C. for 1 h. The reaction mixture was cooled to ambient temperature, filtered and concentrated under reduced pressure. The residue was chromatographed over silica gel (100 g), eluting with a gradient of 1–4% methanol/chloroform, to afford, after concentration of appropriate fractions, 1.24 g (86%) of the title compound as an off-white solid with mp 60°–63° C. and MS(EI) 366 (M$^+$).

Step 7: (S)-N-[[3-[3-fluoro-4-[3-[N-(2-fluoroethyl)-N-methylamino]-1-azetidinyl]phenyl]-2oxo-5-oxazolidinyl] methyl]acetamide A solution of (R)-[[3-[4-[3-[N(2-fluoroethyl)-N-methylamnino]-1-azetidinyl]-3-fluorophenyl]-2-oxo-5-oxazolidinyl]methyl]azide (1.14 g, 3.11 mol) in methanol (20 mL) was treated with 10% palladium/carbon (0.114 g) under a nitrogen stream. The atmosphere was replaced with H$_2$ (balloon) by repeated evacuation and filling. After 2.5 h, TLC analysis (5% methanol/chloroform) revealed the reduction to be complete. The reaction mixture was filtered through Celite® and the filtrate concentrated in vacuo to an off-white solid. This material was dissolved in dichloromethane (20 mL) and treated with pyridine (0.264 mL, 3.27 mmol) and acetic anhydride (0.309 mL, 3.27 mmol) under nitrogen. After 30 min TLC analysis (5% methanol/ chloroform) indicated the acetylation to be complete. The reaction mixture was washed with water and brine, dried over sodium sulfate, filtered and concentrated under reduced pressure to give an amber oil. Chromatography over silica gel (125 g), eluting with a gradient of 1–4% methanol/ chloroform, afforded, after concentration of appropriate fractions, 0.892 g (75%) of the title oxazolidinone antibacterial agent as an off-white solid with mp 125.5°–127° C. and MIS(EI) 382 (M$^+$).

EXAMPLE 4

(S)-N-[[3-[3-fluoro-4-(3-oxo-1-azetidinyl)phenyl]-2-oxo-5-oxazolidinyl]methyl]acetamide A solution of (S)-N-[[3-[3-fluoro-4-(3-hydroxy-1-azetidinyl)phenyl]-2-oxo-5-oxazolidinyl]methyl]acetamide (EXAMPLE 2, 0.440 g, 1.36 mmol) in 10% acetonitrile/ dichloromethane (100 mL) was treated with powdered 4 angstrom molecular sieves (0.682 g), 4-methylmorpholine N-oxide (0.319 g, 2.72 mmol) and then tetra-n-propylammonium perruthenate (0.024 g, 0.068 mmol) at ambient temperature. After stirring 1.5 hours at ambient temperature, TLC analysis (10% methanol/chloroform) revealed a small amount of starting alcohol still remained. The addition of more 4-methylmorpholine N-oxide did not consume the starting material. The reaction mixture was concentrated under reduced pressure to a dark purple solid which was then chromatographed over silica gel (20 g), eluting with a gradient of 1–3.5% methanol/chloroform, to afford, after concentration of appropriate fractions, 0.204 g (47%) of the title oxazolidinone antibacterial agent as a white solid with mp 192°–193° C. and MS(EI) 321 (M$^+$).

EXAMPLE 5

(S)-N-[[3-[3-fluoro-4-[3-(methoxyimino)-1-azptidinyl] phenyl]-2-oxo-5-oxazolidinyl]methyl]acetamide A solution of (S)-N-[[3-[3-fluoro-4-(3-oxo-1-azetidinyl) phenyl]-2-oxo-5-oxazolidinyl]methyl]acetamide (EXAMPLE 4, 0.200 g, 0.623 mmol) in 5% methanol/ dichloromethane (10 mL) was treated with pyridine (0.201 mL, 2.49 mmol) and then methoxylamine hydrochloride (0.052 g, 0.623 mmol) at ambient temperature. After 1.5 hours, TLC analysis (10% methanol/chloroform) revealed the reaction to be complete. The reaction mixture was concentrated under reduced pressure to a white solid. Cromatography over silica gel (10 g), eluting with a gradient of 1–3% methanol/chloroform, afforded, after concentration of appropriate fractions, 0.204 g (94%) of the title oxazolidinone antibacterial agent as an off-white solid. Another synthetic run provided material with mp 189°–192° C. and MS(EI) 350 (M$^+$).

EXAMPLE 6

(S)-N-[[3-[3-fluoro-4-(3-methoxy-3-methyl-1-azetidinyl) phenyl]-2-oxo-5-oxazolidinyl]methyl]acetamide Step 1: 1-(diphenylmethyl)-3-methoxy-3-methylazetidine A slurry of 1-diphenylmethyl)-3-methyl-3-azetidinol hydrochloride (5.00 g, 17.2 mmol) in dry tetrahydrofuran (200 mL) was cooled with an ice bath to 0° C. and treated with sodium hydride (2.10 g of a 60% dispersion in oil, 51.8 mmol) under nitrogen. The cooling bath was removed and the mixture warmed to reflux temperature for 15 min. After cooling to room temperature, iodomethane (7.40 g, 3.22 mL, 51.8 mmol) was added. When the addition was completed, the reaction mixture was heated to reflux temperature for 15 hours. TLC analysis (9:1 hexane/ethyl acetate) revealed the methylation to be complete. The reaction mixture was quenched with saturated aqueous ammonium chloride. The mixture was transferred to a separatory funnel with ethyl acetate and water and then extracted with ethyl acetate. The combined organic extracts were washed with water and brine, dried over sodium sulfate, filtered and concentrated under reduced pressure. The crude product was chromatographed over silica gel, eluting with 9:1 ethyl acetate/ hexane. Concentration of appropriate fractions afforded 2.30 g (50%) of the title compound as a colorless oil with MS(EI) 267 (M$^+$).

Step 2: 3-fluoro-4-(3-methoxy-3-methyl-1-azetidinyl) nitrobenzene

A solution of 1-(diphenylmethyl)-3-methoxy-3-methylazetidine (2.20 g, 8.2 mmol) in 25% tetrahydrofuran/ ethanol was treated with glacial acetic acid (1.60 g, 1.50 mL, 24.7 mmol) and then palladium hydroxide on carbon (0.220 g) under a nitrogen stream. The reaction mixture was shaken on a Parr apparatus under 35 psi of H$_2$. At this time TLC analysis (9:1 hexane/ethyl acetate) revealed the reaction to be complete. The mixture was filtered through Celite® (ethyl acetate wash) and the filtrate concentrated in vacuo to give an oil. This material was dissolved in dimethyl sulfoxide (15 mL) and the solution treated with dipotassium hydrogen phosphate (8.60 g, 49.2 mmol) and 3,4-difluoronitrobenzene (1.30 g, 0.886 mL, 8.0 mmol) at ambient temperature. The yellow reaction mixture was stirred at ambient temperature under a nitrogen atmosphere for 18 hours. The reaction mixture was diluted with water and extracted with dichloromethane. The combined organic extracts were washed with water and brine, dried over sodium sulfate, filtered and dried in vacuo to give a yellow solid. Chromatography over silica gel, eluting with 8:1 hexane/ethyl acetate, afforded, after concentration of appropriate fractions, 1.80 g (90%) of the title compound as a yellow solid with mp 110°–111° C. and MS(EI) 240 (M$^+$).

Step 3: N-(carbobenzyloxy)-3-fluoro-4-(3-methoxy-3-methyl-1-azetidinyl aniline

A solution of 3-fluoro-4-(3-methoxy-3-methyl-1-azetidinyl)nitrobenzene (1.60 g, 6.7 mmol) in 25% tetrahydrofuran/methanol (35 mL) was degassed by repeated evacuation and filling with N$_2$ and then treated with 10% palladium/carbon (0.160 g). Ammonium formate (2.10 g, 33.3 mmol) was then added and the mixture degassed a final time. The reaction mixture was stirred at ambient temperature for 20 minutes, during which time the yellow reaction mixture became colorless. TLC analysis (2:1 hexane/ethyl acetate) revealed the reduction to be complete. The reaction mixture was filtered through Celite® (dichloromethane and methanol wash) and the filtrate concentrated in vacuo to give a purple gum that was immediately dissolved in 1:1 acetone/water (30 mL) under N$_2$. The mixture was cooled with an ice bath to 0° C. and treated with sodium bicarbonate (1.10 g, 13.4 mmol) and benzyl chloroformate (1.20 g, 1.00 mL, 7.37 mmol). The cooling bath was allowed to dissipate over a 3 h period. After stirring a further 2 h at ambient temperature, the reaction mixture was transferred to a separatory funnel with dichloromethane (50 mL). The organic phase was separated, washed with water, dried over sodium sulfate, filtered and concentrated in vacuo to give a purple oil. Chromatography over silica gel, eluting with 6:1 hexane/ethyl acetate, afforded, after concentration of appropriate fractions, 2.04 g (89%) of the title compound as a viscous oil which solidified on standing to a waxy solid with mp 73°–75° C. and MS(EI) 344 (M$^+$). Step 4: (R)-[3-[3-fluoro-4-(3-methoxy-3-methyl-1-azetidinyl)phenyl]-2-oxo-5-oxazolidinyl]methanol A solution of N-(carbobenzyloxy)-3-fluoro-4-(3-methoxy-3-methyl-1-azetidinyl)aniline (1.85 g, 5.4 mmol) in dry tetrahydrofuran (20 mL) was cooled to −78° C. with a dry ice/acetone bath and treated with n-butyllithium (3.50 mL of a 1.6M solution in hexane, 5.7 mmol) via syringe. After 5 min at this temperature, (R)-glycidyl butyrate (0.823 g, 0.807 mL, 5.7 mmol) was added via syringe and the reaction mixture left overnight, with gradual dissipation of the cooling bath. TLC analysis (5% methanol/chloroform) revealed the starting Cbz derivative was consumed. The reaction mixture was concentrated under reduced pressure to a waxy orange solid. The residue was dissolved in 20% methanol/dichloromethane, washed sequentially with saturated ammonium chloride, saturated sodium bicarbonate and brine. The organic layer was dried over sodium sulfate, filtered and concentrated in vacuo to give a crude product. Radial chromatography over silica gel, eluting with 2%, 3% and then 5% methanol/chloroform, afforded, after concentration of appropriate fractions, 0.811 g (48%) of the title compound as a colorless gum which was very clean by $^1$H NMR analysis. An analytical sample was prepared by recrystallization from dichloromethane/diethyl ether to give a white solid with mp 113°–114° C. and MS(EI) 310 (M$^+$).

Step 5: (R)-[[3-[3-fluoro-4-(3-methoxy-3-methyl-1-azetidinyl)phenyl]-2-oxo-5 oxazolidinyl]methyl]methanesulfonate A solution of (R)-[3-[3-fluoro-4-3-methoxy-3-methyl-1-azetidinyl)phenyl]-2-oxo-5-oxazolidinyl]methanol (0.700 g, 2.25 mmol) in dry dichloromethane (10 mL) was cooled to 0° C. with an ice bath. Triethylamine (0.250 g, 0.345 mL, 2.48 mmol) and then methanesulfonyl chloride (0.271 g, 0.183 mL, 2.37 mmol) were then added and the reaction mixture stirred under N$_2$ while the cooling bath dissipated. After 3 h TLC analysis (5% methanol/chloroform) revealed the mesylation to be essentially complete. The reaction mixture was diluted with additional dichloromethane and washed with 0.5N hydrochloric acid, saturated aqueous sodium bicarbonate and brine. The organic layer was dried over sodium sulfate, filtered and concentrated in vacuo. Radial chromatography over silica gel, eluting with 3% methanol/chloroform, afforded, after concentration of appropriate fractions, 0.022 g of recovered starting alcohol and 0.700 g (80%) of the title compound as a white solid with MS(EI) 388 (M$^+$).

Step 6: (S)-N-[[3-[3-fluoro-4-(3-methoxy-3-methyl-1-azetidinyl)phenyl]-2-oxo-5-oxazolidinyl]methyl]acetamide A mixture of (R)-[[3-[3-fluoro-4-(3-methoxy-3-methyl1-azetidinyl)phenyl]-2-oxo-5-oxazolidinyl]methyl] methanesulfonate (0.680 g, 1.75 mmol) in 2:1 ammonium hydroxide/isopropanol (30 mL) was heated to reflux (dry-ice condenser). TLC analysis (5% methanol/chloroform) after 7 hours revealed mostly starting material. The reaction was continued for an additional 46 hours. After cooling to ambient temperature, TLC indicated that the starting mesylate was essentially consumed. The reaction mixture was transferred to a separatory funnel, along with dichloromethane (100 mL), and washed with water. The organic layer was dried over sodium sulfate, filtered and concentrated in vacuo. The crude 5-(atminomethyl)oxazolidinone was dissolved in dry dichloromethane (10 mL), cooled to 0° C. with an ice bath, and treated with pyridine (0.698 g, 0.708 mL, 8.75 mmol) and acetic anhydride (0.357 g, 0.330 mL, 3.50 mmol). The cooling bath was then removed and the reaction mixture stirred at ambient temperature overnight. The reaction mixture was diluted with additional dichloromethane (60 mL) and washed with 5% aqueous hydrochloric acid, saturated aqueous sodium carbonate, water and brine. The organic layer was then dried over sodium sulfate, filtered, and concentrated in vacuo to give a crude gum. Radial chromatography over silica gel, eluting with 1%, 2% and 4% methanol/chloroform afforded, after concentration of appropriate fractions, 0.481 g (78%) of the title oxazolidinone antibacterial agent as a white foamy solid. A lyophilized sample had mp 132°–134° C. and MS(EI) 351 (M$^+$).

EXAMPLE 7

(S)-N-[[3-[3-fluoro-4-(3-hydroxy-3-methyl-1-azetidinyl) phenyl]-2 oxo-5-oxazolidinyl]methyl]acetamide Step 1: 3-fluoro-4-(3-hydroxy-3-methyl-1-azetidinyl) nitrobenzene A solution of 1-(diphenylmethyl)-3-methyl-3-azetidinol hydrochloride (3.00 g, 10.4 mmol) in 2:1 methanol/tetrahydrofuran (60 mL) was treated with triethylamine (1.00 g, 1.40 mL, 10.4 mmol) and then palladium hydroxide/carbon (0.300 g) under a N$_2$ stream. The mixture was shaken on a Parr apparatus under 40 psi H2. TLC analysis (2:1 hexane/ethyl acetate) after 2.5 h revealed the hydrogenolysis to be complete. The reaction mixture was filtered through Celite® (dichloromethane wash) and the filtrate concentrated under reduced pressure to give an oil which was immediately taken-up in dry dimethyl sulfoxide (15 mL) and treated with dipotassium hydrogen phosphate (3.40 g, 19.8 mmol) and 3,4-difluoronitrobenzene (1.60 g, 1.10 mL, 9.9 mmol) at ambient temperature under $N_2$. After stirring 16 hours at his temperature, TLC analysis (2:1 hexane/ethyl acetate) revealed the reaction to be essentially complete. The reaction mixture was transferred to a separatory funnel along with dichloromethane (100 mL) and water (150 mL). After shaking, the organic phase was separated. The aqueous phase was back-extracted with dichloromethane and the combined organic extracts washed with water, dried over sodium sulfate, filtered and concentrated in vacuo to an oil. Chromatography over silica gel, eluting with 3:1 hexane/ethyl acetate, afforded, after concentration of appropriate fractions, 2.15 g (98%) of the title compound as an orange solid with mp 109°–110° C. and MS(EI) 226 ($M^+$).

Step 2: 4-[3-[(tert-butyldimethylsilyl)oxy]-3-methyl-1-azetidinyl]-3-fluoronitrobenzene A solution of 3-fluoro-4-(3-hydroxy-3-methyl-1-azetidinyl)nitrobenzene (1.80 g, 8.0 mmol) in dry N,N-dimethylformamide (15 mL) was cooled to 0° C. with an ice bath and then treated with imidazole (0.572 g, 8.4 mmol) and tert-butyldimethylsilyl chloride (1.30 g, 8.4 mmol) under $N_2$. The reaction mixture was stirred overnight with gradual dissipation of the cooling bath. The reaction mixture was then transferred to a separatory funnel, along with water and 1:1 hexane/diethyl ether. After shaking, the layers were separated and the aqueous phase back-extracted with additional 1:1 hexane/diethyl ether. The combined organic extracts were washed with water and brine, dried over sodium sulfate, filtered and concentrated in vacuo to give an oil. Chromatography over silica gel, eluting with 3% diethyl ether/hexane and then 1:1 hexane/ethyl acetate, afforded, after concentration of appropriate fractions, 0.536 g of starting alcohol and 1.90 g (70%) of the title compound as a bright yellow solid with mp 98°–99.5° C. and MS(EI) 340 ($M^+$).

Step 3: N-(carbobenzyloxy)-4-[3-[(tert-butyldimethylsilyl)oxy]-3-methyl-1-azetidinyl]-3-fluoroaniline A solution of 4-[3-[(tert-butyldimethylsilyl)oxy]-3-methyl-1-azetidinyl]-3-fluoronitrobenzene (1.70 g, 5.0 mmol) in 2:1 methanol/tetrahydrofaran (30 mL) was degassed by repeated evacuation and filling with $N_2$ and then treated with 10% palladium/carbon (0.170 g) under $N_2$. Solid ammonium formate was added, the reaction mixture degassed a final time, and the mixture cooled with an ice bath due to the observation of an exotherm. The color of the reaction mixture changed from yellow to colorless. TLC analysis (2:1 hexane/ethyl acetate) revealed the reduction to be complete. The reaction mixture was filtered through Celite® and the filtrate concentrated in vacuo to give the intermediate aniline as a solid which was immediately dissolved in 1:1 acetone/water, cooled to 0° C. with an ice bath, and treated with sodium bicarbonate (0.840 g, 10.0 mmol) and then benzyl chloroformate (0.938 g, 0.785 mL, 5.5 mmol). The reaction mixture was left to stir overnight under $N_2$ with gradual dissipation of the cooling bath. After a total of 16 h, the reaction mixture was transferred to a separatory funnel along with dichloromethane (100 mL). After shaking, the organic phase was separated, washed with water, dried over sodium sulfate, filtered and concentrated under reduced pressure to give a crude oil. Chromatography over silica gel, eluting with 9:1 hexane/ethyl acetate, afforded, after concentration of appropriate fractions, 1.68 g (76%) of the title compound as a gum with MS(EI) 444 ($M^+$).

Step 4: (R)-[3-[4-[3-[(tert-butyldimethylsilyl)oxy]-3-methyl-1-azetidinyl]-3-fluorophenyl]-2-oxo-5-oxazolidinyl]methanol A solution of N-(carbobenzyloxy)4-[3-[(tert-butyldimethylsilyl)oxy]-3-methyl-1-azetidinyl]-3-fluoroaniline (1.60 g, 3.8 mmol) in dry tetrahydrofuran (20 mL) under $N_2$ was cooled to –78° C. with a dry ice/acetone bath and treated with n-butyllithium (2.40 mL of a 1.55M solution in hexane, 3.8 mmol) via syringe. After 5 min at this temperature, (R)-glycidyl butyrate (0.548 g, 0.538 mL, 3.8 mmol) was added. When the addition was completed, the cooling bath was removed and the reaction mixture allowed to warm to ambient temperature under $N_2$. After 2 h at this temperature, TLC analysis (2:1 hexane/ethyl acetate) revealed the starting Cbz derivative was consumed. The reaction mixture was concentrated in vacuo and the residue dissolved in ethyl acetate, washed with water and brine, dried over sodium sulfate, filtered and concentrated in vacuo to give a crude product. Chromatography over silica gel, eluting with 30% ethyl acetate/dichloromethane, afforded, after concentration of appropriate fractions, 1.10 g (71%) of the title 5-(hydroxymethyl)-oxazolidinone as a white solid with mp 143.5°–144.5° C. and MS(EI) 410 ($M^+$).

Step 5: (R)-[[3-[4-[3-[(tert-butyldimethylsilyl)oxy]-3-methyl-1-azetidinyl]-3-fluorophenyl]-2-oxo-5-oxazolidinyl]methyl]methanesulfonate A solution of (R)-[3-[4-[3-[(tert-butyldimethylsilyl)oxy]-3-methyl-1-azetidinyl]-3-fluorophenyl]-2-oxo-5-oxazolidinyl]methanol (1.00 g, 2.43 mmol) in dry dichloromethane (15 mL) was cooled to 0° C. with an ice bath and treated with triethylamine (0.295 g, 0.406 mL, 2.92 mmol) and then methanesulfonyl chloride (0.321 g, 0.217 mL, 2.80 mmol) under $N_2$. After 2 h at 0° C., TLC analysis (5% methanol/chloroform) revealed the reaction to be complete. The reaction mixture was transferred to a separatory funnel along with more dichloromethane (75 mL). The organic layer was washed with 0.5N hydrochloric acid, saturated aqueous sodium bicarbonate, water and brine, dried over sodium sulfate, filtered and concentrated in vacuo to give 1.03 g (94%) of the title compound as a white solid with mp 113°–115° C. and MS(EI) 488 ($M^+$).

Step 6: (R)-[[3-[4-[3-[(tert-butyldimethylsilyl)oxy]-3-methyl-1-azetidinyl]-3-fluorophenyl-2-oxo-5-oxazolidinyl]methyl]azide A solution of (R)-[[3-[4-[3-[(tert-butyldimethylsilyl)oxy]-3-methyl-1-azetidinyl]-3-fluorophenyl]-2-oxo-5-oxazolidinyl]methyl]methanesulfonate (0.960 g, 2.10 mmol) in dry N,N-dimethylformamide (20 mL) under $N_2$ was treated with sodium azide (0.273 g, 4.2 mmol) at ambient temperature. The reaction mixture was heated to 70° C. for 3 h and then cooled to room temperature. TLC analysis (5% methanol/chloroform) at this time revealed the reaction to be complete. The solvent was removed in vacuo and the residue taken-up in dichloromethane (100 mL) and water. The organic phase was separated, dried over sodium sulfate, filtered and concentrated in vacuo to give 0.820 g (90%) of the title compound as a white solid with mp 127°–128° C. and MS(EI) 435 ($M^+$).

Step 7: (S)-N-[[3-[4-[3-[(tert-butyldimethylsilyl)oxy]-3-methyl-1-azetidinyl]-3-fluorophenyl]-2-oxo-5-oxazolidinyl]methyl]acetamide A solution of (R)-[[3-[4-[3-[(tert-butyldimethylsilyl)oxy]-3-methyl-1-azetidinyl]-3-fluorophenyl]-2-oxo-5-oxazolidinyl]methyl]azide (0.750 g, 1.72 mmol) in ethyl acetate (20 mL) was degassed by repeated evacuation and filling with $N_2$. The solution was then treated with 10% palladium/carbon (0.075 g) under a $N_2$ stream. The atmosphere was replaced with $H_2$ (balloon) by repeated evacuation and filling and the reaction mixture stirred at ambient temperature. TLC analysis (5% methanol/chloroform) after 6 h revealed the reduction to be complete. The reaction mixture was filtered through Celite® and the filtrate concentrated under reduced pressure. The residue was dissolved in dry dichloromethane (10 mL), cooled to 0° C. with an ice bath, and treated with pyridine (0.680 g, 0.696 mL, 8.60 mmol) and acetic anhydride (0.263 g, 0.243 mL, 2.58 mmol). The cooling bath was removed and the reaction mixture stirred at ambient temperature under $N_2$. After 3 h the reaction mixture was transferred to a separatory funnel along with dichloromethane (100 mL). The mixture was washed with 10% hydrochloric acid, saturated aqueous sodium bicarbonate and brine, dried over sodium sulfate, filtered and concentrated in vacuo. Radial chromatography over silica gel, eluting with 3% and then 5% methanol/chloroform, afforded, after concentration of appropriate fractions, 0.643 g (83%) of the title compound as a white solid with mp 137°–138° C. and MS(EI) 451 ($M^+$).

Step 8: (S)-N-[[3-[3-fluoro-4-(3-hydroxy-3-methyl-1-azetidinyl)phenyl]-2-oxo-5-oxazolidinyl]methyl]acetamide A solution of (S)-N-[[3-[4-[3-[(tert-butyldimethylsilyl) oxy]-3-methyl-1-azetidinyl]-3-fluorophenyl]-2-oxo-5-oxazolidinyl]methyl]acetamide (0.550 g, 1.22 mmol) in acetonitrile (20 mL) in a polypropylene bottle was treated with 40% aqueous hydrofluoric acid (5 mL) at ambient temperature. After 16 h TLC analysis (5% methanol/chloroform) revealed the deprotection was essentially complete. The reaction mixture was transferred to an erlenmeyer flask along with some dichloromethane (150 mL). The stirred mixture was carefully treated with saturated aqueous sodium carbonate (300 mL, gas evolution). After gas evolution ceased, the mixture was transferred to a separatory funnel and the phases separated. The aqueous phase was neutralized to pH 7 by the addition of 6N hydrochloric acid and extracted with dichloromethane. The combined organic extracts were dried over sodium sulfate, filtered and concentrated in vacuo. Radial chromatography over silica gel, eluting with 5% methanol/chloroform, afforded, after concentration of appropriate fractions, 0.374 g (91%) of the title oxazolidinone antibacterial agent as a white solid with mp 152°–153° C. and MS(EI) 337 ($M^+$).

Pyrrolidinone-Phenyloxazolidinone Examples

EXAMPLE 8

(S)-N-[[3-[4-(1-Aza-5,5-dimethyl-4,6-dioxabicyclo[3.3.0] octan-1-yl)-3-fluorophenyl]-2-oxo-5-oxazolidinyl]methyl] acetamide:

3-Fluoro-1-nitro-4-(2,5-dihydropyrryl)benzene:

A solution of 2.30 g(14.47 mmol) of 2, 4-dinitrofluorobenzene and 5.04 g(28.93 mmol) of dibasic potassium phosphate in 30 mL DMSO was treated with 1.0 g(14.47 mmol) of 3-pyrroline. followed by warming at 60° C. for 24 h. The solution was cooled and diluted with 100 mL chloroform followed by extraction with water (5×75 mL). Drying ($Na_2SO_4$) and concentration in vacuo afforded a yellow solid which was recrystallized from hot ethyl acetate-hexane to afford 2.58 g(86%) of the title compound as yellow prisms, mp 132°–134° C.

3-Fluoro-1-nitro-4-(cis-3,4-dihydroxypyrrolidinyl)-benzene:

A solution of 1.25 g(6.02 mmol) of the previous compound and 881 mg(7.52 mmol) of N-methylmorpholine N-oxide in 60 mL acetone and 13 mL water was treated with 4 mL of a 2.5% osmium tetroxide solution in tert-butyl alcohol followed by stirring at ambient temperature for 24 h. The solution with 500 mg of sodium bisulfite, 2 g of magnesol, and 10 mL water followed by stirring for 20min. The mixture was filtered through celite, washing the filter cake with acetone. The filtrate was concentrated in vacuo and diluted with 100 mL ethyl acetate and 150 mL water. The aqueous layer was extracted with ethyl acetate (3×100 mL) and the combined organic layers were dried ($Na_2SO_4$) and concentrated in vacuo to afford a yellow solid. This material was recrystallized from hot acetone-hexane to afford 1.33 g(91%) of the title compound as a yellow solid, mp 151°–153° C.

1-(1-aza-5,5-dimethyl-4,6-dioxabicyclo[3.3.0]octan-1-yl) -2-fluoro-4-nitrobenzene (3):

A solution of 1.27 g(5.24 mmol) of the previous diol in 10 mL dimethylformamide was treated with 1.09 g(1.3 mL, 10.49 mmol) of 2,2-dimethoxypropane and a few crystals of p-toluenesulfonic acid, followed by stirring at ambient temperature for 24 h. The solution was diluted with 50 mL chloroform and extracted with water (5×30 mL). Drying ($Na_2SO_4$) and concentration in vacuo afforded 1.45 g(98%) of the title compound as a yellow solid, sufficiently pure for further use. An analytical sample was obtained by recrystallization from hot acetone-hexane, mp 113°–114° C.

1-(1-aza-5,5-dimethyl-4,6-dioxabicyclo[3.3.0]octan-1-yl) -2-fluoro-4-(phenylmethoxycarbonyl)aminobenzene:

A solution of 1.45 g(5.144 mmol) of the previous compound in 50 mL tetrahydrofuran was treated with 260 mg of 10% palladium on carbon followed by hydrogenation at one atmosphere for 3 h. The reaction vessel was purged with nitrogen and treated with 20 mL saturated sodium bicarbonate solution followed by cooling to 0° C. and addition of 1.75 g(1.47 mL, 10.27 mmol) of benzyl chloroformate. The solution was stirred at 0° C. for 30min followed by warming to ambient temperature for 18 h. The mixture was diluted with 50 mL ethyl acetate and 50 mL water and filtered through celite, washing the filter cake with ethyl acetate. The filtrate layers were separated and the organic phase was extracted with 50 mL water and 50 mL saturated sodium chloride solution. Drying ($Na_2SO_4$) and concentration in vacuo afforded a light purple solid which was recrystallized from hot ethyl acetate-hexane to afford 1.56 g(79%) of the title compound as fine white crystals. $^1H$ NMR($CDCl_3$): 87.39, 7.25, 6.93, 6.67, 5.19, 4.80, 3.73, 2.97, 1.53, 1.37.

(R)-[3-[4-(1-Aza-5,5-dimethyl-4,6-dioxabicyclo[3.3.0] octan-1-1-)-3-fluorophenyl]-2-oxo-5-oxazolidinyl]methanol (5):

A solution of 1.36 g(3.52 mmol) of Cbz derivative of the previous compound in 48 mL tetrahydrofuran at −78° C. was treated dropwise with 2.4 mL(1.6M, 3.87 mmol) of n-butyllithium in hexane, followed by stirring at −78° C. for 30 min. The solution was then treated with 558 mg(0.55 mL, 3.87 mmol) of neat (R)-(+)-glycidiyl butyrate, followed by warming to 0° C. for 30min and then to ambient temperature for 18 h. The solution was then cooled to 0° C. and treated with 4 mL saturated aqueous ammmonium chloride solution, followed by dilution with 200 mL dichloromethane and extraction with water (2×50 mL) and saturated ammonium chloride solution (50 mL). Drying ($Na_2SO_4$) and concentration in vacuo afforded a brown solid which was chromatographed over 80 g of 230–400 mesh silica gel, eluting with 2%(v/v) methanol in dichloromethane. These procedures afforded 840 mg of the title compound as and off-white solid. $^1H$ NMR($CDCl_3$): δ 7.34, 7.06, 6.71, 4.80, 4.75, 4.01, 3.73, 3.67, 3.56, 2.95, 1.50, 1.36. (S)-[[3-[4-(1-Aza-5,5-dimethyl-4,6-dioxabiclo[3.3.0]octan-1-yl)-3-fluorophenyl-2-oxo-5-oxazolidinyl]methyl]methanesulfonate:

A solution of 791 mg(2.25 mmol) of the previous alcohol and 283 mg(0.39 mL, 2.81 mmol) of triethylamine in 11 mL dichloromethane at 0° C. was treated with 296 mg(0.20 mL, 2.58 mmol) of methanesulfonyl chloride, followed by stirring at 0° C. for 30min. The mixture was warmed to ambient temperature and diluted with 75 ml dichloromethane followed by extraction with water (2×30 mL) and with saturated sodium bicarbonate solution (30 mL). Drying (Na$_2$SO$_4$) and concentration in vacuo afforded 810 mg(84%) of the title mesylate as an off-white solid sufficiently pure for further use. 1H NMR(CDCl$_3$): δ 7.36, 7.07, 6.73, 4.90, 4.82, 4.48, 4.41, 4.10, 3.89, 3.77, 3.10, 3.02, 1.51, 1.37.

(S)-N-[[3-[4-(1-Aza-5,5-dimethyl-4,6-dioxabicyclo[3.3.0]octan-1-yl)-3-fluorophenyl]-2-oxo-5-oxazolidinyl]methyl]acetamide:

A solution of 810 mg (1.88 mmol) of the previous mesylate in 8 mL of 1:1 tetrahydrofuran-isopropyl alcohol in a resealable thick wall tube was treated with 8 mL of ammonium hydroxide. The tube was sealed and warmed at 100° C. for 22 h. The tube was cooled and the reaction mixture was partitioned between chloroform and water. The organic layer was dried (Na$_2$SO$_4$) and concentrated in vacuo to afford 520 mg of a tan solid, which was used dissolved in 2 mL pyridine and treated with 357 mg(0.33 mL, 3.50 mmol) acetic anhydride followed by stirring at ambient temperature for 18 h. The solution was diluted with chloroform (20 mL) and extracted with water (4×20 mL). The organic layer was dried (Na$_2$SO$_4$) and concentrated in vacuo and the solid obtained recrystallized from chloroform-hexane to afford 350 mg(59%) of the title acetamide as off-white needles, mp 195°–7° C.

EXAMPLE 9

(S)-N-[[3-[4-(3,4-is-dihydroxyrrolidinyl)-3-fluorophenyl]-2-oxo-5-oxazolidinyl]methyl]acetamide (9):

A solution of 249 mg(0.63 mmol) of the compound prepared in Example 8 in 2 mL tetrahydrofuran was treated with 2 mL 2N hydrochloric acid solution, followed by stirring at ambient temperature for 18 h. The mixture was concentrated in vacuo and the residue treated with 30 mL saturated sodium bicarbonate solution. The mixture was extracted with ethyl acetate (2×50 mL), dried (Na$_2$SO$_4$) and concentrated in vacuo to afford 110 mg of an off-white solid.

This material was subjected to radial chromatography on a 2 mm chromatotron plate eluting with 7%(v/v) methanol in dichloromethane. These procedures afforded 60 mg(28%) of the title diol as a white solid, mp 183°–189° C.(decomposition).

EXAMPLE 10

(S)-N-[[3-[4-(3-hydroxypyrrolidinyl)-3-fluorophenyl]-2-oxo-5-oxazolidinyl]methyl]acetamide:
3-Fluoro-4-(3-hydroxypyrrolidinyl)nitrobenzene:

To a solution of 3-pyrrolidinol (1.82 g) and 3,4-difluoronitrobenzene (3.0 g) in dimethylformamide (30 ml) was added potassium carbonate (3.94 g). The mixture was stirred at room temperature overnight and then filtered followed by washing with dichloromethane. The filtrate combined was concentrated under reduced pressure. The residue obtained was chromatographed over a silica gel column eluting with ethyl acetate/hexane with increasing in the content of ethyl acetate (50% to 60%). The appropriate fractions were pooled and concentrated under reduced pressure to give the title compound (4.83 g); $^1$H NMR (CD$_3$OD, 270 MHz), δ 0.85 (2H, m), 2.25–2.57 (4H, m), 3.26 (1H, m), 5.47 (1H, t, J=8.6 Hz), 6.62 (1H, dd, J=2.4, 14.0 Hz), 6.69 (1H, dd, J=2.4, 8.6 Hz).

3-Fluoro-4-[3-(tert-butyldimethylsilyloxy)pyrrolidinyl]nitrobenzene

A mixture of the previous compound (4.83 g), triethylamine (9.5 ml) and dimethylaminopyridine (2.79 g) in tetrahydrofuran (100 ml) was treated with tert.-butyldimethylsilyl chloride (5.15 g) at 0° C. and stirred at room temp. for 2 days. The mixture was filtered and the insoluble material was washed with dichloromethane. The filtrate combined was washed with brine, dried over sodium sulfate and concentrated under reduced pressure. The residue obtained was chromatographed over a silica gel column eluting with ethylacetate/hexane (70/30). The appropriate fractions were combined and concentrated under reduced pressure to give the title compound (11) (6.45 g); $^1$H NMR (CDCl$_3$), δ 0.09 (6H, s), 0.88 (9H, s), 2.02 (2H, m), 3.42–3.78 (4H, m), 4.52 (1H, m), 6.53 (1H, t, J=8.9 Hz), 7.87 (1H, dd, J=2.4, 14.0 Hz), 7.94 (1H, dd, J=2.4, 8.9 Hz).

3-Fluoro-4-[3-(tert-butyldimethylsilyloxy)pyrrolidinyl]aniline

Palladium on carbon (10%, 500 mg) was added to a mixture of the previous compound (5.0 g) in a mixed solvent of dichloromethane (20 ml) and methanol (100 ml). The mixture was stirred under 1 atmosphere of hydrogen for 6 h, then filtered and the palladium on carbon was washed with methanol and dichloromethane. The combined filtrates were concentrated under reduced pressure to give the title compound (4.52 g); $^1$H NMR (CDCl$_3$), δ 0.08 (6H, s), 0.88 (9H, s), 1.87 (1H, m), 2.11 (1H, m), 3.05 (1H, m), 3.29 (2H, m), 3.56 (1H, m), 4.48 (1H, m), 6.38 (1H, dd, J=2.4, 8.9 Hz), 6.44 (1H, dd, J=2.4, 14.0 Hz), 6.61 (1H, t, J=8.9 Hz).

1-Benzyloxycarbonylamino-4-[3-(tert-butdimethylsilyloxy)pyolidinyl]-3-fluorobenzene:

Benzyl chloroformate (3.0 ml) was added to a mixture of the previous compound (4.52 g) and sodium bicarbonate (1.76 g) in tetrahydrofuran (50 ml) at 0° C. The mixture was stirred at room temperature overnight and then filtered followed by washing with tetrahydrofuran. The combined filtrates were dried over sodium sulfate and concentrated under reduced pressure. The residue obtained was subjected to a silica gel column eluting with hexane/ethyl acetate (90/10). The appropriate fractions was unified and concentrated under reduced pressure to give the title compound (4.40 g); $^1$H NMR (CDCl$_3$), δ 0.08 (6H, s), 0.88 (9H, s), 1.87 (1H, m), 2.11 (1H, m), 3.05 (1H, m), 3.29 (2H, m), 3.56 (1H, m), 4.48 (1H, m), 5.18 (2H, s), 6.59 (1H, t, J=8.9 Hz), 6.88 (1H, dd, J=2.4, 8.9 Hz), 7.10 (1H, dd, J=2.4, 14.0 Hz), 7.36 (5H, m).

(S)-[[3-[4-[3-(tert-butydimethylsilyloxy)pyroldinyl]-3-fluorophenyl]]-2-oxo-5-oxazolidinyl]methanol:

A solution of the previous compound (4.40 g) in dry tetrahydrofliran (50 ml) was cooled to −78° C. under nitrogen and treated with 7.3 ml (1.6M in hexane) of n-BuLi with stirring for 5 min. The mixture was treated with 1.65 ml of (R)-(+)-glycidyl butyrate and was allowed to warm slowly to room temperature overnight. The reaction was quenched by addition of saturated ammonium sulfate solution (10 ml) and the mixture extracted with dichloromethane (3×50 ml). The organic layer combined was washed with brine, dried over sodium sulfate and concentrated under reduced pressure. The residue obtained was chromatographed over a silica gel column eluting with hexane/ethyl acetate with increasing in the content of ethyl acetate (50% to 70%). The appropriate fractions were pooled and concentrated under reduced pressure to give the title compound (1.44 g); $^1$H NMR (CDCl$_3$), δ 0.08 (6H, s), 0.88 (9H, s), 1.91–2.10 (2H, m), 3.18 (1H, m), 3.39—3.48 (2H, m), 3.63 (1H, m), 3.78 (1H, m), 3.87–4.01 (3H, m), 4.48 (1H, m), 4.66 (1H, m), 6.63 (1H, t, J=9.5 Hz), 7.04 (1H, dd, J=2.4, 9.5 Hz), 7.32 (1H, dd, J=2.4, 14.6 Hz).

(S)-[[3-[4-[3-(tert-butylmethylsilyloxy)pyrolidinyl]-3-fluorophenyl]-2-oxo-5-oxazolidinyl]methyl]methanesulfonate:

To a solution of the previous compound (1.44 g) in pyridine (10 ml) was added p-toluene sulfonylchloride (0.88 g) at 0° C. with stirring. The mixture was stirred at room temp. for over night. Water (40 ml) was added slowly to the mixture with stirring and the mixture was futher stirred for 1 hr to give crystals. The crystals were collected by filtration, washed with water and dried at 40° C. under reduced pressure overnight to give the title compound (1.96 g); $^1$H NMR (CDCl$_3$), δ 0.09 (6H, s), 0.88 (9H, s), 1.90–2.08 (2H, m), 2.46 (3H, s), 3.21 (1H, m), 3.40–3.49 (2H, m), 3.65 (1H, m), 3.81 (1H, dd, J=5.9, 8.9 Hz), 4.03 (1H, t, J=8.9 Hz), 4.24 (2H, m), 4.49 (1H, m), 4.80 (1H, m), 6.63 (1H, t, J=9.5 Hz), 6.96 (1H, dd, J=2.4, 9.5 Hz), 7.23 (1H, dd, J=2.4, 14.6 Hz), 7.36 (2H, d, J=7.8 Hz), 7.79 (2H, d, J=7.8 Hz).

(S)-N-[[3-[4-[3-(tert-butyldimethylsilyloxy)pyrrolidinyl]-3-fluorophenyl]-2-oxo-5-oxazolidinyl]methyl]acetamide:

A mixture of the previous compound (1.96 g) in dimethylformamide (20 ml) was treated with sodium azide (455 mg) and warmed at 60° C. for over night. After cooling to room temperature, the mixture was filtered and the precipitate was washed with dichloromethane. The combined filtrates were concentrated under reduced pressure. The residue obtained was chromatographed over a silica gel column eluting with hexane/acetone (80/20). The appropriate fractions were combined and concentrated under reduced pressure to give a compound (1.40 g). A solution of this compound in dry tetrahydrofuran (20 ml) was treated with triphenylphosphine (868 mg) and stirred at room temp. for 2 hr. The mixtrure was treated with water (0.5 ml) and stirred at 40° C. for 4 hr, then at room temperature overnight. The mixture was concentrated under reduced pressure and dried by azeotropic evaporation with toluene. The residue obtained was suspended in dichloromethane (20 ml) and treated with pyridine (0.5 ml) and acetic anhydride (0.6 ml) at 0° C. The mixture was stirred at room temperature overnight and concentrated under reduced pressure. The residue was subjected to a silica gel column eluting with methanol/dichloromethane with increasing in the content of methanol (1% to 3%). The appropriate fractions were pooled and concentrated under reduced pressure to give the title compound (1.502 g); $^1$H NMR (CDCl$_3$), δ 0.08 (6H, s), 0.88 (9H, s), 1.89–2.09 (2H, m), 2.02 (3H, s), 3.18 (1H, m), 3.36–3.67 (6H, m), 3.71 (1H, dd, J=6.8, 8.9 Hz), 3.99 (1H, t, J=8.9 Hz), 4.48 (1H, m), 4.76 (1H, m), 6.20 (1H, broad, NH), 6.61 (1H, t, J=9.2 Hz), 6.98 (1H, dd, J=2.4, 9.2 Hz), 7.30 (1H, dd, J=2.4, 15.1 Hz).

(S)-N-[[3-[4-(3-hydroxypyrrolidinyl)-3-fluorophenyl]-2-oxo-5-oxazolidinyl]methyl]acetamide:

A mixture of the previous compound (1.50 g) in dry tetrahydrofuran (8 ml) was treated with tetrabutylammonium fluoride (6.7 ml; 1.0M in tetrahydrofuran) at 0° C. and allowed to warm to room temp. with stirring for 4 hr. The mixture was treated with water (50 ml) and extracted with dichloromethane (30 ml×4). The organic layer unified was washed with brine, dried over sodium sulfate and concentrated under reduced pressure. The residue was subjected to a silica gel column eluting with acetone/hexane (80/20). The appropriate fractions were combined and concentrated under reduced pressure to give the title compound (0.77 g); $^1$H NMR (DMSO-d$_6$), δ 1.78–2.00 (2H, m), 1.80 (3H, s), 3.12 (1H, m), 3.26–3.54 (5H, m), 3.67 (1H, dd, J=6.8, 8.9 Hz), 4.04 (1H, t, J=8.9 Hz), 4.34 (1H, m), 4.68 (1H, m), 4.91 (1H, d, J=4.1 Hz, OH), 6.72 (1H, t, J=9.7 Hz), 7.07 (1H, dd, J=2.4, 9.7 Hz), 7.38 (1H, dd, J=2.4, 16.2 Hz), 8.23 (1H, t, J=5.7 Hz, NH).

EXAMPLE 11

(S)-N-((3-(3-fluoro-4-(3-oxopyrrolidinyl)phenyl)-2-oxo-5-oxazolidinyl)methyl)acetamide:

7-Benzyl-7-aza-1,4-dioxaspiro(4,5)nonane:

To a suspension of 1-N-benzyl-3-pyrrolidinone (1.92 g) and ethylene glycol (6.81 g) in benzene (70 ml) was added p-toluene sulfonic acid monohydrate (1.93 g). The mixture was refluxed with azeotropic removal of water by means of a Dean-Stark trap for 6 hr. After cooling to room temp., the mixture was washed with sat. sodium bicarbonate aq. (50 ml×3). The water layer was then extracted with dichloromethane (30 ml×3). The organic layers were unified, washed with brine, dried over sodium sulfate and concentrated under reduced pressure to give the title compound (1.57 g); 1H NMR (CDCl$_3$), δ 2.06 (2H, t, J=7.3 Hz), 2.64 (2H, s), 2.66 (2H, t, J=7.3 Hz), 3.61 (2H, s), 3.89 (4H, m), 7.28 (5H, m).

7-Aza-1,4-dioxaspiro(4,5)nonane:

Palladium hydroxide on carbon (20%, 200 mg) was added to a solution of the previous compound (1.57 g) in a mixed solvent of dichloromethane (10 ml) and methanol (20 ml). The mixture was stirred under 3 kgf/cm$^2$ of hydrogen for 2 days, then filtered and the palladium hydroxide on carbon was washed with methanol and dichloromethane. The filtrate combined was concentrated under reduced pressure to give the title compound (1.38 g); 1H NMR (CDCl$_3$), δ 2.17 (2H, t, J=7.3 Hz), 3.35 (2H, s), 3.52 (2H, t, J=7.3 Hz), 3.99 (4H, s).

4-(7-Aza-1,4-dioxaspiro(4,5)nonan-7-yl)-3-fluoronitrobenzene:

Following the general procedure of Example 9 and making non-critical variations but starting with the previous compound (1.38 g), the title compound (1.50 g) was obtained, 1H NMR (CDCl$_3$), δ 2.18 (2H, t, J=7.3 Hz), 3.67 (2H, s), 3.72 (2H, t, J=7.3 Hz), 4.02 (4H, s), 6.53 (1H, t, J=7.3 Hz), 7.88 (1H, dd, J=2.4, 14.0 Hz), 7.94 (1H, dd, J=2.4, 8.9 Hz).

4-(7-aza-1.4-dioxaspiro(4.5)nonan-7-yl)-3-fluoro-1-(phenylmethoxycarbonylamino)-benzene:

Following the general procedure of example 9 and making non-critical variations but starting with the previous compound (1.49 g), the title compound (2.44 g) was obtained, $^1$H NMR (CDCl$_3$), δ 2.16 (2H, t, J=6.8 Hz), 3.41 (2H, t, J=6.8 Hz), 3.46 (2H, s), 3.98 (4H, s), 5.18 (2H, 6), 6.60 (1H, t, J=9.2 Hz), 6.91 (1H, dd, J=2.4, 9.2 Hz), 7.22 (1H, dd, J=2.4, 14.0 Hz), 7.37 (5H, m).

(R)-(3-(3-fluoro-4-(7-aza-1.4-dioxaspiro(4.5)nonan-7-yl)pheny)-2-oxo-5-oxazolidinyl)methanol:

A solution of the previous compound (2.44 g) in dry dimethylformamide (25 ml) was cooled to −78° C. under nitrogen and treated with 6.6 ml (1.0M in tetrahydrofuran) of lithium bis(trimethylsilyl)amide with stirring for 5 min. The mixture was treated with 0.93 ml of (R)-(-)-glycidyl butyrate and was allowed to warm slowly to room temp. for over night. Small excess of lithium bis(trimethylsilyl)amide was quenched by addition of water (5 ml). The mixture was concentrated under reduced pressure and dried by azeotropic evaporation with toluene. The residue was suspended in dichloromethane (100 ml) and the insoluble materaial was removed by filtration. The filtrate was concentrated under reduced pressure and the residue obtained was then subjected to a silica gel column eluting with hexane/acetone (50/50). The appropriate fractions were pooled and concentrated under reduced pressure to give the title compound (1.79 g); $^1$H NMR (DMSO-d$_6$), δ 2.07 (2H, t, J=7.3 Hz), 3.35 (4H, overlapped with signals due to the solvent), 3.50–3.69 (2H, m), 3.78 (1H, dd, J=7.3, 9.2 Hz), 3.92 (4H, s), 4.02 (1H, t, J=9.2 Hz), 4.67 (1H, m), 5.20 (1H, t, J=5.9 Hz, OH), 6.77 (1H, t, J=10.3 Hz), 7.13 (1H, dd, J=2.4, 10.3 Hz), 7.46 (1H, dd, J=2.4, 16.2 Hz).

(R)-N-((3-(3-fluoro-4-(7-aza-1,4-dioxaspiro(4,5)nonan-7-yl)phenyl)-2-oxo-5-oxazolidinyl)methyl)azide:

Following the general procedure of Example 9 and making non-critical variations but starting with the previous compound (1.78 g), the title compound (1.76 g) was obtained, $^1$H NMR (CDCl$_3$), δ 2.14 (2H, t, J=7.3 Hz), 2.44 (3H, s), 3.45 (2H, t, J=7.3 Hz), 3.49 (2H, s), 3.73–4.13 (2H, m), 3.98 (4H, s), 4.24 (2H, m), 4.80 (1H, m), 6.60 (1H, t, J=9.5 Hz), 6.96 (1H, dd, J=2.4, 9.5 Hz), 7.23 (1H, dd, 2.4, 14.6 Hz), 7.36 (2H, d, J=7.8 Hz), 7.78 (2H, d, J=7.8 Hz).

(R)-N-((3-(3-fluoro-4-(7-aza-1,4-dioxaspiro(4,5)nonan-7-yl)phenyl)-2-oxo-5-oxazolidinyl)methyl)acetamide:

Following the general procedure of Example 9 and making non-critical variations, Lindlar catalyst (150 mg) was then added to a mixture of the previous compound (17) (1.45 g) in a mixed solvent of dichloromethane (10 ml) and methanol (40 ml). The mixture was stirred under an atmospheric press. of hydrogen for 2 days, then filtered and the catalyst was washed with methanol and dichloromethane. The filtrate combined was concentrated under reduced pressure. The residue obtanied was suspended in dichloromethane (20 ml) and treated with pyridine (0.3 ml) and acetic anhydride (0.7 ml) at 0° C. The mixture was stirred at room temp. for over night and concentrated under reduced pressure. The residue was subjected to a silica gel column eluting with methanol/dichloromethane with incresing in the content of methanol (2% to 5%). The appropriate fractions were pooled and concentrated under reduced pressure to give the title compound (0.72 g); $^1$H NMR (CDCl$_3$), 8 2.01 (3H, s), 2.16 (2H, t, J=7.3 Hz), 3.43 (2H, t, J=7.3 Hz), 3.47 (2H, s), 3.53–3.67 (2H, m), 3.71 (1H, dd, J=6.8, 9.2 Hz), 3.98 (5H, m), 4.75 (1H, m), 6.27 (1H, broad), 6.61 (1H, t, J=9.2 Hz), 6.99 (1H, dd, J=2.4, 9.2 Hz), 7.33 (1H, dd, J=2.4, 15.1 Hz).

(S)-N-((3-(3-fluoro-4-(3-oxopyrrolidinyl)phenyl)-2-oxo-5-oxazolidinyl)methyl)acetamide:

A mixture of the previous compound (610 mg) in acetone (12 ml) and water (3.7 ml) was treated with p-toluene sulfonic acid monohydrate (609 mg) and refluxed for 3 hours. After cooling to room temp., the mixture was concentrated under reduced pressure. The residue was treated with 5 ml of triethylamine and extracted with dichloromethane (30 ml×5). The organic layers were combined, washed with brine, dried over sodium sulfate and concentrated under reduced pressure. The residue obtained was subjected to a silica gel column eluting with hexane/acetone (50/50). The appropriate fractions were combined and concentrated under reduced pressure to give the title compound (390 mg); $^1$H NMR (CDCl$_3$), δ 2.03 (3H, s), 2.65 (2H, t, J=6.8 Hz), 3.47–3.78 (7H, m), 4.02 (1H, t, J=8.9 Hz), 4.76 (1H, m), 6.18 (1H, t, J=5.9 Hz, NH), 6.77 (1H, t, J=9.2 Hz), 7.09 (1H, dd, J=2.4, 9.2 Hz), 7.43 (lH, dd, J=2.4, 15.1 Hz).

EXAMPLE 12

(S)-N-((3-(3-Fluoro-4-(3-(phenylmethoxyacetylamino)-pyrrolidinyl)phenyl)-2-oxo-5-oxazolidinyl)methyl)acetamide Step 1: 3-Fluoro-1-nitro4-(3-trifluoroacetylamino) pyrrolidinylbenzene A solution of 4.49 g(20.54 mmol) of 3-(trifluoroacetylamino)pyrrolidine hydrochloride and 2.97 g(18.68 mmol) of 3,4-difluoronitrobenzene and 7.16 g(41.10 mmol) of dibasic potassium phosphate in 87 mL DMSO was warmed at 90° C. for 18 h. The mixture was cooled and diluted with 300 mL of ethyl acetate. The solution was extracted with water (5×100 mL) and dried (Na$_2$SO$_4$). Concentration in vacuo afforded a yellow solid which was recrystallized from hot ethyl acetate-hexane to afford 5.0 g(84%) of the title product as a yellow crystalline solid, mp 165°–167° C.

Step 2: 3-Fluoro-1-(phenylmethoxycarbonyl)amino-4-(3-trifluoroacetylamino)pyrrolidinylbenzene A solution of 4.10 g(12.76 mmol) of the nitro compound in 100 mL ethyl acetate was treated with 500 mg of 10% palladium on carbon, followed by hydrogenation at atmospheric pressure for 4 hours. The mixture was filtered through celite washing the filter cake with ethyl acetate. The filtrate was concentrated in vacuo and the residue was dissolved in 50 mL acetone and treated with 75 mL saturated NaHCO$_3$ solution followed by cooling to 0° C. and treatment with 4.36 g(3.64 mL, 25.53 mmol) of benzyl chloroformate. The solution was then warmed to ambient temperature for 18 h. The mixture was diluted with 200 ml ethyl acetate and was extracted with water (2×50 mL) followed by drying (Na$_2$SO$_4$). Concentration in vacuo afforded a beige solid which was recrystallized from hot ethyl acetate-hexane to afford 4.41 g(81%) of the title cbz derivative as faint beige needles, mp 143°–145° C.

Step 3: 3-Fluoro-1-(phenylmethoxycarbonyl)amino-4-(3-(1,3-dimethylexahydro-2-oxo-1,35-triazin-5-yl)pyrrolidinyl)benzene A solution of 1.86 g(4.37 mmol) of the Cbz derivative in 36 mL THF was treated with 50 mL of 2N NaOH solution followed by warming at reflux for 36 h. The solution was cooled and diluted with 50 mL water followed by extraction with ethyl acetate (4×75 mL). The combined organic layers were extracted with saturated NaCl solution followed by drying (Na$_2$SO$_4$) and concentration in vacuo. The amber oil obtained was dissolved in 20 mL dioxane and 40 mL toluene and the resulting solution treated with 385 mg(4.37 mmol) of N, N'-dimethylurea and 5 mL of 37% aqueous formaldehyde solution. The mixture was warmed at reflux until ca. 5 ml water had collected in a Dean-Stark trap. The solution was cooled and concentrated in vacuo. The residue was chromatographed over 180 g of 230–400 mesh silica gel, eluting with 2%(v/v) methanol in dichloromethane. These procedures afforded 1.40 g(73%) of the title product as fine white crystals, mp 192°–194° C.

Step 4: (R)-(3-(3-Fluoro-4-(3-(1,3-dimethylhexahydro-2-oxo-1,3,5-triazin-5-yl)pyrrolidnyl)phenyl)-2-oxo-5-oxazolidinyl)methanol A solution of 737 mg(1.67 mmol) of the triazone in 10 mL DMF at −50° C. was treated with 1.84 mL(1.84 mmol) of lithium hexamethyldisilazide in THF. The solution was stirred at −50° C. for 5 min, followed by addition of 265 mg(0.26 mL, 1.84 mmol) of (R)-(+)-glycidiyl butyrate. The solution was then warmed to ambient temperature for 18 h. The mixture was concentrated in vacuo (ca. 0. 3mmHg) and the residue was chromatographed over 36 g of 230–400mesh silica gel, eluting with 30%(v/v) methanol in dichloromethane. These procedures afforded 400 mg(59%) of the title product as a white solid. $^1$H NMR(CDCl$_3$): δ7.36, 7.05, 6.65, 4.72, 4.27, 4.18, 3.95, 3.77, 3.46, 2.88, 2.17, 1.94.

Step 5: (R)-(3-(3-Fluoro-4-(3-(1,3-dimethylhexahydro-2-oxo-1,3,5-triazin-5-yl)pyrrolidnyl)phenyl)-2-oxo-5-oxazolidinyl)methanesulfonate A solution of 395 mg(0.97 mmol) of the oxazolidinone, and 146 mg(0.20 mL, 1.45 mmol) of triethylamine in 5 mL dichloromethane at 0° C. was treated with 471 mg(0.32 mL) of methanesulfonyl chloride. The solution was stirred at 0° C. for 30 minutes, followed by warming to ambient temperature. The solution was treated with water and the aqueous layer extracted with dichloromethane. The combined organic layers were dried ($Na_2SO_4$) and concentrated in vacuo to afford 460 mg(98%) of the title product as an off-white solid suitable for use in the next step. $^1$H NMR ($CDCl_3$): δ7.33, 7.03, 6.63, 4.89, 4.45, 4.27, 4.18, 4.12, 3.89, 3.76, 3.55, 3.47, 3.38, 3.10, 2.88, 2.16, 2.08, 1.92.

Step 6: (S)-N-((3-(3-Fluoro-4-(3-(phenylmethoxyacetyl-amino)-pyrrolidinyl)phenyl)-2-oxo-5-oxazolidinyl)methyl) acetamide A solution of 460 mg(0.97 mmol) of the mesylate in 15 mL of isopropyl alcohol and 15 mL ammonium hydroxide in a sealed tube was warmed at 100° C. for 18 hours. The mixture was cooled and diluted with water followed by extraction with chloroform. The organic layer was dried ($Na_2SO_4$) and concentrated in vacuo. The residue was dissolved in 4 mL pyridine and treated with 0.5 ml acetic anhydride followed by stirring at ambient temperature for 18 hours. The mixture was concentrated in vacuo to afford an oil which was dissolved in chloroform and extracted with water. The organic layer was dried ($Na_2SO_4$) and concentrated in vacuo to afford 472 mg of the acetamide derivative, which was directly dissolved in 4 mL of 1N HCL solution followed by stirring at ambient temperature for 18 hours. The mixture was concentrated in vacuo and dissolved in 4 mL acetone and treated with 2 mL of saturated $NaHCO_3$ solution followed by treatment with 217 mg(0.14 mL, 1.18 mmol) of benzyloxyacetyl chloride, followed by stirring at ambient temperature for 1 h. The mixture was concentrated in vacuo and the residue was chromatographed over 25 g of 230–400 mesh silica gel, eluting with 2%(v/v) methanol in dichloromethane and then with 3%(v/v) methanol in dichloromethane. These procedures afforded 189 mg(40%) of the benxyloxyacetamide derivative product as a white solid. $^1$H NMR($CDCl_3$): δ7.33, 7.02, 6.81, 6.68, 6.08, 4.75, 4.60, 4.01, 3.71, 3.61, 3.34, 2.32, 2.02, 1.91.

EXAMPLE 13
(S)-N-((3-(3-Fluoro-4-(3-(hydroxyacetylamino) pyrrolidinyl)phenyl)-2-oxo-5-oxazolidinyl)methyl) acetamide Continuing from the procedure of Example 12, Step 6, a solution of 189 mg(0.39 mmol) of the benzyloxyacetamide in 5 mL methanol and 5 mL THF was treated with 200 mg of 10% palladium on carbon followed by hydrogenation at atmospheric pressure for 1 h. The solution was diluted with methanol and filtered through celite, washing the filter cake with methanol. The filtrate was concentrated in vacuo to afford an oil, which was chromatographed over 10 g of 230–400 mesh silica gel, eluting with 7%(v/v) methanol in dichloromethane. These procedures afforded 95 mg(62%) of the hydroxyacetamide derivative product as a pink solid. $^1$H NMR($CDCl_3$): δ7.41, 7.10, 6.78, 4.77, 4.53, 4.10, 4.00, 3.77, 3.57, 3.32, 2.30, 1.99, 1.98.

EXAMPLE 14
(S)-N-[[3-Fluoro-4-(cis-3-(methoxycarbonylamino)-4-methlpyrrolidinyl)phenyl]-2-oxo-5-oxazolidinyl]methyl] acetamide:

Step 1: cis-3-(1,1-dimethylethoxycarbonylamino)-4-methylpyrrolidine

A solution of 1.5 g(5.2 mmol) of cis-1-phenylmethyl-3-(1,1-dimethylethoxycarbonylamino)-4-methylpyrrolidine (cf. U.S. Pat. No. 4,753,953) in 50 mL methanol was treated with 200 mg of $Pd(OH)_2$/C followed by hydrogenation under 1 atmosphere of $H_2$ for 3.5 h. The mixture was filtered through celite, washing the filter cake with methanol. The filtrate was concentrated in vacuo to afford a colorless oil, which was used directly in the next step. $^1$H NMR ($CD_3OD$) δ 4.85, 4.03, 3.14, 3.05, 2.66, 2.45, 2.23, 1.46, 0.95.

Step 2: 3-Fluoro-1-nitro-4-[cis-3-(1.1-dimethylethoxycarbonylamino)-4-methylpyrrolidinyl] benzene A solution of the previously obtained compound and 1.8 g(10.3 mmol) of dibasic potassium phosphate in 40 mL DMSO was warmed at 90° C. for 18 h. The mixture was cooled and diluted with 125 mL ethyl acetate, followed by extraction with water (4×75 mL). The organic layer was dried ($Na_2SO_4$) and concentrated in vacuo to afford 1.75 g of a yellow solid, sufficiently pure for further use. MS (EI) m/z 339 ($M^+$), 339, 282, 266, 223, 222, 208, 207, 154, 70, 57.

Step 3: 3-Fluoro-1-nitro-[cis-3-(1,3-dimethylhexahydro-2-oxo-1,3,5-triazin-5-yl)-4-methylpyrrolidinyl]benzene A solution of 1.75 g(5.17 mmol) of the previous compound in 50 mL trifluoroacetic acid was stirred at ambient temperature for 18 h. The solution was concentrated in vacuo and the red-brown oil obtained was dissolved in ethyl acetate and extracted cautiously with saturated $NaHCO_3$ solution (4×). The combined aqueous layers were extracted with ethyl acetate, and the combined organic layers were dried ($Na_2SO_4$) and concentrated in vacuo. The residue was dissolved in 90 mL toluene and 45 mL dioxane and treated with 1.12 g(12.7 mmol) of N, N'-dimethylurea and 35 mL aqueous formaldehyde, followed by warming at reflux for 2.5 h. The mixture was cooled and concentrated in vacuo. The residue was chromatographed over 200 g of 230–400 mesh silica gel, eluting with 1–2%(v/v) methanol in chloroform. These procedures afforded 3.65 g(86%) of the desired product as an oily yellow solid. MS (EI) m/z 351 ($M^+$), 223, 222, 221, 208, 207, 182, 169, 154, 130, 113.

Step 4: 3-Fluoro-1-(phenylmethoxycarbonyl)amino-[cis-3-(1,3-dimethylhexahydro-2-oxo-1,3,5-triazin-5-yl)-4-methylpyrrolidinyl]benzene A solution of 1.82 g(5.17 mmol) of in 200 mL THF was treated with 750 mg of 10% palladium on carbon, followed by hydrogenation under 45 psi of hydrogen ressure for 3 h. The mixture was cooled to –20° C. followed by addition of 30 mL aturated $NaHCO_3$ solution. The mixture was then treated with 1.10 g(0.92 mL, 6.46 mmol) of benzyl chloroformate, followed by warming to ambient temperature for 18 h. The mixture was filtered through celite, washing the filter cake with methanol and dichloromethane. The filtrate was concentrated in vacuo and the residue was dissolved in dichloromethane and extracted with water (3×30 mL). Drying ($Na_2SO_4$) and concentration in vacuo afforded a purple foam which was chromatographed over 125 g of 230–300 mesh silica gel, eluting with 1–5% methanol in dichloromethane. These procedures afforded 1.74 g(74%) of the title compound as a rigid foam. $^1$H NMR ($CDCl_3$) δ 7.34, 6.92, 6.53, 5.18, 4.19, 4.13, 3.69, 3.58, 3.52, 3.41, 3.15, 2.86, 2.37, 1.05.

Step 5: (R)-(3-(3-Fluoro-4-(cis-3-(1,3-dimethylhexahydro-2-oxo-1,3,5-triazin-5-yl)-4-methylpyrrolidinyl)phenyl)-2-oxo-5-oxazolidinyl)methanol A solution of 860 mg(1.89 mmol) of the previous compound in 25mL THF at –78° C. was treated with 1.3 mL(2.08 mmol) of n-butyllithium in hexane, followed by warming to –50° C. After stirring at –50° C. for 20 minutes, 286 mg(0.28 mL, 1.98 mmol) of (R)-(-)-glycidiyl butyrate was added. The mixture was warmed to 0° C. for 30 minutes and then to ambient temperature for 18 h. The mixture was treated with saturated $NH_4Cl$ solution and was diluted with ethyl acetate and then extracted with water (3×). The aqueous phase was extracted with ethyl acetate and the combined organic layers were dried ($Na_2SO_4$) and concentrated in vacuo to afford a brown oil. This material was chromatographed over 40 g of 230–400 mesh silica gel, eluting with methanol in dichloromethane. These procedures afforded 512 mg(64%) of the title compound as a white rigid foam. $^1$H NMR (CDCl$_3$) δ 7.35, 7.03, 6.60, 4.72, 4.22, 4.14, 3.94, 3.75, 3.70 , 3.60, 3.54, 3.43, 3.18, 2.87, 2.39, 1.05.

Step 6: (R)-(3-(3-Fluoro-4-(cis-3-(1,3-dimethylhexahydro-2-oxo-1,3,5-triazin-5-yl)-4-methylpyrrolidinyl)phenyl)-2-oxo-5-oxazolidinyl)methanesulfonyloxymethane A solution of 1 g(2.37 mmol) of the previous compound and 480 mg(0.66 mL, 4.74 mmol) of triethylamine in 15 mL dichloromethane at 0° C. was treated with 407 mg(0.28 mL, 3.56 mmol) of methanesulfonyl chloride. The solution was stirred at 0° C. for 1.5 h, followed by warming, dilution with dichloromethane and extraction with water (3×). The organic layer was dried (Na$_2$SO$_4$) and concentrated in vacuo to afford the title compound. $^1$H NMR (CDCl$_3$) δ 7.45, 7.02, 6.92, 4.92, 4.50 (, 1 H), 4.43, 4.23, 4.17, 3.91, 3.83, 3.65, 3.50, 3.29, 3.11, 2.89, 2.48, 1.12.

Step 7: (S)-(N)-((3-Fluoro-4-(cis-3-(1,3-dimethylhexahydro-2-oxo-1,3,5-triazin-5-yl)-4-methylpyrolidinyl)phenyl)-2-oxo-5-oxazolidinyl)methyl)acetamide A solution of the previous mesylate in 6 mL THF and 6 mL isopropyl alcohol was treated with 6 mL of concentrated ammonium hydroxide. The mixture was warmed at 100° C. in a sealed tube for 48 h. The mixture was cooled and diluted with ethyl acetate and water. The mixture was extracted with ethyl acetate (2×). The mixture was treated with saturated NaCl solution and then extracted with chloroform (3×). The combined organic layers were dried (Na$_2$SO$_4$) and concentrated in vacuo. The residue was dissolved in 15 mL pyridine and cooled to 0° C. The solution was treated with 0.5 mL acetic anhydride, followed by warming to ambient temperature for 20 h. The mixture was concentrated in vacuo and the residue was chromatographed over 75 g of 230–400 mesh silica gel eluting with methanol in dichloromethane. These procedures afforded 934 mg(85%) of the title compound as a white rigid foam. MS (FAB) m/z 463 (M+H), 464, 463, 462,461, 364, 363, 361, 333, 101, 44.

Step 8: (S)-(N)-((3-Fluoro-4-(cis-3-amino-4-methylprolidinyl)phenyl)-2-oxo-5-oxazolidinyl)methyl)acetamide A solution of 875 mg(1.89 mmol) of the previous compound in 5 mL of 2N HCl solution was stirred at ambient temperature for 20 h. The solution was concentrated in vacuo, and the residue was dried by azeotroping with toluene. These procedures afforded 662 mg(ca. 100%) of the title compound as an amber rigid foam. MS (FAB) m/z 351 (M+H), 427, 352, 351, 350, 349, 255, 123, 101, 89, 44. HRMS (FAB) calcd for C$_{17}$H$_{23}$FN$_4$O$_3$+H$_1$ 351.1832, found 351.1840.

Step 9: (S)-N-[[3-Fluoro-4-(cis-3-(methoxycarbonylamino)-4-methylpyrrolidinyl)phenyl]-2-oxo-5-oxazolidinyl]methyl]acetamide A solution of 150 mg(0.43 mmol) of the previous compound in 6 mL acetone and 3 mL water was treated with 108 mg(1.29 mmol) of NaHCO$_3$ and cooled to 0° C. The solution was then treated with 89 mg(73 μL, 0.96 mmol) of methyl chloroformate. The solution was then diluted with ethyl acetate and extracted with water (3×). Drying (Na$_2$SO$_4$) and concentration in vacuo afforded a white solid, which was subjected to radial chromatography on a 2 mm chromatotron plate, eluting with methanol in dichloromethane. These procedures afforded 155 mg(53%) of the title compound as a white solid. MS (EI) m/z 408 (M+), 409, 408, 364, 334, 333, 318, 289, 276, 215, 56.

EXAMPLE 15

(S)-N-[[3-Fluoro-4-(cis-3-(hydroxyacetylamino)4-methylpyrrolidinyl)phenyl]-2-oxo-5-oxazolidinyl]methyl]acetamide:

Step 1: (S)-N-[[3-Fluoro-4-(cis-3-(phenylmethoxyacetglamino)-4-methylpyrrolidinyl)phenyl]-2-oxo-5-xazolidinyl]methyl]acetamide A solution of 300 mg(0.90 mml) of the amine (Example 14, Step 8) in 14 mL acetone and 7 mL water was treated with 302 mg(3.60 mmol) of NaHCO$_3$ and cooled to 0° C. The solution was then treated with 414 mg(0.35 mL, 2.25 mmol) of benzyloxyacetyl chloride, followed by warming to ambient temperature for 72 h. The mixture was diluted with ethyl acetate and water and the organic layer was extracted with water (3×). The organic layer was dried (Na$_2$SO$_4$) and concentrated in vacuo to afford a brown oil. This material was chromatographed over 30 g of 230–400 mesh silica gel, eluting with methanol in dichloromethane. These procedures afforded 132 mg(30%) of the title compound as a white solid. $^1$H NMR (CDCl$_3$) δ 7.57, 7.36, 7.03, 5.98, 4.77, 4.67, 4.63, 4.04, 3.74, 3.70, 3.63, 3.55, 3.45, 3.38, 2.71, 2.03, 1.07.

Step 2: (S)-N-[[3-Fluoro-4-(cis-3-(hydroxyacetylamino)-4-methylpyrrolidinyl)phenyl]-2-oxo-5-oxazolidinyl]methyl]acetamide A solution of 107 mg(0.21 mmol) of the previous compound in 25 mL methanol was treated with 100 mg of 10% palladium on carbon followed by hydrogenation at one atmosphere for 72 h. The mixture was filtered through celite, and the filtrate was concentrated in vacuo. The residue was subjected to radial chromatography on a 2 mm chromatotron plate, eluting with methanol in dichloromethane. These procedures afforded 24 mg(8%) of the title compound as a light beige solid. MS (EI) m/z 408 (M$^+$), 408, 334, 333, 318, 289, 215, 70, 57, 56, 55.

EXAMPLE 16

(S)-N-[[3-Fluoro-4-(cis-3-(methanesulfonylamino)-4-methylpyrrolidinyl)phenyl]-2-oxo-5-oxazolidinyl]methyl]acetamide:

A slurry of 200 mg(0.57 mmol) of the amine (Example 14, Step 8) in 10 mL dichloromethane was treated with 144 mg(0.20 mL, 1.43 mmol) of triethylamine, followed by cooling of the resulting solution to 0° C. The mixture was treated with 83 mg(56 μL, 0.73 mmol) of methanesulfonyl chloride, followed by warming at ambient temperature for 18 h. The mixture was diluted with 50 mL ethyl acetate, followed by extraction with water (3×30 mL). The organic layer was dried (Na$_2$SO$_4$) and concentrated in vacuo to afford an off-white solid, which was subjected to radial chromatography on a 2 mm chromatotron plate, eluting with methanol in dichloromethane. These procedures afforded 11 mg(45%) of the title compound as a white solid. MS (EI) m/z 428 (M+), 429, 428, 384, 300, 280, 238, 236, 177, 70, 56.

Chart I
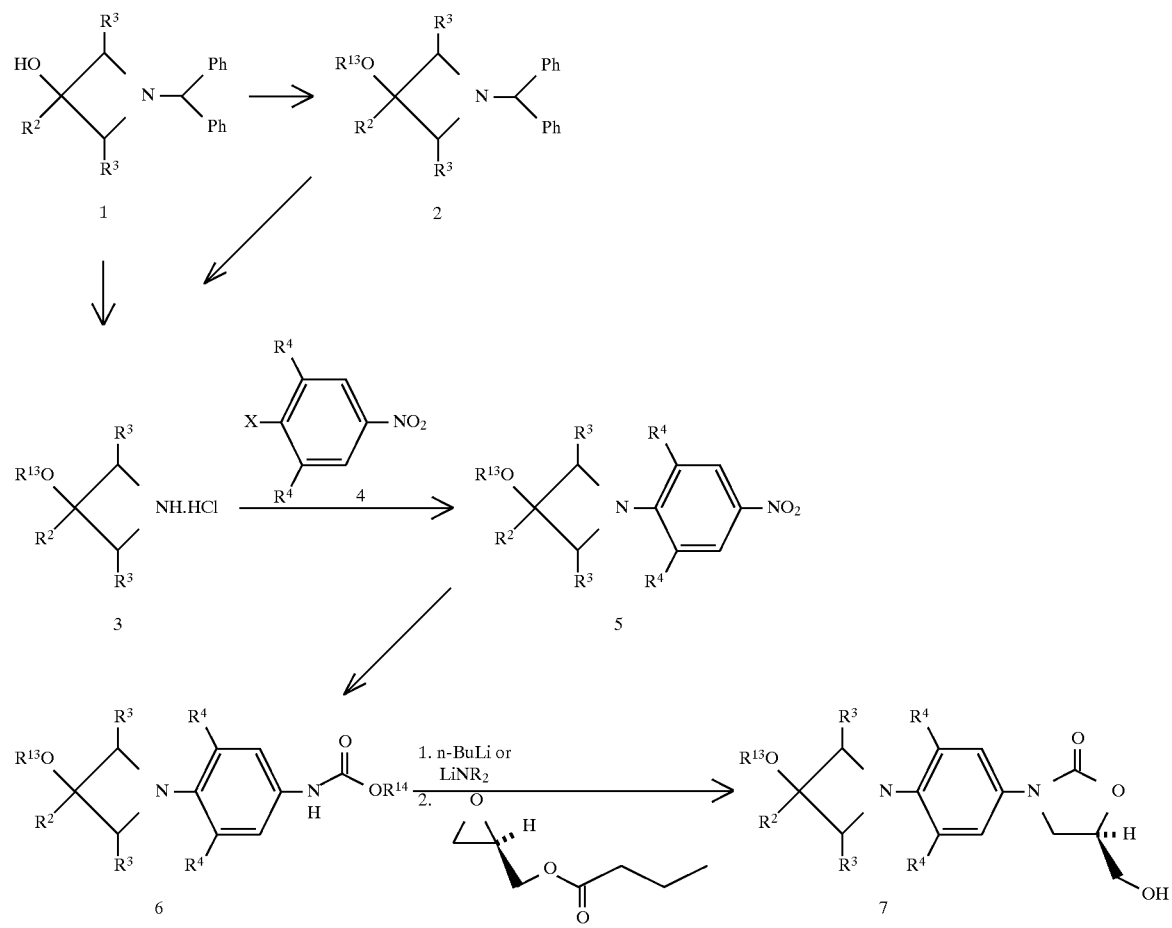
Chart II
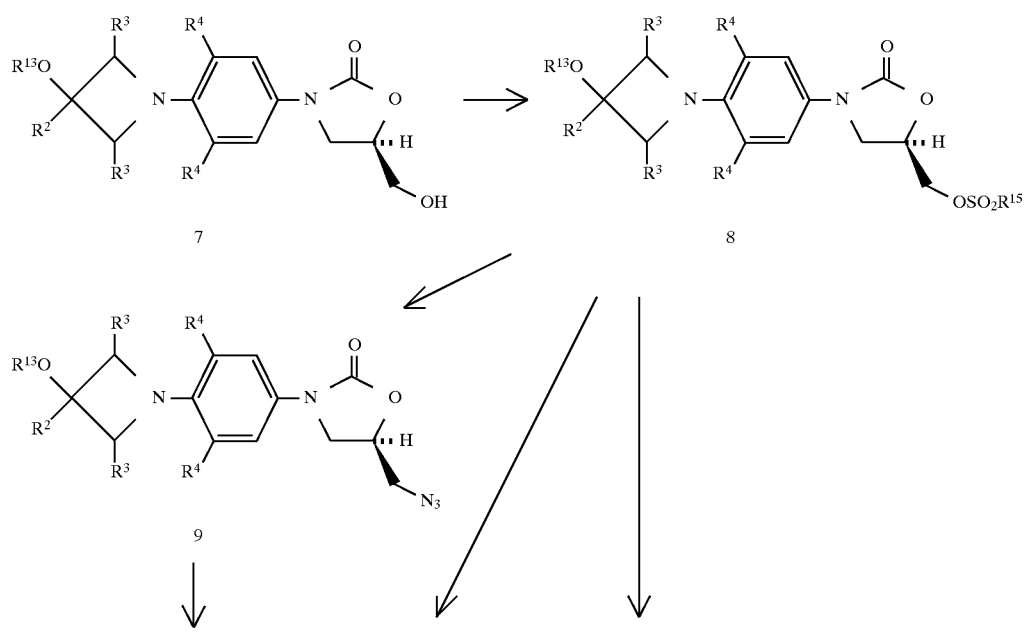

-continued
Chart II
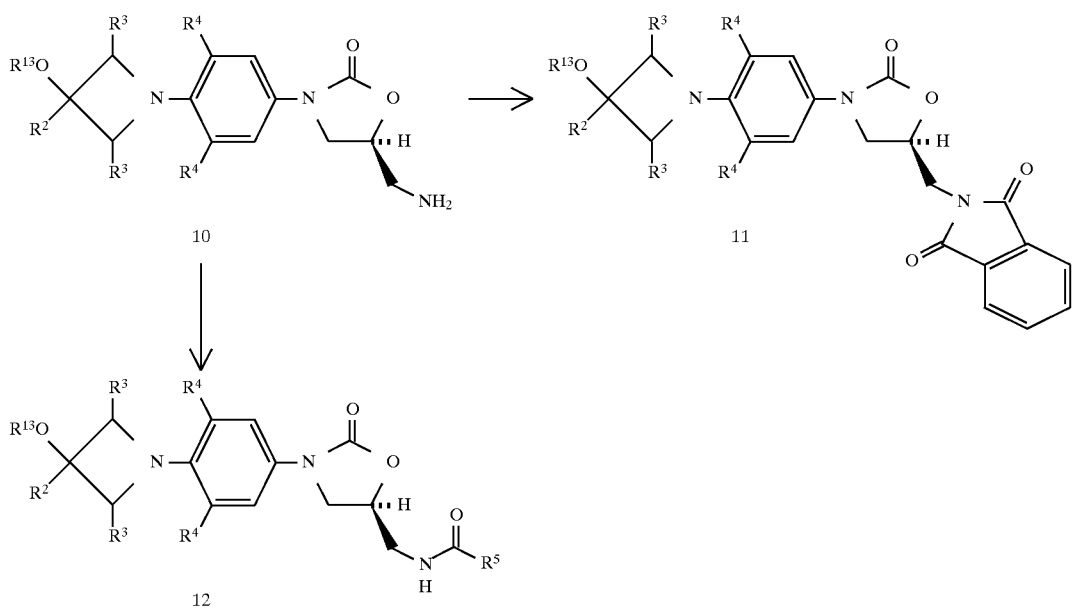
Chart III
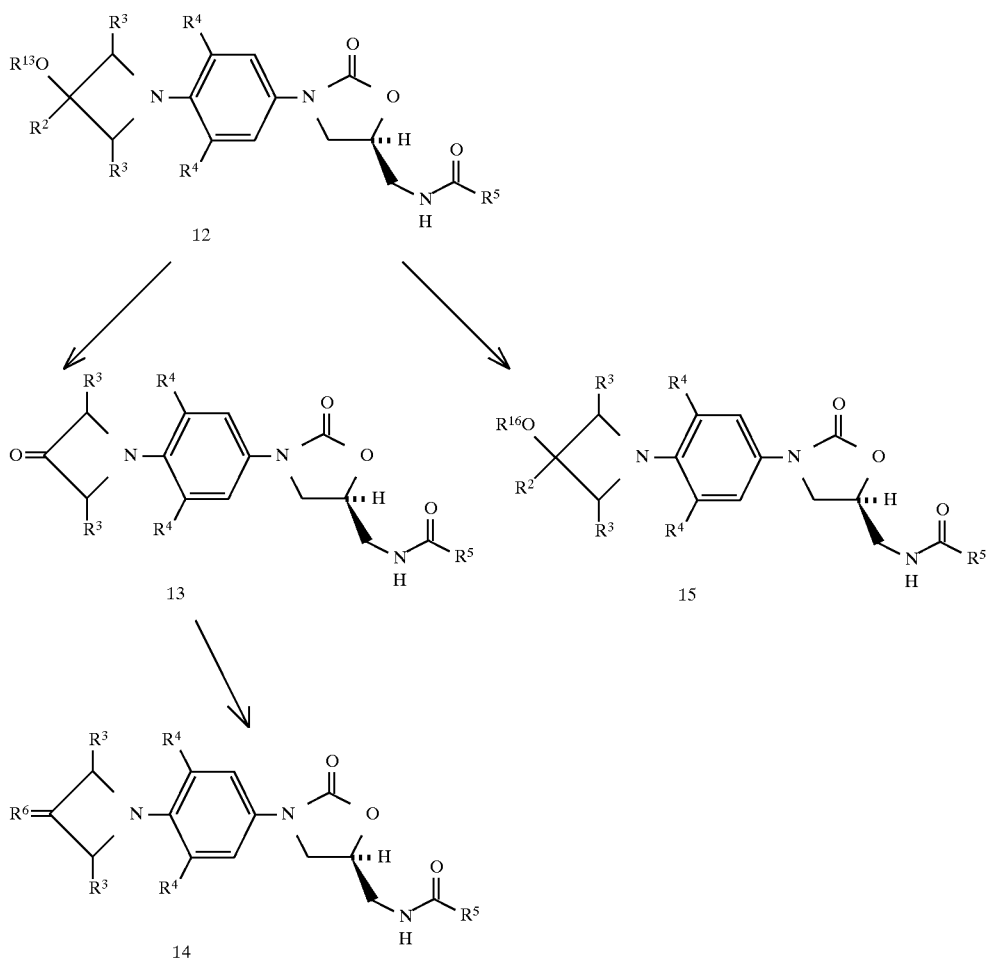

Chart IV
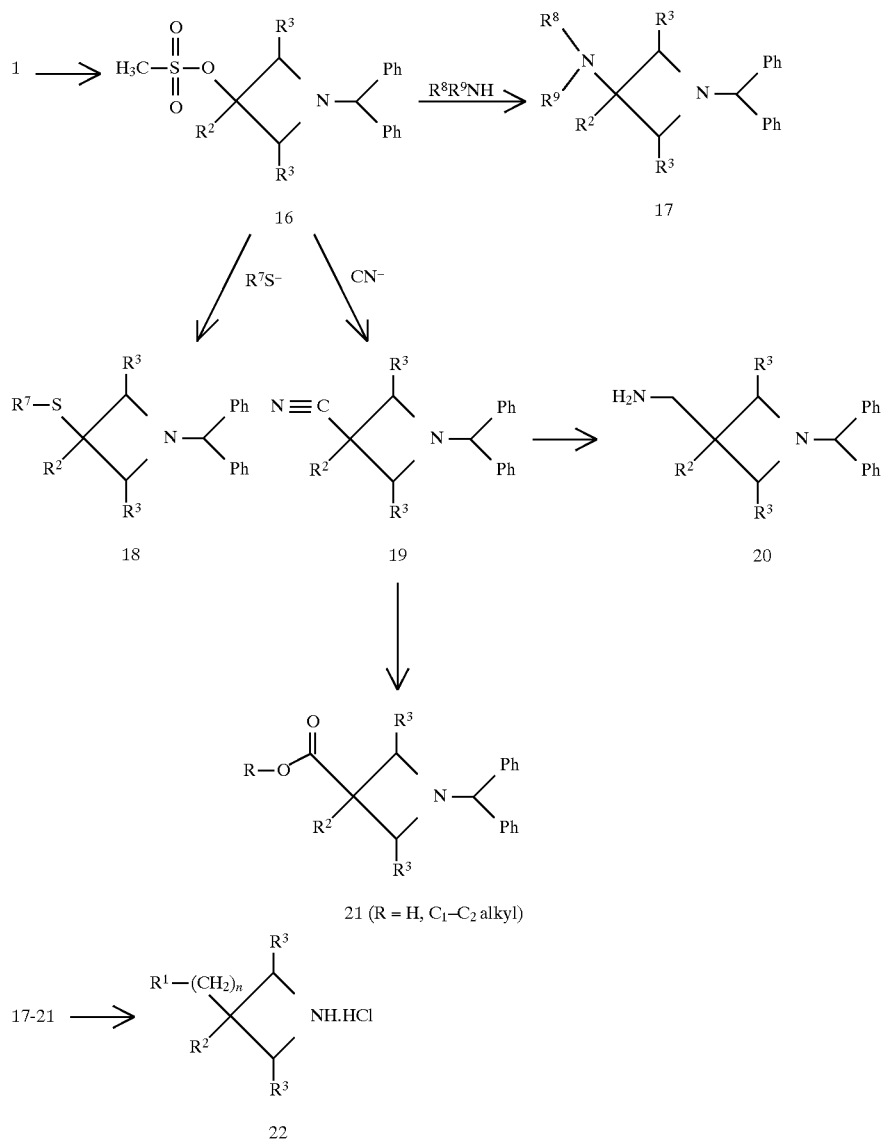
Chart V
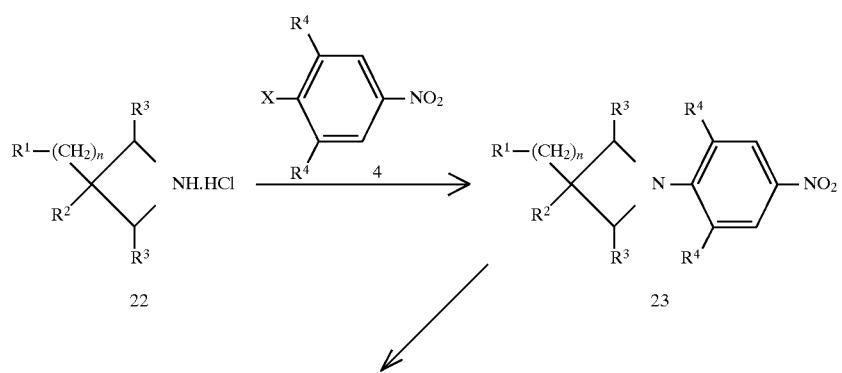

Chart V
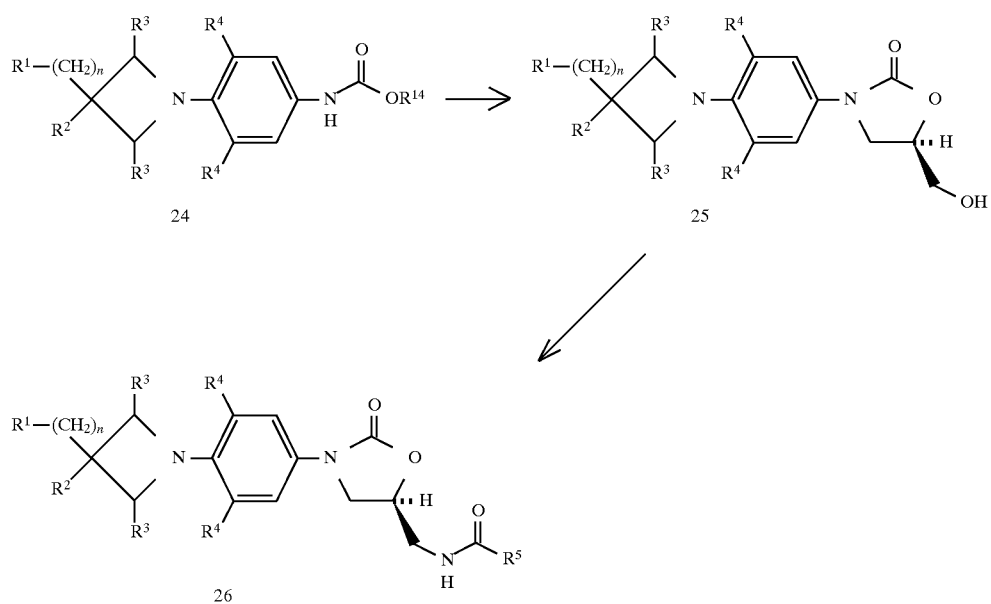
Chart VI
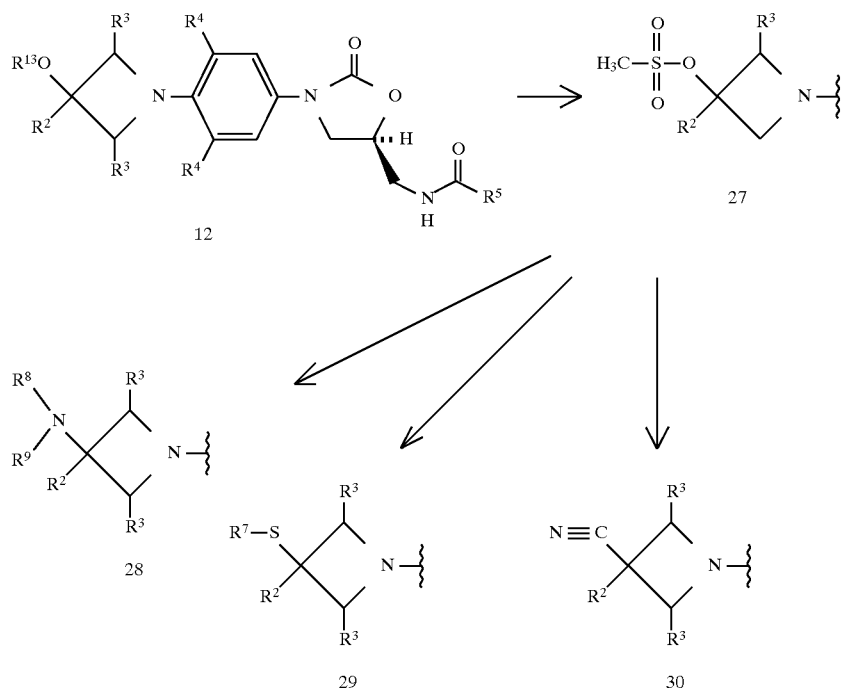

-continued
Chart VI
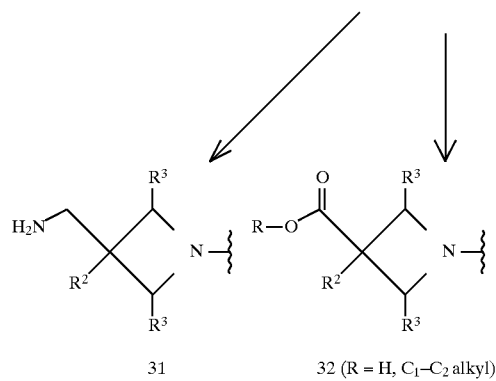
Chart VII
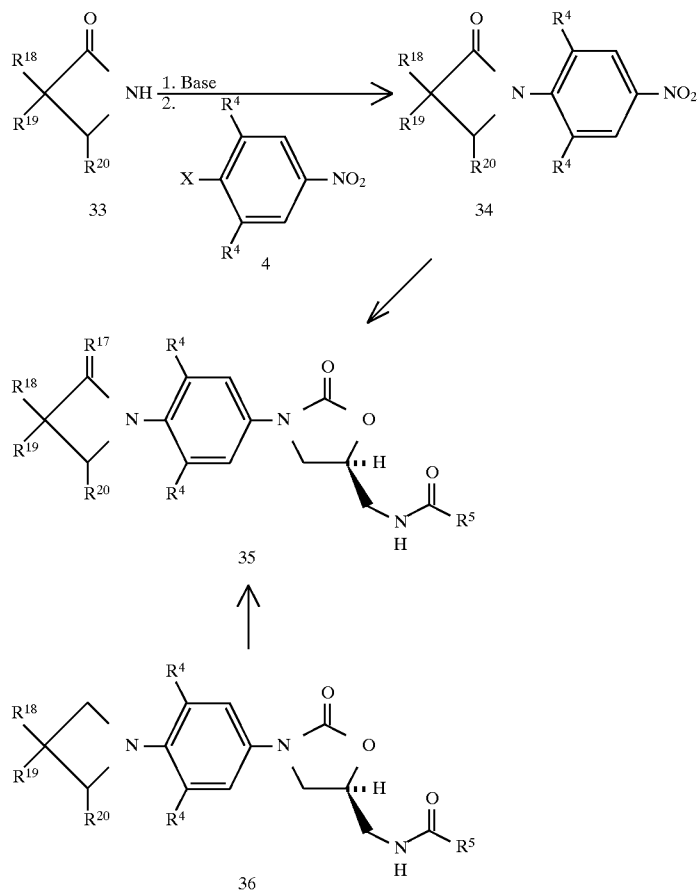

Chart XI
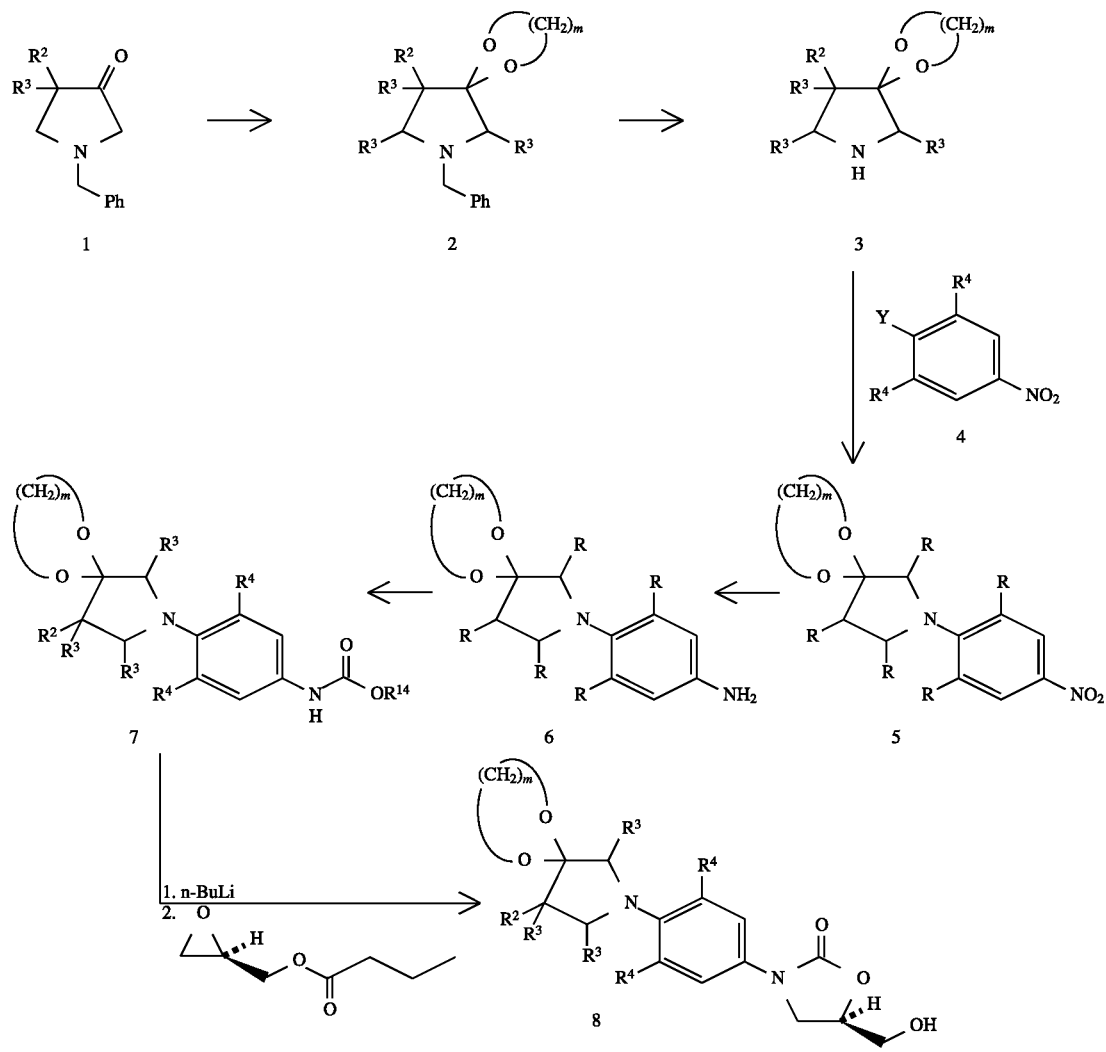

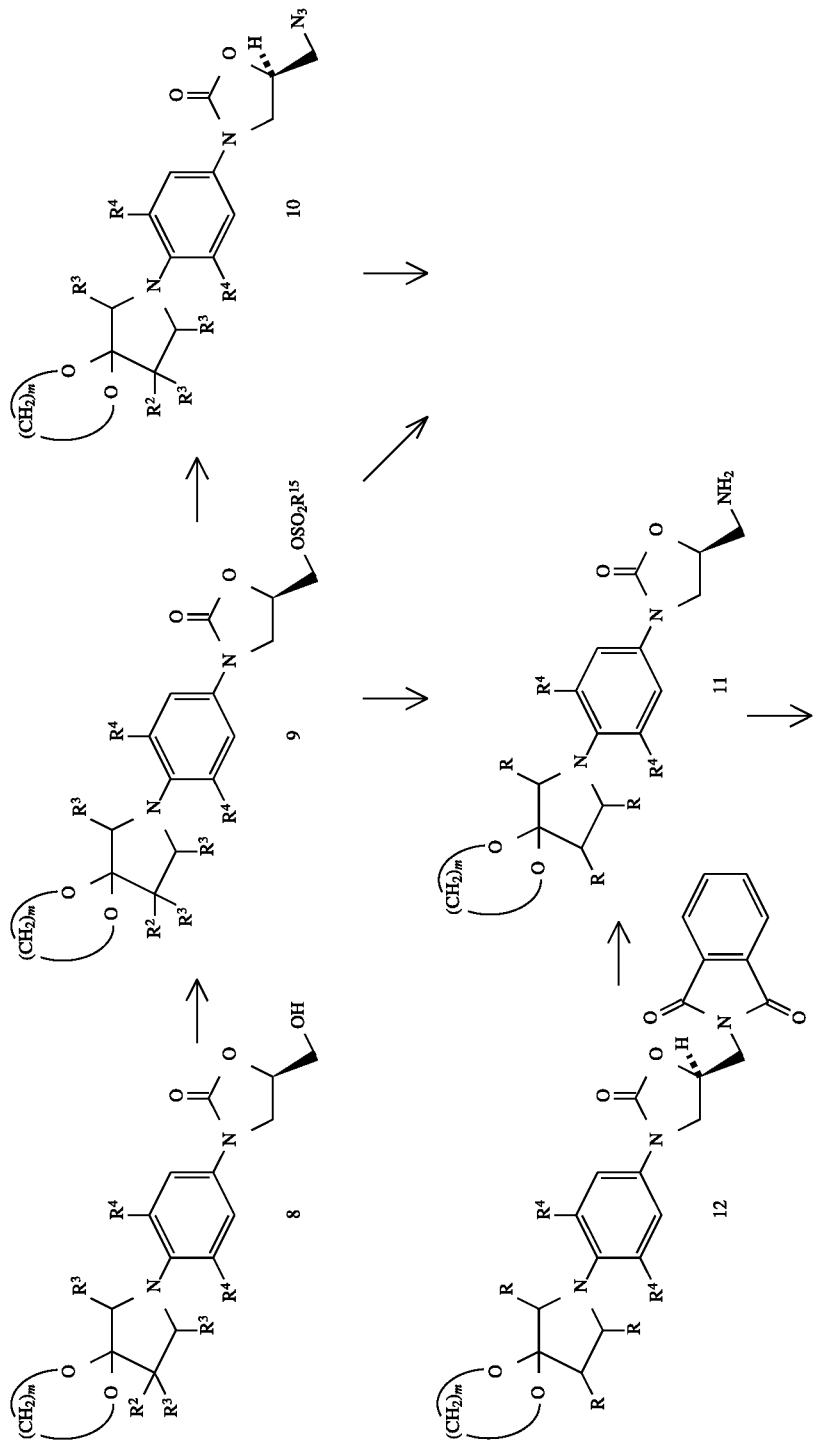

-continued
Chart XII
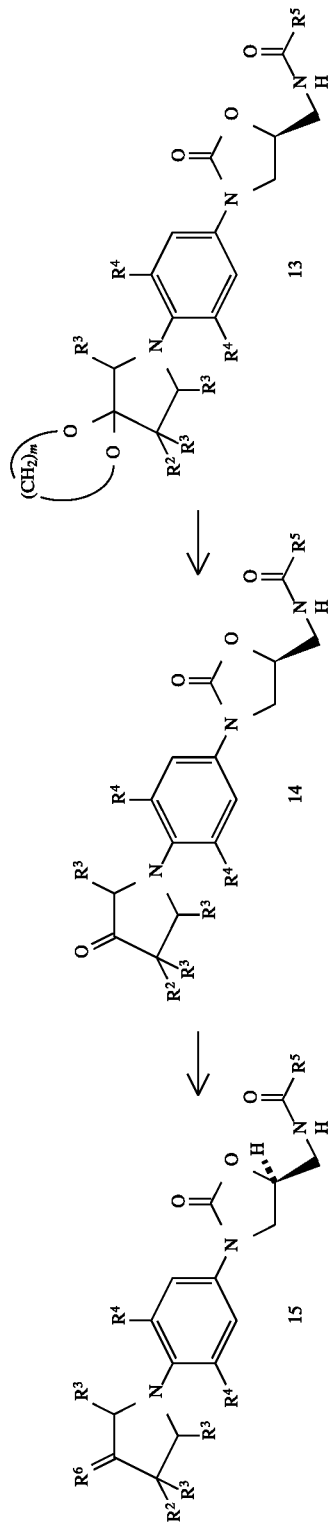

CHART XIII
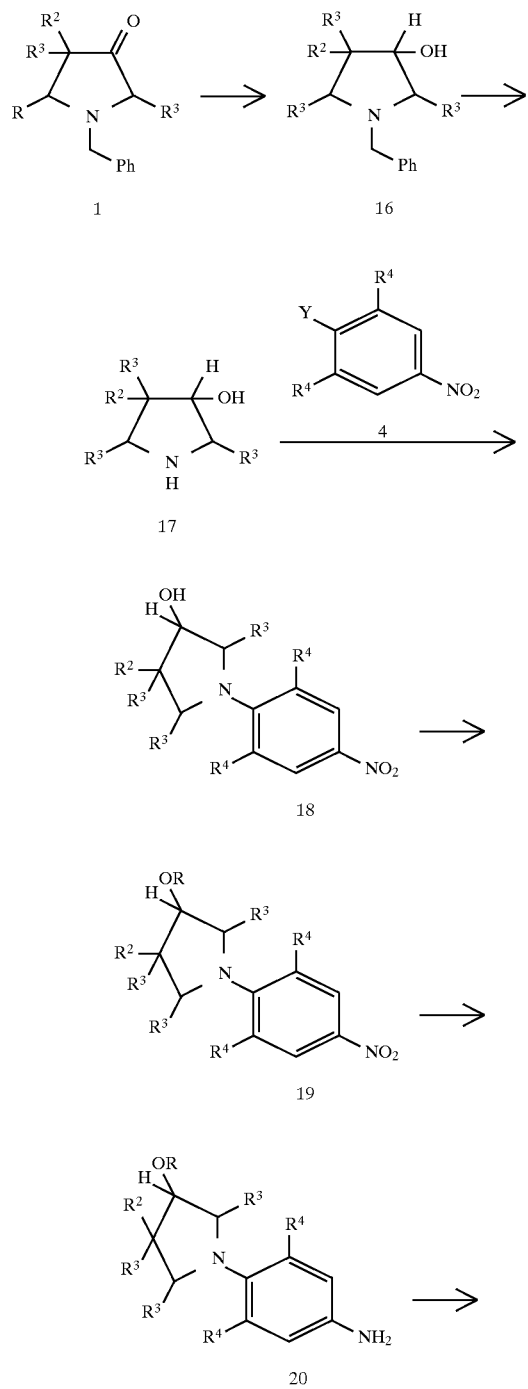
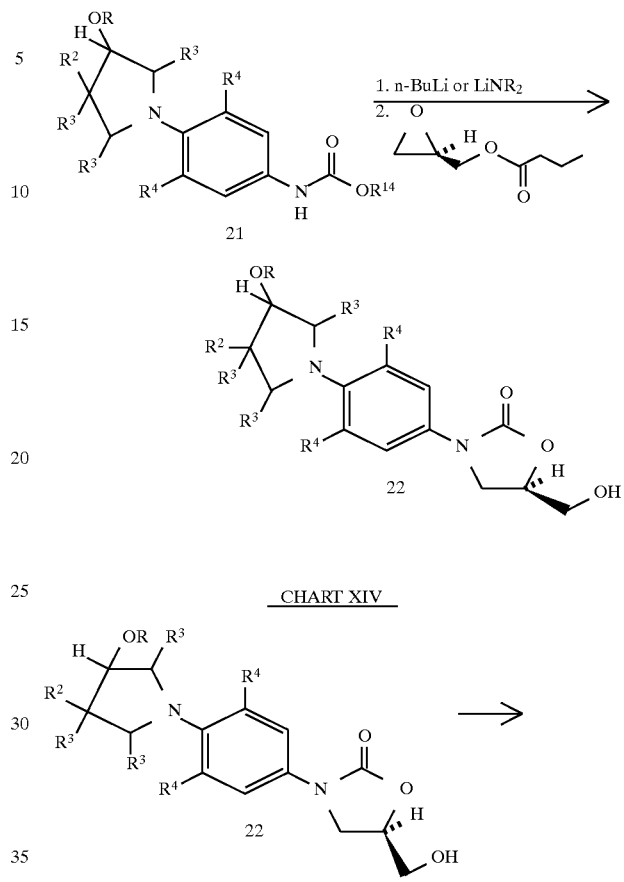
CHART XIV
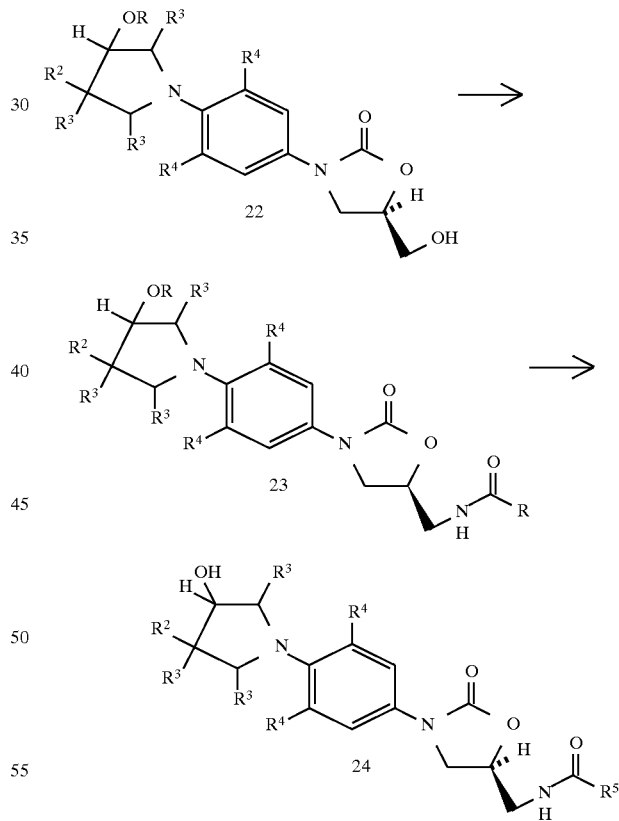

CHART XV
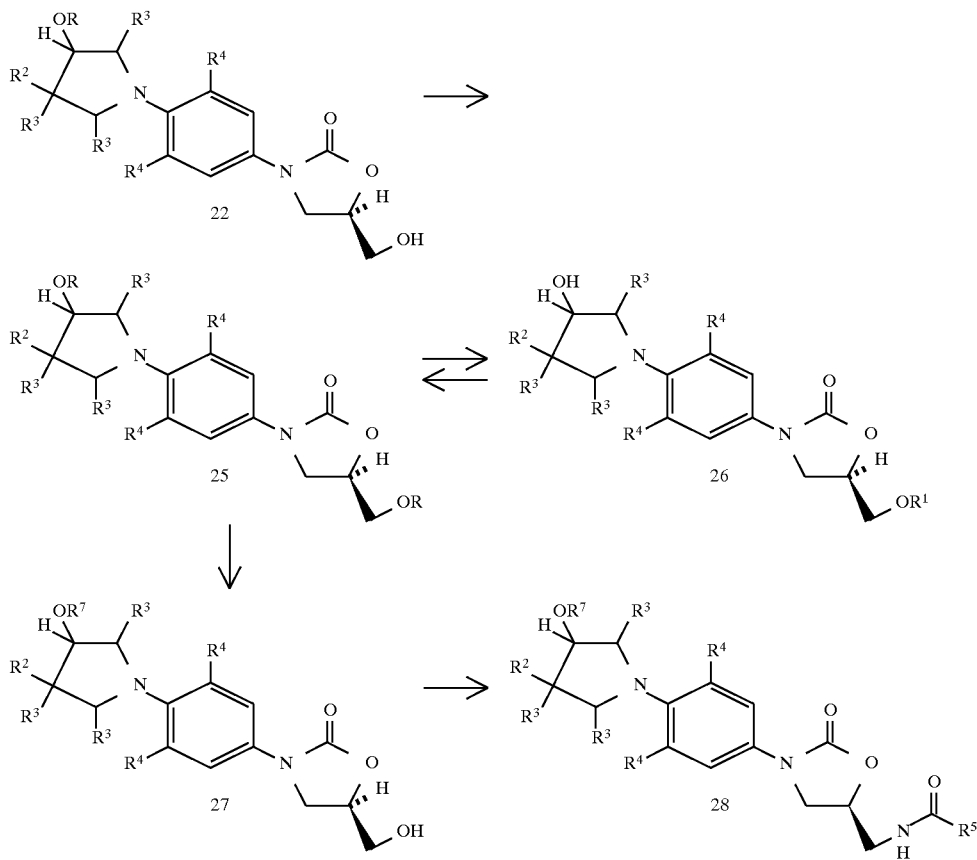
CHART XVI
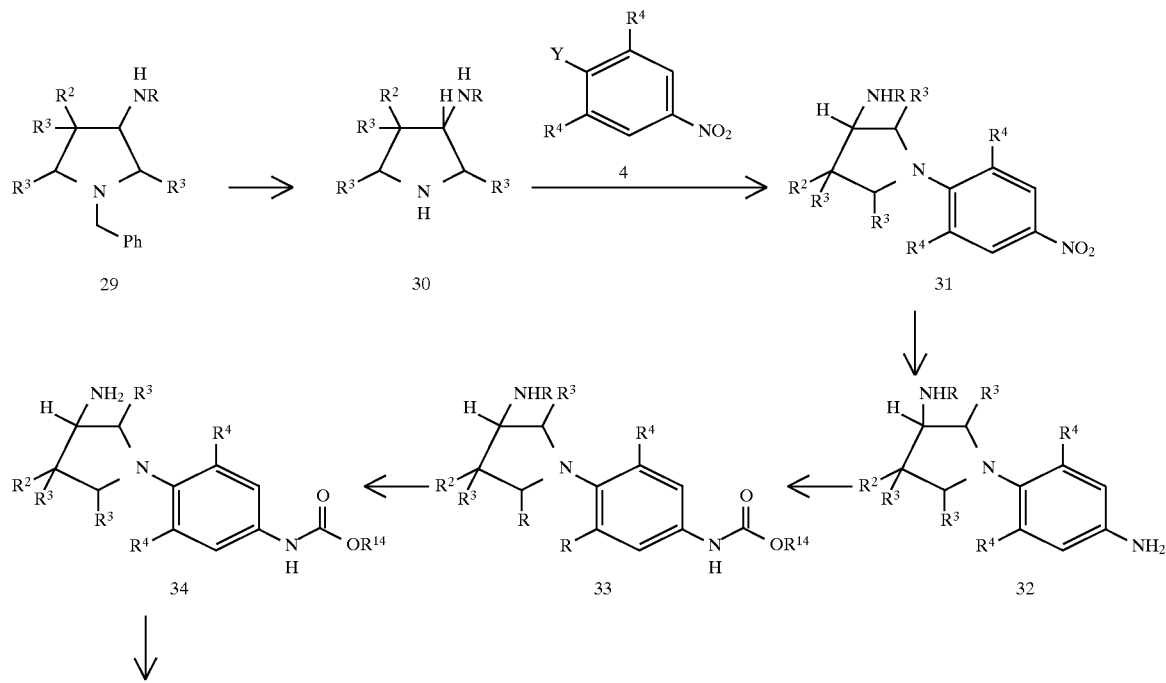

-continued
CHART XVI
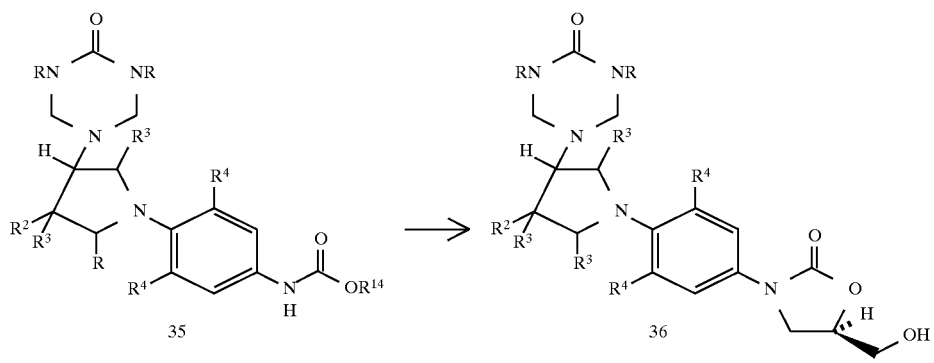
CHART XVII
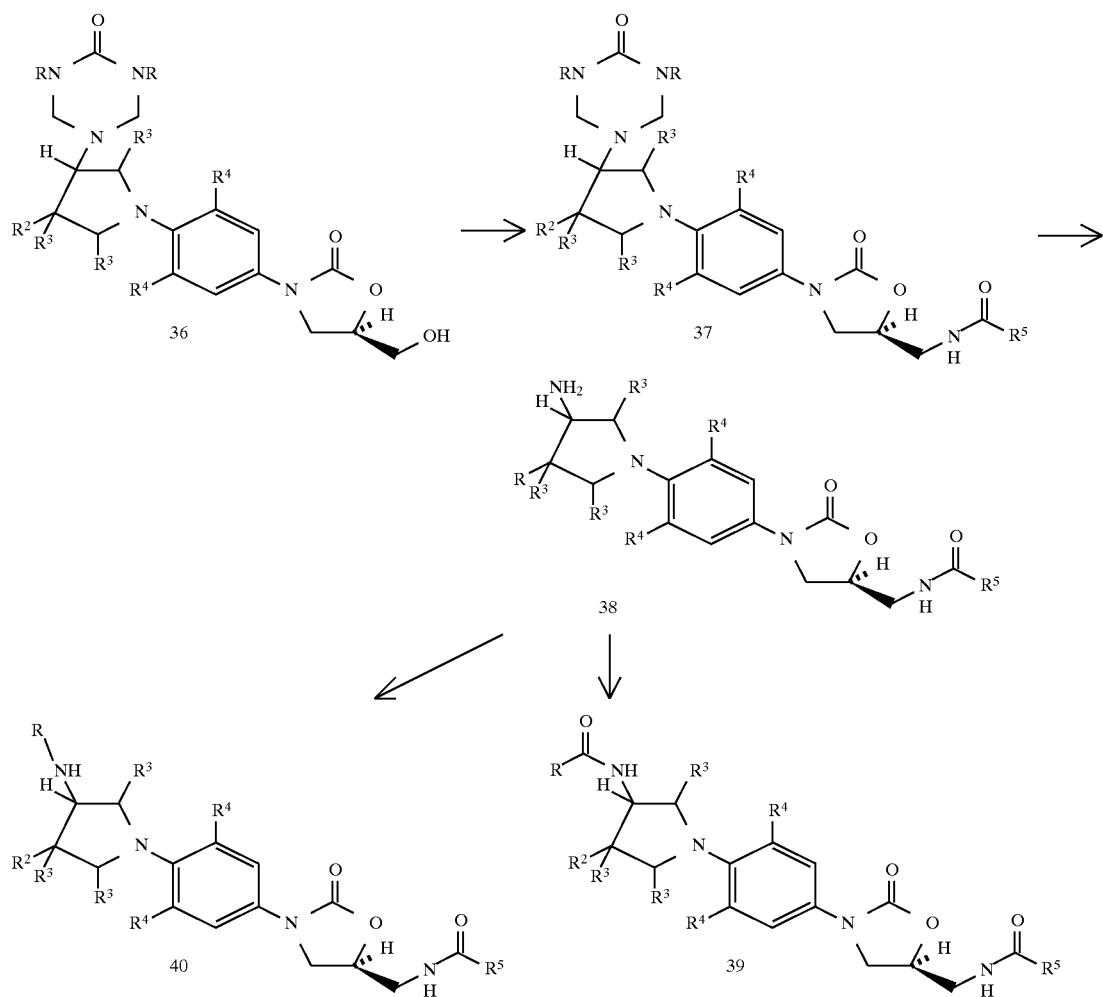

CHART XVIII
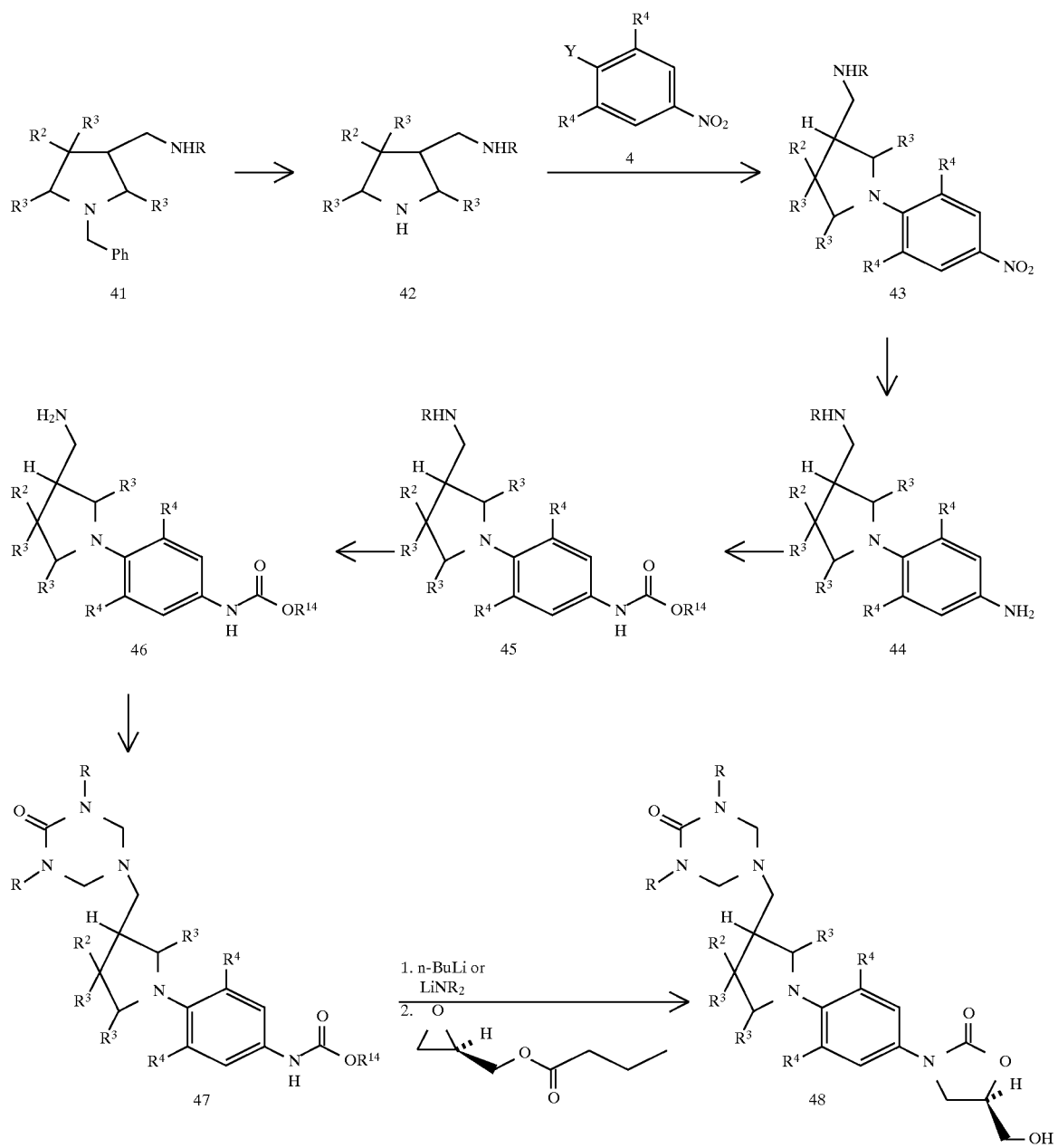

CHART XIX
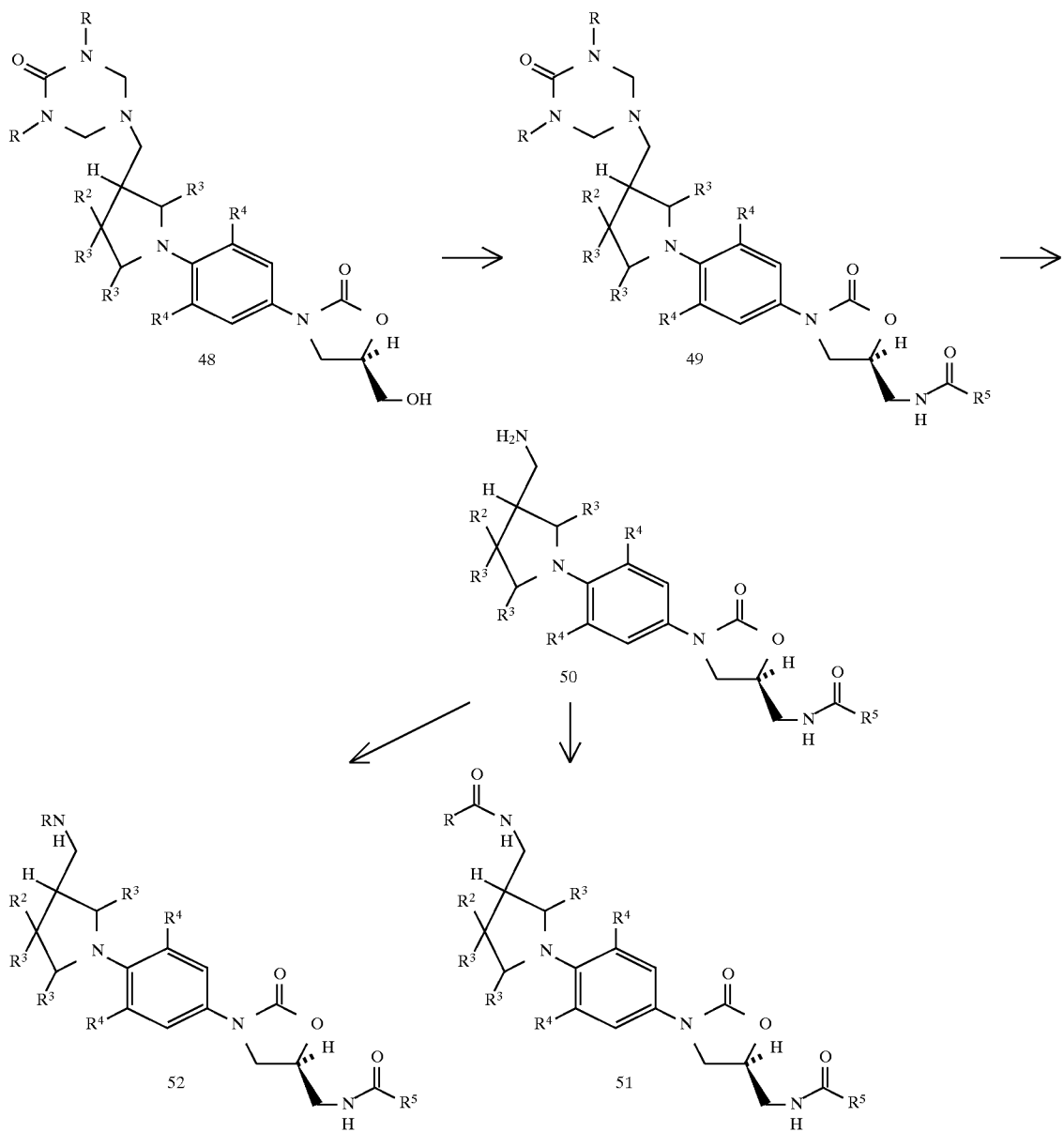
What is claimed:
1. A compound of structural Formula I:
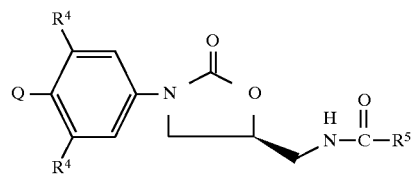
pharmaceutically acceptable salts thereof wherein:
50 is selected from the structures i, ii, iii, iv and v:
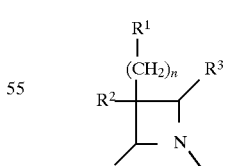
(i)
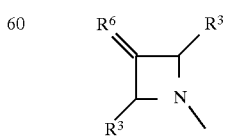
(ii)

-continued

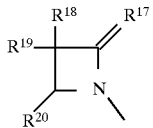 (iii)

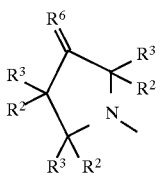 (iv)

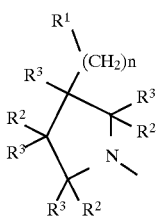 (v)

$R^1$ is
(a) H or F,
(b) $OR^7$,
(c) $SR^7$,
(d) $NR^8R^9$,
(e) CN,
(f) $C_1$–$C_4$ alkoxycarbonyl,
(g) carboxamide,
(h) $C_1$–$C_4$ acyl optionally substituted with one or more of the following: fluorine, hydroxy, $C_1$–$C_4$ alkoxy, $C_1$–$C_4$ acyloxy,
(i) $NHO(C_1$–$C_6$ alkyl), $NHOCH_2Ph$,
(j) $NSO_2R$ where R is $C_1$–$C_6$alkyl optionally substituted with one or more F, Cl, $C_{1-6}$ alkoxy or phenyl;

each $R^2$ is independently selected from
(a) H or F,
(b) OH,
(c) OR where R is $C_1$–$C_6$ alkyl,
(d) $C_1$–$C_4$ alkyl,
(e) Ph;

each $R^3$ is independently selected from
(a) H,
(b) $C_1$–$C_3$ alkyl which can be optionally substituted with F, Cl, hydroxy, $C_1$–$C_3$ alkoxycarbonyl, $C_1$–$C_3$ acyloxy, $C_1$–$C_3$ alkyoxy or $N(C_1$–$C_4$ alkyl)$_2$,
(c) phenyl,
(d) pyridyl;

$R^4$ is independently H, $OCH_3$, F or Cl;
$R^5$ is
(a) hydrogen,
(b) $C_1$–$C_8$ alkyl optionally substituted with one or more of the following: F, Cl, hydroxy, $C_1$–$C_8$ alkoxy, $C_1$–$C_8$ acyloxy,
(c) $C_3$–$C_6$ cycloalkyl,
(d) amino,
(e) $C_1$–$C_8$ alkylamino,
(f) $C_1$–$C_8$ dialkylamino,
(g) $C_1$–$C_8$ alkoxy;

$R^6$ is
(a) O,
(b) S,
(c) $NR^{10}$,
(d) $CR^{11}R^{12}$,
(e) $(OR)_2$, where R=$C_1$–$C_6$ alkyl,
(f) $O(CH_2)_mO$,
(g) $(SR)_2$, where R=$C_1$–$C_6$ alkyl,
(h) $S(CH_2)_mS$
(i) to fill the valence OH and H, H and H, H and F or F and F;

$R^7$ is
(a) H,
(b) $C_1$–$C_8$ alkyl optionally substituted with one or more of the following: F, Cl, —CN, hydroxy, $C_1$–$C_8$ alkoxy, $C_1$–$C_8$ acyloxy, $C_1$–$C_8$ alkoxycarbonyl, phenyl,
(c) $C_1$–$C_8$ acyl optionally substituted with one or more of the following: hydroxy, $C_1$–$C_8$ alkoxy, $C_1$–$C_8$ acyloxy,
(d) $C_1$–$C_8$ alkoxycarbonyl,
(e) carboxamide, optionally substituted with a $C_1$–$C_4$ alkyl or phenyl on the carboxamide nitrogen,
(f) phenyl, optionally substituted with one or more of the following: halogen, CN, $C_1$–$C_3$ alkoxy, $C_1$–$C_3$ alkoxycarbonyl, $C_1$–$C_4$ alkyl optionally substituted with one or more of F or $C_1$–$C_3$ alkoxy;

$R^8$ and $R^9$ are independently selected from:
(a) H
(b) $C_1$–$C_8$ alkyl optionally substituted with one or more of the following: F, Cl, —CN, hydroxy, $C_1$–$C_8$ alkoxy, $C_1$–$C_8$ acyloxy, $C_1$–$C_8$ alkoxycarbonyl, phenyl,
(c) $C_1$–$C_8$ acyl optionally substituted with one or more of the following: hydroxy, $C_1$–$C_8$ alkoxy, $C_1$–$C_8$ acyloxy, amino, $C_1$–$C_4$ acylamino, amino-$C_1$–$C_4$ acylamino,
(d) benzoyl optionally substituted with one or more of the following: F, Cl, hydroxy, $C_1$–$C_8$ alkoxy, $C_1$–$C_8$ acyloxy, amino, $C_1$–$C_4$ acylamino, $C_1$–$C_4$ alkoxycarbonylamino,
(e) $C_1$–$C_8$ alkoxycarbonyl, benzyloxycarbonyl, tertbutoxycarbonyl,
(f) carboxamide, optionally substituted with a $C_1$–$C_4$ alkyl or phenyl on the carboxamide nitrogen
(g) trifluoracetyl
(h) $CO(C_1$–$C_6$ alkyl);

$R^{10}$ is
(a) H,
(b) $OR^7$,
(c) $NHR^7$,
(d) $C_1$–$C_8$ alkyl optionally substituted with phenyl;

$R^{11}$ and $R^{12}$ are independently selected from:
(a) H, F,
(b) $C_1$–$C_4$ alkyl optionally substituted with halogen, hydroxy, $C_1$–$C_4$ alkoxy, $C_1$–$C_4$ alkoxycarbonyl, phenyl,
(c) $C_1$–$C_8$ acyl,
(d) $C_1$–$C_4$ alkoxycarbonyl,
(e) CN;

$R^{17}$ is
(a) O,
(b) S;

$R^{18}$ and $R^{19}$ are independently selected from:
(a) H,
(b) $C_1$–$C_4$ alkyl optionally substituted with halogen, hydroxy, $C_1$–$C_4$ alkoxy, (c) OH,
(d) $C_1$–$C_4$ alkoxy optionally substituted with hydroxy or $C_1$–$C_4$ alkoxy,
(e) $NR^8R^9$
(f) —OC(O)$C_1$–$C_4$ alkyl;
$R^{20}$ is
(a) H,
(b) $CH_3$;
n is 0 or 1 and m is 2 or 3.

2. The compound of claim 1 wherein Q is structure (i).
3. The compound of claim 1 wherein Q is structure (ii).
4. The compound of claim 1 wherein Q is structure (iii).
5. The compound of claim 1 wherein Q is structure (iv).
6. The compound of claim 1 wherein Q is structure (v).
7. The compound of claim 1 wherein each $R^4$ is fluorine.
8. The compound of claim 1 wherein one $R^4$ is fluorine and the other is hydrogen.
9. The compound of claim 1 wherein $R^5$ is hydrogen, methoxy or methyl.
10. The compound of claim 1 wherein $R^6$ is oxygen, $OCH_2CH_2O$, HOH or $NOCH_3$.
11. A method for treating microbial infections in warm blooded animals, including humans comprising administering to a patient a pharmaceutically effective amount of a compound of Formula I as shown in claim 1.
12. A compound of claim 1 which is
   (a) (S)-N-[[3-[3-fluoro-4-(3-methoxy-1-azetidinyl)phenyl]-2-oxo-5-oxazolidinyl]methyl]acetamide.;
   (b) (S)-N-[[3-[3-fluoro-4-(3-hydroxy-1-azetidinyl)phenyl]-2-oxo-5-oxazolidinyl]methyl]acetamide;
   (c) (S)-N-[[3-[3-fluoro-4-[3-[N-(2-fluoroethyl)-N-methylamino]-1-azetidinyl]phenyl]-2-oxo-5-oxazolidinyl]methyl]acetamide;
   (d) (S)-N-[[3-[3-fluoro-4-(3-oxo-1-azetidinyl)phenyl]-2-oxo-5-oxazolidinyl]methyl]acetamide;
   (e) (S)-N-[[3-[3-fluoro-4-[3-(methoxyimino)-1-azetidinyl]phenyl]-2-oxo-5-oxazolidinyl]methyl]acetamide;
   (f) (S)-N-[[3-[3-fluoro-4-(3-methoxy-3-methyl-1-azetidinyl)phenyl]-2-oxo-5-oxazolidinyl]methyl]acetamide;
   (g) (S)-N-[[3-[3-fluoro-4-(3-hydroxy-3-methyl-1-azetidinyl)phenyl]-2-oxo-5-oxazolidinyl]methyl]acetamide;
   (h) (S)-N-[[3-[4-(1-aza-5,5-dimethyl-4,6-dioxabicyclo[3.3.0]octan-1-yl)-3-fluorophenyl]-2-oxo-5-oxazolidinyl]methyl]acetamide;
   (i) (S)-N-[[3-[4-(3,4-cis-dihydroxypyrrolidinyl)-3-fluorophenyl]-2-oxo-5-oxazolidinyl]methyl]acetamide;
   (j) (S)-N-[[3-[4-(3-hydroxypyrrolidinyl)-3-fluorophenyl]-2-oxo-5-oxazolidinyl]methyl]acetamide;
   (k) (S)-N-((3-(3-fluoro-4-(3-oxopyrrolidinyl)phenyl)-2-oxo-5-oxazolidinyl)methyl)acetamide;
   (l) (S)-N-((3-(3-fluoro-4-(3-(phenylmethoxyacetylamino)-pyrrolidinyl)phenyl)-2-oxo-5-oxazolidinyl)methyl)acetamide;
   (m) (S)-N-((3-(3-fluoro-4-(3-(hydroxyacetylamino)pyrrolidinyl)phenyl)-2-oxo-5-oxazolidinyl)methyl)acetamide;
   (n) (S)-N-[[3-fluoro-4-(cis-3-(methoxycarbonylamino)-4-methylpyrrolidinyl)phenyl]-2-oxo-5-oxazolidinyl]methyl]acetamnide;
   (o) (S)-N-[[3-fluoro-4-(cis-3-(hydroxyacetylamino)-4-methylpyrrolidinyl)phenyl]-2-oxo-5-oxazolidinyl]methyl]acetamide; or
   (p) (S)-N-[[3-fluoro-4-(cis-3-(methanesulfonylamino)-4-methylpyrrolidinyl)phenyl]-2-oxo-5-oxazolidinyl]methyl]acetamide.

* * * * *